US007585956B2

(12) United States Patent
Cai et al.

(10) Patent No.: US 7,585,956 B2
(45) Date of Patent: Sep. 8, 2009

(54) QUANTITATIVE TRAIT LOCI AND SOMATOSTATIN

(75) Inventors: Li Cai, Austin, TX (US); Jeremy Taylor, Columbia, MO (US); Kerrie-Ann Smyth, Curtin (AU); Brian Findeisen, Liberty Hills, TX (US); Cathi Lehn, Cliffside Park, NJ (US); Sara Davis, Betram, TX (US); Scott Davis, Betram, TX (US)

(73) Assignee: The Texas A & M University System, College Station, TX (US)

( * ) Notice: Subject to any disclaimer, the term of this patent is extended or adjusted under 35 U.S.C. 154(b) by 363 days.

(21) Appl. No.: 10/379,008

(22) Filed: Mar. 4, 2003

(65) Prior Publication Data

US 2004/0018511 A1  Jan. 29, 2004

Related U.S. Application Data

(60) Provisional application No. 60/361,589, filed on Mar. 4, 2002.

(51) Int. Cl.
C07H 21/02 (2006.01)
C07H 21/04 (2006.01)
C12Q 1/68 (2006.01)
C12P 19/34 (2006.01)

(52) U.S. Cl. ............... 536/23.1; 536/24.31; 536/24.33; 435/6; 435/91.2

(58) Field of Classification Search ................ None
See application file for complete search history.

(56) References Cited

FOREIGN PATENT DOCUMENTS

WO  WO 9511995 A1 *  5/1995
WO  WO 9952942 A2 * 10/1999

OTHER PUBLICATIONS

Bork P. et al 'Convergent evolution of similar enzymatic function on different protein folds: the hexokinase, ribokinase, and galactokinase families of sugar kinases.' Protein Sci. Jan. 1993;2(1):31-40.*
Juppner H 'Functional properties of the PTH/PTHrP receptor.' Bone. Aug. 1995;17(2 Suppl):39S-42S.*
Furu VM 'Cloning and Characterization of the Bovine Somatotropin and Somatostain Genes to Detect Selection Markers' Dissertation fro the University of Connecticut, 1999, pp. 1-211.*
GeneAmp DNA Amplification Reagent Kit, 1988, Perkin Elmer Cetus, pp. 1-3.*
Buck GA et al 'Design strategies and performance of custom DNA sequencing primers.' Biotechniques. Sep. 1999;27(3):528-36.*
Boehringer Mannheim 1997 Biochemicals Catalog 'Hexanucleotide Mix', cover and p. 95.*
Andersson, L., C.S. Haley, H. Ellegren, S.A. Knott, M. Johnsson, et al. 1994. Genetic mapping of quantitative trait loci for growth and fatness in pigs. Science 263: 1771-1774.

Grobet, L., D. Poncelet, L.J. Royo, B. Brouwers, D. Pirottin, et al. 1997. A deletion in the bovine myostatin gene causes the double-muscled phenotype in cattle. Nat. Genet. 17: 71-74.
Grobet, L., D. Poncelet, L. J. Royo, B. Brouwers, D. Pirottin, et al., 1998 Molecular definition of an allelic series of mutations disrupting the myostatin function and causing double-muscling in cattle. Mamm. Genome 9: 210-213.
Haley, C.S. and S.A. Knott. 1992. A simple regression method for mapping quantitative trait loci in line crosses using flanking markers. Heredity 69: 315-324.
Brenneman, R.A., S.K. Davis, J.O. Sanders, B.M. Burns, T.C. Wheeler et al. 1996. The polled locus maps to BTA1 in a *Bos indicus* x *Bos Taurus* cross. J. Heredity 87: 156-161.
Cai, L., J.F. Taylor, R.A. Wing, D.S. Gallagher, S. S. Woo, et al. 1995. Construction and characterization of a bovine bacterial artificial chromosome library. Genomics 29: 413-425.
Taylor, J.F., L.L. Coutinho, K. L. Herring, D.S. Gallagher Jr., R. A. Brenneman et al. 1998. Candidate gene analysis of GHI for effects on growth and carcass composition of cattle. Animal Genetics 29:194-201.
Tavianini, M.A., T.E. Hayes, M.D. Magazin, C.D. Minth, and J.E. Dixon. 1984. Isolation, characterization, and DNA sequence of the rat somatostatin gene. J. Biol. Chem. 259: 11798-11803.
Thue, T.D. and S.M. Schmutz. 1995. Localization of the somatostatin gene to bovine chromosome 1q23-q25 by in situ hybridization. Mamm. Genome 6: 688-689.
Shen L.D. and W.J. Rutter. 1984. Sequence of human somatostatin I gene. Science. 224: 168-171.
Gill, C.A. Davis S.K., Taylor, J.F., Cockett N.E. and Bottema C.D.K. 1999. Construction and characterization of an ovine bacterial artificial chromosome library. Mammalian Genome 10:1108-1111.
Taylor, J.F., Eggen, A., Aleyasin, A., Armitage S.M. Barendse W., Beever, J.E., Bishop M.D., Brenneman,, R.A., Burns B.M., Davis, S.K., Elo, K., Harlizius B., Kappes, S.M., Keele, J.W., Kemp, S.J., Kirkpatrick B.W., Lewin, H.A., MA, R.Z., McGraw, R.A., Pomp, D., Stone, R.T., Sugimoto, Y., Teale, A.J., Vaiman, D., Vilkki, J., Williams, J.L., Yeh C.-C., and Zanotti, M.C. 1998. Report of the first workshop on the genetic map of bovine chromosome 1. Animal Genetics 29:228-235.

(Continued)

*Primary Examiner*—Stephen Kapushoc
(74) *Attorney, Agent, or Firm*—Howrey LLP

(57) ABSTRACT

The disclosure relates to the use of genetic traits in livestock for determining breeding characteristics of livestock progeny, and for optimizing the management and marketing of livestock for improving feedlot performance and meat quality. The disclosure specifically relates to genetic markers and single nucleotide polymorphisms (SNPs) in the bovine somatostatin locus, as well as haplotypes that include the somatostatin locus, which are associated with certain quantitative trait loci (QTLs), such as marbling, meat quality grade, and yield grade. In a preferred embodiment, the SNPs and haplotypes are predictive of the increased or decreased amount of tissue marbling in the animal.

5 Claims, 18 Drawing Sheets

OTHER PUBLICATIONS

Sun, H.S., Cai, L., Daviss, S.K., Taylor, J.F., Doud, L.K., Bishop, M.D., Hayes, H., Barendse, W., Vaiman, D., McGraw, R.A., Hirano, T., Sugimoto, Y., and Kirkpatrick, B.W., 1997. Comparative linkage mapping of human chromosome 13 and bovine chromosome 12. Genomics 39:47-54.

Andersson, L. et al. 1996. Comparative genome organization of vertebrates. The first international workshop on comparative genome organization. Mammalian Genome 7: 717-734.

Yeh, C.C., Taylor, J.F., Gallagher, D.S., Sanders, J.O., Turner, J.W., and Davis S.K. 1996. Genetic and physical mapping of the bovine X chromosome. Genomics32:245-252.

Holder, D.A., Arevalo, E., Holder, M.T., Taylor, J.F., and Davis, S.K. 1994. Bovine microsatellite dinucleotide repeat polymorphisms at the TEXAN-1, TEXAN-2, TEXAN-3, TEXAN-4, and TEXAN-5 loci. Animal Genetics 25:201.

Lehn, Cathi Ann. 1998. Positional Cloning of Candidate Genes Affecting Growth in *BOS Taurus X BOS Indicus*. Dissertation; Texas A&M University, College Station, Texas.

L. Furu, "The Bovine Somatostatin Gene: Characterization of the Sequence", *NCBI Nucleotide*, ncbi.nlm.nih.gov/entrez/viewer.fcgi.

S.B. Smith et al., "Carcass Traits and Microsatellite Distributions in Offspring of Sires from Three Geographical Regions of Japan", *Journal of Animal Science*, 79:3041-3051 (2001).

J.W. Lee et al., Parameter Estimates for Genetic Effects on Carcass Traits of Korean Native Cattle, *Journal of Animal Science*, 78:1181-1190 (2000).

C.S. Hale et al., "Decreased Growth in Angus Steers with a Short TG-Microsatellite Allele in the P1 Promoter of the Growth Hormone Receptor Gene", *Journal of Animal Science*, 78:2099-2104 (2000).

E. Casas et al., "Quantitative Trait Loci Affecting Growth and Carcass Composition of Cattle Segregating Alternate Forms of Myostatin", *Journal of Animal Science*, 78:560-569 (2000).

L.M. Furu et al., "Rapid Communication: Cloning and Characterization of the Bovine Somatostatin Gene", *Journal of Animal Science*, 77(2):492-493 (1999).

R.T. Stone et al., "A Primary Screen of the Bovine Genome for Quantitative Trait Loci Affecting Carcass and Growth Traits", *Journal of Animal Science*, 77: 1379-1384 (1999).

B.A. Vieselmeyer et al., "Use of Expected Progeny Differences for Marbling in Beef: I Production Traits", *Journal of Animal Science*, 74:1009-1013 (1996).

* cited by examiner

*Bos taurus* Chromosome 1 Map

Weaning Weight Analysis

Hot Carcass Weight Analysis

Ribeye Muscle Area Analysis

Marbling Analysis

Marbling Analysis

Meat Quality Grade Analysis

Meat Quality Grade Analysis

Warner-Bratzler Shear Force Analysis

Yield Grade Analysis

Growth Hormone Axis

Figure 12A

Alignment of Human, Rat, and Bovine SST Genomic DNA Sequences

| | | | | | |
|---|---|---|---|---|---|
| Human | ---------- | ---------- | ---------- | ---------- | ---------- |
| Rat | ---------- | ---------- | ---------- | ---------- | ---------- |
| Bovine | TGGCACTCCTTCTCT | TAGCTTGCAGACACA | AAAGGAAAAGCTGAC | AACTAATCAAGCCAT | TCGGTACACCTCCCA GTCCCTTCTGCCTCT -1498 |
| Human | ---------- | ---------- | ---------- | ---------- | ---------- |
| Rat | ---------- | ---------- | ---------- | ---------- | ---------- |
| Bovine | TAACGCTGTCTTGGT | CTAGTATAGAGAATA | CATATGTGATGCCTG | GC-GGAGACAGGGTT | AGTCATGTTCTCTGC TTCACTTGGTTTCTG -1408 |
| Human | ---------- | ---------- | ---------- | ---------- | ---------- |
| Rat | ---------- | ---------- | ---------- | ---------- | ---------- |
| Bovine | TGGAAATCAGTAATT | TTTTTCAGCTTTTAT | GAGCTTGGGAGCTTAT | AAACTGTAAGTCTCA | TAAGAGCCTGCAGGG TTCATCTGGCCCTTC -1318 |
| Human | ---------- | ---------- | ---------- | ---------- | ---------- |
| Rat | ---------- | ---------- | ---------- | ---------- | ---------- |
| Bovine | CCTGATAAGGAATTA | TTTCATGGAGGAGAA | AAAAAAAAGGAAAA | AAGCTGCCAGAACTC | TGATCAGAGATAGCTG ACATC-AACCAGACC -1228 |
| Human | ------GAATTCAA | GGACAGGTTTTCTTA | AACTTTCTTTGTTTC | TAGGAGATCAGGCAG | AGCTGAATTTAACCA AGAATCTTTTGATCC -1149 |
| Rat | ---------- | ---------- | ---------- | ---------- | ---------- |
| Bovine | ACAGCTAGAATT--A | GACCAGCATTTCTCA | AACTTTCTTTTTATT | TGTGAGGAGTGGG | AGAGTACTGT---CA ATGCTGTTTG---- -1147 |
| Human | TTTCCACATATAGAT | ATACAA-AGTGGTCA | CATATGTTCTGGGAG | TTCCTAGACCT-TAT | ATGTCTAAACTGGGG CTTCCTGACATAAAA -1060 |
| Rat | ---------- | ---------- | ---------- | ---------- | ---------- |
| Bovine | ------CACAGAAAC | ATACAA-AATGGTCA | CACATGTTCAGGGGG | TTCCTGGACTTCTGT | ATGTCCAGACTGGGA GTCCCTGATCCAGAA -1063 |
| Human | CTATGCTTACCGG-C | AGGAATCTGTTAGAA | AACTCAGAGCTCAGT | AGAAGGAACACTGGC | TTTGGAATGTGGAGG TCTGGTTTGCTCAA -971 |
| Rat | ---------- | ---------- | ---------- | ---------- | ---------- |
| Bovine | CTGCTACTACTAGTC | AGGAACCTATTAGGA | AACTCAAAT-TGAGT | GAAAAGAACCCTGGC | CTTGAAGTGTGGAGG ACTGGTCCTGCCCC -974 |
| Human | AG-TGTGCAGTATGT | GAAGGAGAACAATTT | ACTGACCATTACTCT | GCCTTACTGATTCAA | ATTCTGAGGTTTATT GAATAATTTCTTAGA -882 |
| Rat | ---------- | ---------- | ---------- | ---------- | ---------- |
| Bovine | AGCTGTGCACTATGT | GAGTCAGAGTATTTC | ATTGCCCATT-CTAG | GC-TCAATGACTCAA | ACTCTGGGGTTTAGT AGATGGTTCTGAGA -885 |
| Human | TTGCCTTCCAGCTCT | AAATTCTCAGCACC | AAAATGAAGTCCATT | TCAATCTCTCTCTCT | CTCTTTCCCTCCCGT ACATATACACACACT -792 |
| Rat | ---------- | ---------- | ---------- | ---------- | ---------- |
| Bovine | TTTCTTTCTAGTTCC | AAGTTTCA-AGGACA | AAAATTAAATTAATT | TT------TCT | TTTTTTCCTT------ -----TAG---CAGT -819 |

Figure 12B

```
Human   CATACATATATATGG TCACAATAGAAAGGC AGGTAGATCAGAAGT CT--CAGTTGCTGAG AAAGAGGGAGGGAGG GTGAGCCAGAG-TAC   -705
Rat     --------------- --------------- --------------- --------------- --------------- ---------------   -729
Bovine  TTTTGCAGGGGAGGG TAACGGTGGAAAGGC AGGTAGACTAAAAGT GTTTCAGCTGCTGAG AAAGAGGGATGGTGG GTGAACTTAAGGTAC Human   TT-CTCCCCCATTGT AGAGAAAAGTGAAGT TCTTTTTAGAGCCCCG TTACATCTT----C AAGGCCTTTTAT-GA GATAATGGAGGAAAT   -622
Rat     --------------- --------------- --------------- --------------- --------------- ---------------   -647
Bovine  TTTCTTCTTCCATTAT A---AGAAGTGAAGT TCTTTCAGAGCCTCA TGACTTCTTATCTAC AAGACTTTCACAGA GATAATGGAG-----

Human   AAAGAGGGCTCAGTC CTTCTACCGTCCATA TTTCATTCTCAAATC TGTTATTAGAGGAAT GATTCTGATCTCCAC CTAC-----------   -543
Rat     --------------- --------------- --------------- --------------- ---GAAGTGGAC---  CAGC-----------   -529
Bovine  AAAGATGATTCAATC TTTCCGAAATCCACA TTCCATTTTCAAATC TGTTCTTAGAGGAAT GCT-CTGACATGCAT TGTCACGAGGAATGC   -558

Human   -CAT-ACACATGC-- CCTGTTGCTTGTTGG GCCTTA--CA----- ----CTAAAAATGTT AGAGTATGATGACAG ATGGAGTTGTCTGGG   -469
Rat     -CGA-ATAG------ CTTTAAGCACCCTTG CACATA--CA----- ----CACGACCGTT A-AGCATGATGGCAA GTCCAGTAATCTGAG   -460
Bovine  TCGTGACAGTCTCCA CTTGTTACACTCTCA TACTTTTGCATTTGC CTCCTAAAAATGTT TGAGTATGATGCTGG ATAGAGTGGTCTG-G   -469

Human   TACATTT---GTGT GCATTTAAGGGTGAT AGTGTATTTGCTCTT TTGAGCCTCTGTTTG TGTGTAATTGAGTGT                   -383
Rat     TACATTGACAGTAC CCAACTGTGTGTGCT GATGTATT-GCTGGC CAAGGA-CTGAAGGA T------CTCAGT-- -----AATAATCAT    -385
Bovine  TATATTTATGGGCAT GCAGCTAGGTGTGCT GGCTCATTTGCTTCT GCAGAGGCTGAGTGT TTGAGTGTGT----- -----CATTGAATGT   -387

Human   GCATGTGTGGGAGTG AAATTGTGGAATGTG TATGCTCATAGCACT GAGTGAAAATAAAAG ATTGTATAAATCGTG GGGCAT--GTGGAAT   -295
Rat     GCACCTATGTG-GCG GAAATATGGATATG CATGTCGA---CACT GAGTGAAGGCAA--G ATTATTGTCTCTGTG TGGCGT--GGAGAAT   -303
Bovine  GCACATGTATGAGTG AGACTATGGAATGTG TATGTGCATAGCACT GAGTGAATATAAAAA ATTGTGTAGATGGAG TGACATATGTGGCAT   -297

Human   TGTGTGTGCCTGTGC GTGTGCAGTATTTTT TTTTTTTTAAG---- -------TAAGCCACT TTAGATCTTGTCACC TCCCCTGTCTTCTGT   -215
Rat     TTCATGTGCCTGTGT GGGTGCAGGCTTTCT TTTTCTTCAAAAAAA AAAAAATAAACCACT TTAGATCGTGTCGCC TCCCCTCACTTCTTT   -213
Bovine  CGCGTGGGCCTGTGC ATGTACAGGATTTAT TTTTTTTAA------ -------TAAGCTACT TTGATTGTGCAGCC TCCTCTCACTTCTGT   -218

Human   GATTGATTTGCGAG GCTAATGGTGCGTAA AAGGGCTGGTGAGAT CTGGGGGCGCGCCTCCT AGCCTGACGTCAGAG AGAGAGTTAAAACA   -125
Rat     GATTGATTTGCGAG GCTAATGGTGCGTAA AAGCACTGGTGAGAT CTGGGGGGCGCCTCCT TGGCTGACGTCAGAG AGAGAGTTAAAA-A   -124
Bovine  GATTGATTTCACGAG GGTAATGGTGCGTAA AACCGCTGGTGAGAT CTGGGGGGCGCCTCCT CGTCTGACGTCAGAG AGAGAGTTAAAA-A   -129
                                                                              CRE              TATA-BOX Human   GAGGGAGACGGTTGA GAGCACACAAGCGC TTTAGGAGCGA---G GTTC-GGAGCCATCG CTGCTGCCTGCTGAT CCGCGCCTAGAGTTT    -39
Rat     G-GGGAGACCGTGGA GAGCTCGATAGCGGC TGAAGGAGAC----G CTACTGGAGTCGTCT CTGCTGCCTGCGGAC CTGCGTCTAGAC--T   -41
Bovine  GGGGGAGACGGAGGA GAGCACACAAGCTGC TTTAGGAGAGGCAAG GTTC--GAGCCGTCG CTGCTGCCTGC-GAT CAGCTCCTAGAGTTT   -42
```

Figure 12C

```
                                                                                                                                    49
Human    GACCAGCCACTCTCC AGCTCGGCTTT-C-G CGGC-GCCGAGATGC TGTCCTGCGCCTCC AGTGCGCGCTGGCTG CGTGTCCTCATGTCC    49
Rat      GACCCACCGCGCTCA AGCTCGGCTGT-CTG AGGCAGGGGAGATGC TGTCCTGCCGTCTC AGTGCGCGCTGGGCCG GCTCTCATGTCC     49
Bovine   GACCAACCGCACTCT AGCTCGGCTTCGCCG CCGCGCCGAGATGC TGTCCTGCGCCTCC AGTGCGCGCTGGCCG CCTCTCCATGTCC
                                                                                              EXON 1

Human    TGGCCC-GGGCTGTG TCACCGGCGCTCCT CGGACCCCAGACTCC GTCAGTTTCTGCAGA AGTCCCTGGCTGCTG CCGCGGGGAAGCAGG   139
Rat      TGGCTTGGGCGGTG  TCACCGGGGCGCCCT CGGACCCCAGACTCC GTCAGTTTCTGCAGA AGTTCTGGCGGCTG  CCACCGGGGAAACAGG  139
Bovine   TGGCTCTTGGCGGTG TCACCGGCGCGCCCT CGGATCCCGGCTCC  GTCAGTTTCTGCAGA AATCCCTGGCTGCTG CGCTGGCAAGCAGG   139
                                         CRE Human    TAAGGAGACTCCCTC GAC------GTCTC  C-----CGGATTCTC CAGCCCTCCC-TAAG CCTTGCTCCTGCCCC  ATTGGTTTGGACGTA  216
Rat      TAAGGAAATGGCTGG  GACTC----GTCCC  CTTTG-CGAATTCCC CGGCCTTCCCCTTAG TCTTGCTGTAGCCCC  --TG------CGAC   214
Bovine   TAAGGAGACTCCCTT  GACGTCTTCTTTCCC CTCACCCGAATCCTC TAACTTTCCC--TCG CCTTGCCCCTGCTCC  CTTGGGT-GAATTTG  226

Human    AGGGATGCTCAGTCC  TTCTAAAGAGTTTTG GTGC-TTTTCTGGGT CCCTCAGCTCCCGAA GCTCTTGAGAAAACT ATCAAAGGCTAGAAT   305
Rat      AGG------TG--TTT T-----AGCG----G GCGC-TTCTCAGAGT CCTCAGC-CCCTGA  GCTCCAGGGAAACT  TTTGAAGTCTAGGGT   286
Bovine   AGG------TGC-TCC C-----ACAGTGCTG GTGCCTTTTCTGGGT CCCTTAGCCACCAAA GCTCTCGGGAAAACT  TTCAAAGTCCAGAAT  305

Human    CCCCTTCTAACTCTT  TTTTTCCCCCAT--- GATAAGCGCAGTCGG TCACAGTTCAGGTGA GTTCTTACTTGGCAT TCAAGAAAATTACAA    392
Rat      CCGCT-CTTACTCGT  T-----CCAGAATT- GATCGGCGCTGGTGG GTCCCCCTTCGCTT  GTCCAGGAAAATTCCGA                  370
Bovine   ACCTTTTTACCTTTT  TTTTTTCT-TCCC   GATCAGCCAGTAGG  TCACAGTTCAGGTGA GTTCTG--T-GGCTT TCAAGACAATTCCAA    392

Human    AATCTGGTAGTTGT   CTGGGCACGAAGCGA CAATGGCGTCTATCC CTGGTGCTGACCCTG GGAAGCGCTGACCCA  GGTGCTGAAAC-GCA   481
Rat      AAGCCTGCAAGA---  --GAGCGGGAGAGA  C--TGAGCTCTATCC CTGGTACTGGCACGA GGGTT-GCTGACCCA  GGTGCTGAAA------  447
Bovine   GACCTTGGTTAA---  CTGAGCTCGAAGGGA TAATGGCATCTCTCC CGGGTACTGACCGCG GGAGGTGCTGACCCA  GGTGCTGAAAGCGCG   479

Human    GACCTCGAAGCTGC   TACCTCTTAGCGTAC CTCACTTCCAAACGT CGGGACTAGG-CAA  AGGGCAATCTAAAG  ACCGAACGCCGTATG   570
Rat      -------------    -------------   ------AAAAAT    CCGG-----CAA    -G----A-ACTCAG  TCC------ATG      475
Bovine   GACCTCGAAGCGGC   TAGGC-----AGTAC CTCCCCCCATGCAG  CGGGACTAGGGGCTA AAGGACACTGTACAG CCAGAACACAACATG   564

Human    TTTGAGATTGTGAGA  AGCCTCGTTCCCCTA CAGTTTACTTGGTA  AAAATGGTAA-AACA  ATTCTACTTTGTAGC  TCGTGATGTGAAAAT  659
Rat      GTCCATTTCGTG---  -------TCTCATA  AAG---G------- -AAAATGG-------  ----------AGC   TGCT------------  512
Bovine   TTTACGGTTGCAAA   GGTCTCATTCCCTAA AAGT-GGCTTAGTA  AAACGGTAAGAACA   ATTCTAGTTTGTAGC TCATGATGTGGACAT  653

Human    TGAATTAAACTGTTG  GCACACACTTTATCT TACCAGAACGGTCTT TATGTGTGTGTGTGT GTGTGTGTGTGTGTT TGTGCGTGTGTGTGT   749
Rat      -----CAAACTATTG  GCATAC----TATAT TTACAAAACGA-CTT CCTATCA-TCCATG- GTTTCTGTGTGTTT  AAGGCATAGCACTTT   590
Bovine   TGAGCTAATCTATTG  GCTTATGTTTCACCT TTGCAAAACTAACAA TCTATTT---CCTTT CTTTGTGTGTGTTT  AAACC-TA-CAGAAG  738
```

Figure 12D

```
Human  GTGTGTCTGTGTGTT AAGTCTACAGGGACA GAAAGGTTGCAGAAA CATTTGAGCTCTTAA AGCCTTTTTGTGTAA CTTGGTAATTATAGC  839
Rat    CTGA----------- AAGACTTT--GGGT- -------TTGAGGAA- ------GCTTTTTT --CCCTGT-GCATAA TCTAGTGAATATAGC  648
Bovine CAG------------ AAAACT--------- -------TGCAGAAA CATTTGAGTTTTTAA AGCTTCTTTGTGTAA TTTTGTGGCTGTAGC  800

Human  AACTATCCTTATTTT TATA--TCCTTGATT GATTTTAAATGTGAC AAAAAATGCGCAGCT GTAAAAACTGGATTT TGTGTGTGACCAAAT  927
Rat    AGCCATCCATATT-- --------------- --------------- --------A---CT GTGGAAACTTGGTTT TGAAT--GATTAAAT  692
Bovine AACAGCCCTTGTTTT TTTACATCCTTAACT GATTTTAAGTGTTAC AAAAAGTCCACAGCT GGGAAAATTGGGGTT TGGTTGTGTTAAAC   890

Human  CTGTTCTTTAATTTA GGCTTTTCAAATTTT TTCCATTGTCCTCCC CACTT-CTCTTTTCT CTTTTTCTATC--CC TTCTGCCCTATACAG  1015
Rat    CT------TA----- ---TTTTCAAA---- --CCGCATTTCTCCC TTTCTCCATTCCCC CTTTTGCTCTC--CT CCCTGCCTATCCAG  760
Bovine CTGTATTTCAAGCCA AGCTCTCTTCGGTTT TCTTCTTCACCATCC TCATTTTCATCCTCT TTCCTTCTGTCTTCC TTCCACCCATGCAG  980

Human  GAACTGGCCAAGTAC TTCTTGGCAGAGCTG CTGTCTGAACCCAAC CAGACGGAGAATGAT GCCCTGGAACCTGAA GATCTGTCCCAGGCT  1105
Rat    GAACTGGCCAAGTAC TTCTTGGCAGAACTG CTGTCTGAGCCCAAC CAGACAGAGAACGAT GCCCTGGAGCCTGAG GATTTGCCCAGGCA   850
Bovine GAACTGGCCAAGTAC TTCTTGGCAGAGCTG CTGTCTGAACCCAAC CAGACAGAGATTGAT GCCCTGGAGCCTGAA GATTTGTCCCAGGCT  1070
                                                    EXON 2

Human  GCTGAGCAGGATGAA ATGAGGCTTCAGCTG CAGAGATCTGCTAAC TCAAACCCGGCTATG GCACCCCGAGAACGC AAAGCTGGCTGCAAG  1195
Rat    GCTGAGCAGGACGAG ATGAGGCTGGAGCTG CAGAGGTCTGCCAAC TCGAACCCAGCCATG GCACCCCGGGAACGC AAAGCTGGCTGCAAG   940
Bovine GCTGAGCAGGATGAA ATGAGGCTGGAGCTG CAGAGATCTGCTAAC TCAAACCCGGCCATG GCACCCCGAGAACGC AAAGCTGGCTGCAAG  1160

Human  AATTTCTTCTGGAAG ACTTTCACATCCTGT TAGCTTTCTTAACTA GTATTGTCCATATCA GACCTCTGATCCCTC GCCCCACACCCCAT  1285
Rat    AACTTCTTCTGGAAG ACATTCACATCCTGT TAGCTTT---AATA TTGTTGTCTCAGCCA GACCTCTGATCCCTC TCCTGCAAATCCCAT  1026
Bovine AATTTCTTCTGGAAG ACTTTCACATCCTGT TAACTTTATTAATGA TTGTTGCCCATATAA GACCTCTGATTCCTC TTC-CCAAACCCCTT  1250

Human  CTCTCTTCCCTAAT- ---------CCTCC AAGTCTTCAGCGAGA CCCTTGCATTAGAGA CTGAAAAC-GTAAAT ACAAAATAAAATTAT  1364
Rat    ATCTCTTCCTTAACT CCCAGCCCCCCCCCC CAATGCTCAACTAGA CCCT-GCGTTAGAAA TTGAAGACTGTAATT ACAAAATGTAATTAT  1115
Bovine CTCACCTCCCTAAT- ---------CCCTC CAATCCTCAATAAGA CCCTCGTGTTAGAAA TTGAAGACTGTAAAT ACAAAATAAAATTAT  1239

Human  GGTGAAATTATGAAA AATGTGAATTTGGTT TCTATTGAGTAAATC TTTTTGTTCAATAAT ACATAATAAGCT     1436
Rat    GGTGAAATTATG--- --------------- --------------- --------------- -----------     1127
Bovine GG-GAAATTATG--- --------------- --------------- --------------- -----------     1340
```

*Bold: Regulatory Elements.
*Bold nucleotides in boxes: Positions of SNPs (wild-type SNP shown).
*Underlined nucleotides: Exon sequences and Regulatory Element sequences.

Figure 13
Bovine SST Novel SNP Panel

| Animal | Breed | C126T | C157T | T244C | C575T | G981A |
|---|---|---|---|---|---|---|
| A2 | A | CC | CC | TT | CC | GG |
| A4 | A | CC | CC | TT | CC | GG |
| A5 | A | CC | CC | TT | CC | GG |
| A7 | A | CC | CC | TT | CC | GG |
| A8 | A | CC | CC | TT | CC | GG |
| A10 | A | CC | CC | TT | CC | GG |
| A11 | A | CC | CC | TT | CC | GG |
| B1 | A | CC | CC | TT | CC | GG |
| B2 | A | CC | CC | TT | CC | GG |
| B4 | A | CC | CC | TT | CC | GG |
| B8 | A | CC | CC | TT | CC | GG |
| B11 | A | CC | CC | TT | CC | GG |
| B12 | A | CC | CC | TT | CC | GG |
| C4 | A | CC | CC | TT | CC | GA |
| C8 | A | CC | CC | TT | CC | GG |
| C9 | A | CC | CC | TT | CC | GG |
| D1 | A | CC | CT | TT | CC | GA |
| D5 | A | CC | CC | TT | CC | GG |
| D9 | A | CC | CC | TT | CC | GG |
| D10 | A | CC | CC | TT | CC | GG |
| G2 | A | CC | CC | TT | CC | GG |
| G3 | A | TT | CC | CC | TT | GG |
| G8 | A | CC | CC | TT | CC | GG |

| Animal | Breed | C126T | C157T | T244C | C575T | G981A |
|---|---|---|---|---|---|---|
| B6 | B | CC | CT | CC | TT | GG |
| B10 | B | TT | CC | CC | TT | GG |
| C3 | B | CT | CC | TC | TT | GG |
| C6 | B | TT | CC | CC | TT | GG |
| C11 | B | TT | CC | CC | TT | GG |
| D2 | B | CT | CC | CC | TT | GG |
| D4 | B | TT | CC | CC | TT | GG |
| D7 | B | TT | CC | CC | CT | GG |
| D12 | B | CC | CC | TT | CC | GG |
| E3 | B | TT | CC | CC | TT | GG |
| E5 | B | CC | CC | TC | TT | GG |
| E7 | B | CT | CT | CC | TT | GG |
| E8 | B | CT | CT | CC | TT | GG |
| E10 | B | CT | CC | TC | TT | GG |
| E11 | B | TT | CC | CC | TT | GG |
| F1 | B | TT | CC | CC | TT | GG |
| F2 | B | CT | CT | CC | CT | GG |
| F4 | B | CC | CC | TC | TT | GG |
| F6 | B | CT | CT | CC | TT | GG |
| G4 | B | CC | CC | TT | CC | GG |
| G6 | B | CT | CC | CC | TT | GG |

* Angus (A)
* Brahman (B)

Figure 14A

```
-1587                TGGCACTCCT  TCTCTTAGCT  TGCAGACACA  AAAGGAAAAG
-1547   CTGACAACTA   ATCAAGCCAT  TCGGTACACC  TCCCAGTCCC  TTCTGCCTCT
-1497   TAACGCTGTC   TTGGTCTAGT  ATAGAGAATA  CATATGTGAT  GCCTGGCTGG
-1447   AGACAGGGTT   AGTCATGTTC  TCTGCTTCAC  TTGGTTTCTG  TGGAAATCAG
-1397   TAATTTTTTT   CAGCTTTTAT  GAGCTTGGAG  CTTATAAACT  GTAAGTCTCA
-1347   TAAGAGCCTG   CAGGGTTCAT  CTGGCCCTTC  CCTGATAAGG  AATTATTTCA
-1297   TGGAGGAGAA   AAAAAAAAAG  GAAAAAGCT   GCCAGAACTC  TGATCAGGAT
-1247   AGCTGACATC   TAACCAGACC  ACAGCTAGAA  TTAGACCAGC  ATTTCTCAAA
-1197   CTTTCTTTTT   ATTTGTGAGA  GGAGTGGGAG  AGTACTGTCA  ATGCTGTTTT
-1147   GCACAGAAAC   ATACAATAAT  GGTCACACAT  GTTCAGGGGG  TTCCTGGACT
-1097   TCTGTATGTC   CAGACTGGGA  GTCCTGATC   CAGAACTGCT  ACTACTAGTC
-1047   AGGAACCTAT   TAGGAAACTC  AAATTGAGTG  AAAAGAACCC  TGGCCTTGAA
-997    GTGTGGAGGA   CTGGTCCTGG  CCCCAGCTGT  GCACTATGTG  AGTCAGAGTA
-947    TTTCATTGCC   CATTTCTAGG  CTCAATGACT  CAAACTCTGG  GGTTTAGTAG
-897    ATGGTTTCTG   AGATTTCTTT  CTAGTTCCAA  GTTTCAAGGA  CAAAAATTAA
-847    ATTAATTTTT   CTTTTTTTCC  TTTAGCAGTT  TTTGCAGGGG  AGGGTAACGG
-797    TGGAAAGGCA   GGTAGACTAA  AAGTGTTTCA  GCTGCTGAGA  AAGAGGGATG
-747    GTGGGTGAAC   TTAAGGTACT  TTCTTCTCCA  TTATAAGAAG  TGAAGTTCTT
-697    TCAGAGCCTC   ATGACTTCTT  ATCTACAAGA  CTTTTCACAG  AGATAATGGA
-647    GAAAGATGAT   TCAATCTTTC  CGAAATCCAC  ATTCCATTTT  CAAATCTGTT
-597    CTTAGAGGAA   TGCTCTGACA  TGCATTGTCA  CGAGGAATGC  TCGTGACAGT
-547    CTCCACTTGT   TACACTCTCA  TACTTTTGCA  TTTGCCTCTC  CTAAAATGTT
-497    TGAGTATGAT   GCTGGATAGA  GTGGTCTGGT  ATATTTATGG  GCATGCAGCT
-447    AGGTGTGCTG   GCTCATTTGC  TTCTGCAGAG  GCTGAGTGTT  TGAGTGTGTG
-397    TCATTAATG    TGCACATGTA  TGAGTGAGAC  TATGGAATGT  GTATGTGCAT
-347    AGCACTGAGT   GAATATAAAA  AATTGTGTAG  ATGGAGTGAC  ATATGTGGCA
-297    TCGCGTGGGC   CTGTGCATGT  ACAGGATTTA  TTTTTTTTTA  ATAAGCTACT
                                                        CAAT-BOX
-247    TTTGATTGTG   CAGCCTCCTC  TCACTTCTGT  GATTGATTTC  ACGAGGGTAA
                                                        CRE
-197    TGGTGCGTAA   AACCGCTGGT  GAGATCTGGG  GGCGCCTCCT  CGTCTGACGT
                     TATA-BOX
-147    CAGAGAGAGA   GTTTAAAAAG  GGGGAGACGG  AGGAGAGCAC  ACAAGCTGCT
-97     TTAGGAGAGG   CAAGGTTCGA  GCCGTCGCTG  CTGCCTGCGA  TCAGCTCCTA
-47     GAGTTTGACC   AACCGCACTC  TAGCTCGGCT  TCGCCGCCGC  CGCCGAGATG
4       CTGTCCTGCC   GCCTCCAGTG  CGCGCTGGCC  GCGCTCTCCA  TCGTCCTGGC
54      TCTTGGCGGT   GTCACCGGCG  CGCCCTCGGA  TCCCCGGCTC  CGTCAGTTTC
104     TGCAGAAATC   CCTGGCTGCT  GCCGCTGGCA  AGCAGGTAAG  GAGACTCCCT
        CRE
154     TGACGTCTTC   TTTCCCCTCA  CCCGAATCCC  CTAACTTTCC  CTCGCCTTGC
204     CCCTGCTCCC   TTGGGTGAAT  TTGAGGTGCT  CCCACAGTGC  TGGTGCCTTT
254     TCTGGGTCCC   TTAGCCACCA  AAGCTCTCGG  GAAAACTTTC  AAAGTCCAGA
304     ATACCTTTTT   ACCTTTTTTT  TTTTTCTTTC  CCGATCAGCG  CAGTAGGTCA
354     CAGTTCAGGT   GAGTTCTGTG  GCTTTCAAGA  CAATTCCAAG  ACCTTGGTTA
404     ACTGAGCTCG   AAGGGATAAT  GGCATCTCTC  CCGGGTACTG  ACCGCGGGAG
454     GTGCTGACCC   AGGTGCTGAA  AGCGCGGACC  TCTGAAGCGG  CTAGGCAGTA
504     CCTCCCTCCC   ATGCAGCGGG  ACTAGGGCT   AAAGGACACT  GTACAGCCAG
554     AACACAACAT   GTTTACGGTT  GCGAAAGGTC  TCATTCCTA   AAAGGTGGCT
604     TAGTAAAAAC   GGTAAGAACA  ATTCTAGTTT  GTAGCTCATG  ATGTGGACAT
654     TGAGCTAATC   TATTGGCTTA  TGTTTCACCT  TTGCAAAACT  AACAATCTAT
```

Figure 14B

| | | | | | |
|---|---|---|---|---|---|
| 704 | TTCCTTTCTT | TGTGTGTGTT | TTAAACCTAC | AGAAGCAGAA | AACTTGCAGA |
| 754 | AACATTTGAG | TTTTTAAAGC | TTCTTTGTGT | AATTTTGTGG | CTGTAGCAAC |
| 804 | AGCCCTTGTT | TTTTTACATC | CTTAACTGAT | TTTAAGTGTT | ACAAAAAGTC |
| 854 | CACAGCTGGG | AAAATTGGGG | TTTGGTTGTG | GTTAAACCTG | TATTTCAAGC |
| 904 | CAAGCTCTTC | TGGTTTTTCT | TCTTCACCAT | CCTCATTTTC | ATCCTCTTTC |
| 954 | CTTCTGTCTT | CCTTCCACCC | CATGCAGGAA | CTGGCCAAGT | ACTTCTTGGC |
| 1004 | AGAGCTGCTG | TCTGAACCCA | ACCAGACAGA | GATTGATGCC | CTGGAGCCTG |
| 1054 | AAGATTTGTC | CCAGGCTGCT | GAGCAGGATG | AAATGAGGCT | GGAGCTGCAG |
| 1104 | AGATCTGCTA | ACTCAAACCC | GGCCATGGCA | CCCCGAGAAC | GCAAAGCTGG |
| 1154 | CTGCAAGAAT | TTCTTCTGGA | AGACTTTCAC | ATCCTGTTAA | CTTTATTAAT |
| 1204 | GATTGTTGCC | CATATAAGAC | CTCTGATTCC | TCTTCTCCAA | ACCCCTTCTC |
| 1254 | ACCTCCCTAA | TCCCTCCAAT | CCTCAATAAG | ACCCTCGTGT | TAGAAATTGA |
| 1304 | AGACTGTAAA | TACAAAATAA | AATTATGGGA | AATTATG | |

*Bold: Regulatory Elements.
*Bold nucleotides in boxes: Positions of SNPs (wild-type SNP shown).
*Underlined nucleotides: Exon sequences and Regulatory Element sequences.

SEQUENCE LISTING

<160> NUMBER OF SEQ ID NOS: 27

<210> SEQ ID NO 1
<211> LENGTH: 1545
<212> TYPE: DNA
<213> ORGANISM: Bovine SST gene

<400> SEQUENCE: 1

```
tggcactcct tctcttagct tgcagacaca aaaggaaaag ctgacaacta atcaagccat      60
tcggtacacc tcccagtccc ttctgcctct taacgctgtc ttggtctagt atagagaata     120
catatgtgat gcctggctgg agacagggtt agtcatgttc tctgcttcac ttggtttctg     180
tggaaatcag taatttttt cagcttttat gagcttggag cttataaact gtaagtctca     240
taagagcctg cagggttcat ctggcccttc cctgataagg aattatttca tggaggagaa     300
aaaaaaaaag gaaaaaagct gccagaactc tgatcaggat agctgacatc taaccagacc     360
acagctagaa ttgaccagca tttctcaaac tttcttttta tttgtgagag gagtgggaga     420
gtactgtcaa tgctgttttg cacagaaaca tacaataatg gtcacacatg ttcaggggt      480
tcctggactt ctgtatgtcc agactgggag tccctgatcc agaactgcta ctactagtca     540
ggaacctatt aggaaactca aattgagtga aaagaaccct ggccttgaag tgtggaggac     600
tggtcctggc cccagctgtg cactatgtga gtcagagtat ttcattgccc atttctaggc     660
tcaatgactc aaactctggg gtttagtaga tggtttctga gatttctttc tagttccaag     720
tttcaaggac aaaaattaaa ttaattttc ttttttttcct ttagcagttt ttgcagggga     780
gggtaacggt ggaaaggcag gtagactaaa agtgtttcag ctgctgagaa agagggatgg     840
tgggtgaact taaggtactt tcttctccat tataagaagt gaagttcttt cagagcctca     900
tgacttctta tctacaagac ttttcacaga gataatggag aaagatgatt caatctttcc     960
gaaatccaca ttccattttc aaatctgttc ttagaggaat gctctgacat gcattgtcac    1020
gaggaatgct cgtgacagtc tccacttgtt acactctcat acttttgcat ttgcctctcc    1080
taaaatgttt gagtatgatg ctggatagag tggtctggta tatttatggg catgcagcta    1140
ggtgtgctgg ctcatttgct tctgcagagg ctgagtgttt gagtgtgtgt cattgaatgt    1200
gcacatgtat gagtgagact atggaatgtg tatgtgcata gcactgagtg aatataaaaa    1260
attgtgtaga tggagtgaca tatgtggcat cgcgtgggcc tgtgcatgta caggatttat    1320
tttttttaa taagctactt ttgattgtgc agcctcctct cacttctgtg attgatttca    1380
cgagggtaat ggtgcgtaaa accgctggtg agatctgggg gcgcctcctc gtctgacgtc    1440
agagagagag tttaaaaagg gggagacgga ggagagcaca caagctgctt taggagaggc    1500
aaggttcgag ccgtcgctgc tgcctgcgat cagctcctag agttt                    1545
```

<210> SEQ ID NO 2
<211> LENGTH: 2665
<212> TYPE: DNA
<213> ORGANISM: Human SST gene

<400> SEQUENCE: 2

```
gaattcaagg acaggttttc ttaaactttc tttgtttcta ggagatcagg cagagctgaa       60
```

-continued

```
tttaaccaag aatcttttga tcctttccac atatagatat acaatagtgg tcacatatgt    120
tctgggagtt cctagacctt atatgtctaa actggggctt cctgacataa aactatgctt    180
accggcagga atctgttaga aaactcagag ctcagtagaa ggaacactgg ctttggaatg    240
tggaggtctg gttttgctca aagtgtgcag tatgtgaagg agaacaattt actgaccatt    300
actctgcctt actgattcaa attctgaggt ttattgaata atttcttaga ttgccttcca    360
gctctaaatt tctcagcacc aaaatgaagt ccatttcaat ctctctctct ctctttccct    420
cccgtacata tacacacact catacatata tatggtcaca atagaaaggc aggtagatca    480
gaagtctcag ttgctgagaa agagggaggg agggtgagcc agagtacttc tcccccattg    540
tagagaaaag tgaagttctt ttagagcccc gttacatctt aaggccttt atgagataat     600 ggaggaaata aagagggctc agtccttcta ccgtccatat ttcattctca aatctgttat    660
tagaggaatg attctgatct ccacctacca tacacatgcc ctgttgcttg ttgggcctta    720
cactaaaatg ttagagtatg atgacagatg gagttgtctg ggtacatttg tgtgcattta    780
agggtgatag tgtatttgct cttttaagagc tgagtgtttg agcctctgtt tgtgtgtaat    840
tgagtgtgca tgtgtgggag tgaaattgtg gaatgtgtat gctcatagca ctgagtgaaa    900
ataaaagatt gtataaatcg tggggcatgt ggaattgtgt gtgcctgtgc gtgtgcagta    960 ttttttttt tttaagtaag ccactttaga tcttgtcacc tccctgtct tctgtgattg      1020 attttgcgag gctaatggtg cgtaaaaggg ctggtgagat ctgggggcgc ctcctagcct    1080
gacgtcagag agagagttta aaacagaggg agacggttga gagcacacaa gccgctttag    1140
gagcgaggtt cggagccatc gctgctgcct gctgatccgc gcctagagtt tgaccagcca    1200
ctctccagct cggctttcgc ggcgccgaga tgctgtcctg ccgcctccag tgcgcgctgg    1260
ctgcgctgtc catcgtcctg gccctgggct gtgtcaccgg cgctccctcg gaccccagac    1320
tccgtcagtt tctgcagaag tccctggctg ctgccgcggg gaagcaggta aggagactcc    1380
ctcgacgtct cccggattct ccagccctcc ctaagccttg ctcctgcccc attggtttgg    1440
acgtaaggga tgctcagtcc ttctaaagag ttttggtgct tttctgggtc cctcagctcc    1500
cgaagctctt gagaaaacta tcaaaggcta gaatccccctt ctaactcttt ttttccccca   1560
tgataagcgc agtcggtcac agttcaggtg agttcttact tggcattcaa gaaaattaca    1620
aaatctgggt agttgtctgg gcacgaagcg acaatggcgt ctatccctgg tgctgaccct    1680
gggaagcgct gacccaggtg ctgaaacgca gacctctgaa gctgctacct cttagcgtac    1740
ctcacttcca aacgtcggga ctagggcaaa ggggcaatct aaagaccgaa cgccgtatgt    1800
ttgagattgt gagaagcctc gttcccctac agttttactt ggtaaaaatg gtaaaacaat    1860
tctactttgt agctcgtgat gtgaaaattg aattaaactg ttggcacaca ctttatctta    1920
ccagaacggc ctttatgtgt gtgtgtgtgt gtgtgtgtgt gtttgtgcgt gtgtgtgtgt    1980
gtgtgtgtgt gttaagtcta cagggacaga aaggttgcag aaacatttga gctcttaaag    2040
cctttttgtg taacttggta attatagcaa ctatccttat ttttatatcc ttgattgatt    2100
ttaaatgtga caaaaaatgc gcagctgtaa aaactggatt ttgtgtgtga ccaaatctgt    2160
tctttaattt aggcttttca aattttttcc attgtcctcc ccactctct ttctctcttt     2220 ttctatccct tctgccctat acaggaactg gccaagtact tcttggcaga gctgctgtct    2280
gaacccaacc agacggagaa tgatgccctg gaacctgaag atctgtccca ggctgctgag    2340
caggatgaaa tgaggcttga gctgcagaga tctgctaact caaacccggc tatggcaccc    2400
```

```
cgagaacgca aagctggctg caagaatttc ttctggaaga ctttcacatc ctgttagctt    2460
tcttaactag tattgtccat atcagacctc tgatccctcg cccccacacc ccatctctct    2520
tccctaatcc tccaagtctt cagcgagacc cttgcattag aaactgaaaa ctgtaaatac    2580
aaaataaaat tatggtgaaa ttatgaaaaa tgtgaatttg gtttctattg agtaaatctt    2640
tttgttcaat aatacataat aagct                                         2665
```

<210> SEQ ID NO 3
<211> LENGTH: 1667
<212> TYPE: DNA
<213> ORGANISM: Rat SST gene

<400> SEQUENCE: 3

```
gaagtggacc agccgaatag ctttaagcac ccttgcacat acacacgacc gttaagcatg      60
atggcaagtc cagtaatctg agtacattga caggtaccca actgtgtgtg ctgatgtatt     120
gctggccaag gactgaagga tctcagtaat taatcatgca cctatgtggc ggaaatatgg     180
gatatgcatg tcgacactga gtgaaggcaa gattatttgg tctgtgtggc gtggagaatt     240
tcatgtgcct gtgtgggtgc aggctttctt tttcttcaaa aaaaaaaaaa taaaccactt     300
tagatcgtgt cgcctcccct cacttctttg attgattttg cgaggctaat ggtgcgtaaa     360
agcactggtg agatctgggg gcgcctcctt ggctgacgtc agagagagag tttaaaaagg     420
ggagaccgtg gagagctcga tagcggctga aggagacgct actggagtcg tctctgctgc     480
ctgcggacct cgtctagac tgacccaccg cgctcaagct cggctgtctg aggcagggga     540
gatgctgtcc tgccgtctcc agtgcgcgct ggccgcgctc tgcatcgtcc tggctttggg     600
cggtgtcacc ggggcgccct cggacccag actccgtcag tttctgcaga agtctctggc     660
ggctgccacc gggaaacagg taaggaaatg gctgggactc gtccccttg cgaattcccc     720 ggccttcccc ttagtcttgc tgtagcccct gcgacaggtg ttttagcggg cgcttctcag     780
agtcgctcag cccctgagct cccagggaaa cttttgaagt ctagggtccg ctcttactcg     840
ttccagaatt gatcggcgct ggtggtcacc ttgcaggtaa gttccccctt cgctttcagg     900
aaaattccga aagcctgcaa gagagcgggg agagactgag ctctatccct ggtactggca     960
cgagggttgc tgacccaggt gctgaaaaaa atccggcaa gaactcaggt ccatggtcca    1020
tttcgtgtct cataaaggaa aatggagctg ctcaaactat tggcatacta tatttacaaa    1080
acgacttcct atcatccatg gtttctctgt gtttttaaggc atagcacttt ctgaaagact    1140
tgggtttgag gaagcttttt tccctgtgca taatctagta aatatagcag ccatccatat    1200
tactgtggaa acttggtttt gaatgattaa atcttatttt caaaccgcat ttctcccttt    1260
ctcccattcc ccttttgct ctcctccctg ccctatccag gaactggcca agtacttctt    1320
ggcagaactg ctgtctgagc ccaaccagac agagaacgat gccctggagc tgaggatt     1380 gccccaggca gctgagcagg acgagatgag gctggagctg cagaggtctg ccaactcgaa    1440
cccagccatg gcaccccggg aacgcaaagc tggctgcaag aacttcttct ggaagacatt    1500
cacatcctgt tagctttaat attgttgtct cagccagacc tctgatccct ctcctgcaaa    1560
tcccatatct cttccttaac tcccagcccc cccccccaat gctcaactag accctgcgtt    1620
agaaattgaa gactgtaatt acaaaataaa attatggtga aattatg                1667
```

<210> SEQ ID NO 4
<211> LENGTH: 22
<212> TYPE: DNA
<213> ORGANISM: Artificial sequence -continued

```
<220> FEATURE:
<223> OTHER INFORMATION: Bovine SST primer

<400> SEQUENCE: 4
acttcttggc agagctgctg tc                                                  22

<210> SEQ ID NO 5
<211> LENGTH: 23
<212> TYPE: DNA
<213> ORGANISM: Artificial sequence
<220> FEATURE:
<223> OTHER INFORMATION: Bovine SST primer

<400> SEQUENCE: 5
acgagggtct tattgaggat tgg                                                 23

<210> SEQ ID NO 6
<211> LENGTH: 21
<212> TYPE: DNA
<213> ORGANISM: Artificial sequence
<220> FEATURE:
<223> OTHER INFORMATION: Bovine SST primer

<400> SEQUENCE: 6
cttattcata tcttgccagt t                                                   21

<210> SEQ ID NO 7
<211> LENGTH: 16
<212> TYPE: DNA
<213> ORGANISM: Artificial sequence
<220> FEATURE:
<223> OTHER INFORMATION: Bovine SST primer

<400> SEQUENCE: 7
gggagctttg tggtga                                                         16

<210> SEQ ID NO 8
<211> LENGTH: 27
<212> TYPE: DNA
<213> ORGANISM: Artificial sequence
<220> FEATURE:
<223> OTHER INFORMATION: Bovine SST primer

<400> SEQUENCE: 8
gcctggctgg agacagggtt agtcatg                                             27

<210> SEQ ID NO 9
<211> LENGTH: 23
<212> TYPE: DNA
<213> ORGANISM: Artificial sequence
<220> FEATURE:
<223> OTHER INFORMATION: Bovine SST primer

<400> SEQUENCE: 9
cagaaaccat ctactaaacc cca                                                 23

<210> SEQ ID NO 10
<211> LENGTH: 17
<212> TYPE: DNA
<213> ORGANISM: Artificial sequence
<220> FEATURE:
<223> OTHER INFORMATION: Bovine SST primer

<400> SEQUENCE: 10
taggagaggc aaggttc                                                        17
```

<210> SEQ ID NO 11
<211> LENGTH: 23
<212> TYPE: DNA
<213> ORGANISM: Artificial sequence
<220> FEATURE:
<223> OTHER INFORMATION: Bovine SST primer

<400> SEQUENCE: 11
ccaatagatt agctcaatgt cca                                             23

<210> SEQ ID NO 12
<211> LENGTH: 23
<212> TYPE: DNA
<213> ORGANISM: Artificial sequence
<220> FEATURE:
<223> OTHER INFORMATION: Bovine SST primer

<400> SEQUENCE: 12
gatccccggc tccgtcagtt tct                                             23

<210> SEQ ID NO 13
<211> LENGTH: 22
<212> TYPE: DNA
<213> ORGANISM: Artificial sequence
<220> FEATURE:
<223> OTHER INFORMATION: Bovine SST primer

<400> SEQUENCE: 13
cctgggacaa atcttcaggc tc                                              22

<210> SEQ ID NO 14
<211> LENGTH: 23
<212> TYPE: DNA
<213> ORGANISM: Artificial sequence
<220> FEATURE:
<223> OTHER INFORMATION: Bovine SST primer

<400> SEQUENCE: 14
tggacattga gctaatctat tgg                                             23

<210> SEQ ID NO 15
<211> LENGTH: 20
<212> TYPE: DNA
<213> ORGANISM: Artificial sequence
<220> FEATURE:
<223> OTHER INFORMATION: Bovine SST primer

<400> SEQUENCE: 15
ggagggatta gggaggtgag                                                 20

<210> SEQ ID NO 16
<211> LENGTH: 22
<212> TYPE: DNA
<213> ORGANISM: Artificial sequence
<220> FEATURE:
<223> OTHER INFORMATION: Bovine SST primer

<400> SEQUENCE: 16
cctggctgct gccgctggca ag                                              22

<210> SEQ ID NO 17
<211> LENGTH: 22
<212> TYPE: DNA
<213> ORGANISM: Artificial sequence
<220> FEATURE:
<223> OTHER INFORMATION: Bovine SST primer

```
<400> SEQUENCE: 17
cctggctgct gctgctggca ag                                              22

<210> SEQ ID NO 18
<211> LENGTH: 22
<212> TYPE: DNA
<213> ORGANISM: Artificial sequence
<220> FEATURE:
<223> OTHER INFORMATION: Bovine SST primer

<400> SEQUENCE: 18
ctcccttgac gtcttctttc cc                                              22

<210> SEQ ID NO 19
<211> LENGTH: 22
<212> TYPE: DNA
<213> ORGANISM: Artificial sequence
<220> FEATURE:
<223> OTHER INFORMATION: Bovine SST primer

<400> SEQUENCE: 19
ctcccttgat gtcttctttc cc                                              22

<210> SEQ ID NO 20
<211> LENGTH: 22
<212> TYPE: DNA
<213> ORGANISM: Artificial sequence
<220> FEATURE:
<223> OTHER INFORMATION: Bovine SST primer

<400> SEQUENCE: 20
cccacagtgc tggtgccttt tc                                              22

<210> SEQ ID NO 21
<211> LENGTH: 22
<212> TYPE: DNA
<213> ORGANISM: Artificial sequence
<220> FEATURE:
<223> OTHER INFORMATION: Bovine SST primer

<400> SEQUENCE: 21
cccacagtgc cggtgccttt tc                                              22

<210> SEQ ID NO 22
<211> LENGTH: 22
<212> TYPE: DNA
<213> ORGANISM: Artificial sequence
<220> FEATURE:
<223> OTHER INFORMATION: Bovine SST primer

<400> SEQUENCE: 22
gtttacggtt gcgaaaggtc tc                                              22

<210> SEQ ID NO 23
<211> LENGTH: 22
<212> TYPE: DNA
<213> ORGANISM: Artificial sequence
<220> FEATURE:
<223> OTHER INFORMATION: Bovine SST primer

<400> SEQUENCE: 23
gtttacggtt gtgaaaggtc tc                                              22

<210> SEQ ID NO 24
```

```
<211> LENGTH: 22
<212> TYPE: DNA
<213> ORGANISM: Artificial sequence
<220> FEATURE:
<223> OTHER INFORMATION: Bovine SST primer

<400> SEQUENCE: 24
ccccatgcag gaactggcca ag                                              22

<210> SEQ ID NO 25
<211> LENGTH: 22
<212> TYPE: DNA
<213> ORGANISM: Artificial sequence
<220> FEATURE:
<223> OTHER INFORMATION: Bovine SST primer

<400> SEQUENCE: 25
ccccatgcag aaactggcca ag                                              22

<210> SEQ ID NO 26
<211> LENGTH: 18
<212> TYPE: DNA
<213> ORGANISM: Artificial sequence
<220> FEATURE:
<223> OTHER INFORMATION: Bovine SST primer

<400> SEQUENCE: 26
aggtgctccc acagtgcc                                                   18

<210> SEQ ID NO 27
<211> LENGTH: 3883
<212> TYPE: DNA
<213> ORGANISM: Artificial sequence
<220> FEATURE:
<223> OTHER INFORMATION: Bovine SST gene

<400> SEQUENCE: 27
tggcactcct tctcttagct tgcagacaca aaaggaaaag ctgacaacta atcaagccat      60
tcggtacacc tcccagtccc ttctgcctct taacgctgtc ttggtctagt atagagaata    120
catatgtgat gcctggctgg agacagggtt agtcatgttc tctgcttcac ttggtttctg    180
tggaaatcag taattttttt cagcttttat gagcttggag cttataaact gtaagtctca    240
taagagcctg cagggttcat ctggcccttc cctgataagg aattatttca tggaggagaa    300
aaaaaaaaag gaaaaaagct gccagaactc tgatcaggat agctgacatc taaccagacc    360
acagctagaa ttgaccagca tttctcaaac tttcttttta tttgtgagag gagtgggaga    420
gtactgtcaa tgctgttttg cacagaaaca tacaataatg gtcacacatg ttcagggggt    480
tcctggactt ctgtatgtcc agactggagt ccctgatcc agaactgcta ctactagtca     540
ggaacctatt aggaaactca aattgagtga aagaaccct ggccttgaag tgtggaggac      600
tggtcctggc cccagctgtg cactatgtga gtcagagtat ttcattgccc atttctaggc    660
tcaatgactc aaactctggg gtttagtaga tggtttctga gatttctttc tagttccaag    720
tttcaaggac aaaaattaaa ttaattttc ttttttttcct ttagcagttt ttgcagggga     780
gggtaacggt ggaaaggcag gtagactaaa agtgtttcag ctgctgagaa agagggatgg    840
tgggtgaact taaggtactt tcttctccat tataagaagt gaagttcttt cagagcctca    900
tgacttctta tctacaagac ttttcacaga gataatggag aaagatgatt caatcttttcc   960 tggcactcct tctcttagct tgcagacaca aaaggaaaag ctgacaacta atcaagccat    1020
tcggtacacc tcccagtccc ttctgcctct taacgctgtc ttggtctagt atagagaata   1080
```

```
catatgtgat gcctggctgg agacagggtt agtcatgttc tctgcttcac ttggtttctg    1140
tggaaatcag taattttttt cagcttttat gagcttggag cttataaact gtaagtctca    1200
taagagcctg cagggttcat ctggcccttc cctgataagg aattatttca tggaggagaa    1260
aaaaaaaaag gaaaaaagct gccagaactc tgatcaggat agctgacatc taaccagacc    1320
acagctagaa ttagaccagc atttctcaaa ctttctttttt atttgtgaga ggagtgggag   1380
agtactgtca atgctgtttt gcacagaaac atacaataat ggtcacacat gttcagggg    1440
ttcctggact tctgtatgtc cagactggga gtccctgatc cagaactgct actactagtc   1500
aggaacctat taggaaactc aaattgagtg aaaagaaccc tggccttgaa gtgtggagga   1560
ctggtcctgg ccccagctgt gcactatgtg agtcagagta tttcattgcc catttctagg   1620
ctcaatgact caaactctgg ggtttagtag atggtttctg agatttcttt ctagttccaa   1680
gtttcaagga caaaaattaa attaattttt cttttttttcc tttagcagtt tttgcagggg  1740
agggtaacgg tggaaaggca ggtagactaa aagtgtttca gctgctgaga aagagggatg   1800
gtgggtgaac ttaaggtact ttcttctcca ttataagaag tgaagttctt tcagagcctc   1860
atgacttctt atctacaaga cttttcacag agataatgga gaaagatgat tcaatctttc   1920
cgaaatccac attccatttt caaatctgtt cttagaggaa tgctctgaca tgcattgtca   1980
cgaggaatgc tcgtgacagt ctccacttgt tacactctca tacttttgca tttgcctctc   2040
ctaaaatgtt tgagtatgat gctggataga gtggtctggt atatttatgg gcatgcagct   2100
aggtgtgctg gctcatttgc ttctgcagag gctgagtgtt tgagtgtgtg tcattgaatg   2160
tgcacatgta tgagtgagac tatggaatgt gtatgtgcat agcactgagt gaatataaaa   2220
aattgtgtag atggagtgac atatgtggca tcgcgtgggc ctgtgcatgt acaggattta   2280
tttttttta ataagctact tttgattgtg cagcctcctc tcacttctgt gattgatttc    2340
acgagggtaa tggtgcgtaa aaccgctggt gagatctggg ggcgcctcct cgtctgacgt   2400
cagagagaga gtttaaaaag ggggagacgg aggagagcac acaagctgct ttaggagagg   2460
caaggttcga gccgtcgctg ctgcctgcga tcagctccta gagtttgacc aaccgcactc   2520
tagctcggct tcgccgccgc cgccgagatg ctgtcctgcc gcctccagtg cgcgctggcc   2580
gcgctctcca tcgtcctggc tcttggcggt gtcaccggcg cgcccctcgga tccccggctc  2640
cgtcagtttc tgcagaaatc cctggctgct gccgctggca agcaggtaag gagactccct   2700
tgacgtcttc tttccctctca cccgaatccc ctaactttcc ctcgccttgc ccctgctccc   2760
ttgggtgaat ttgaggtgct cccacagtgc tggtgccttt tctgggtccc ttagccacca   2820
aagctctcgg gaaaactttc aaagtccaga ataccttttt acctttttt tttttctttc    2880
ccgatcagcg cagtaggtca cagttcaggt gagttctgtg gctttcaaga caattccaag   2940
accttggtta actgagctcg aagggataat ggcatctctc ccgggtactg accgcgggag   3000
gtgctgaccc aggtgctgaa agcgcggacc tctgaagcgg ctaggcagta cctccctccc   3060
atgcagcggg actaggggct aaaggacact gtacagccag aacacaacat gtttacggtt   3120
gcgaaaggtc tcattcccta aaaggtggct tagtaaaaac ggtaagaaca attctagttt   3180
gtagctcatg atgtggacat tgagctaatc tattggctta tgtttcacct ttgcaaaact   3240
aacaatctat ttcctttctt tgtgtgtgtt ttaaacctac agaagcagaa aacttgcaga   3300
aacatttgag ttttaaagc ttctttgtgt aattttgtgg ctgtagcaac agcccttgtt    3360
tttttacatc cttaactgat tttaagtgtt acaaaaagtc cacagctggg aaaattgggg   3420
```

| | | | | | |
|---|---|---|---|---|---|
| tttggttgtg | gttaaacctg | tatttcaagc | caagctcttc | tggtttttct | tcttcaccat 3480 |
| cctcattttc | atcctctttc | cttctgtctt | ccttccaccc | catgcaggaa | ctggccaagt 3540 |
| acttcttggc | agagctgctg | tctgaaccca | accagacaga | gattgatgcc | ctggagcctg 3600 |
| aagatttgtc | ccaggctgct | gagcaggatg | aaatgaggct | ggagctgcag | agatctgcta 3660 |
| actcaaaccc | ggccatggca | ccccgagaac | gcaaagctgg | tgcaagaatt | tcttctggaa 3720 |
| gactttcaca | tcctgttaac | tttattaata | ttgttgccca | tataagacct | ctgattcctc 3780 |
| ttctccaaac | cccttctccc | tccctaatcc | ctccaatcct | caataagacc | ctcgtgttag 3840 |
| aaattgagac | tgtaaataca | aataaaatt | atgggaaatt | atg | 3883 |

QUANTITATIVE TRAIT LOCI AND SOMATOSTATIN

CROSS REFERENCE TO RELATED APPLICATIONS

The present application claims the benefit of U.S. Provisional Patent Application Ser. No. 60/361,589, filed Mar. 4, 2002, which is herein incorporated by reference.

STATEMENT REGARDING FEDERALLY SPONSORED RESEARCH OR DEVELOPMENT

Part of the work performed during the development of this invention was supported by U.S. Government funds from USDA grants NRICGP 98-04507 and NRICGP95-04507. The U.S. Government may have certain rights in this invention.

BACKGROUND OF THE INVENTION

1. Field of the Invention

The disclosure relates to the use of genetic traits in livestock for optimizing the management and marketing of livestock and improving feedlot performance and meat quality. The disclosure specifically relates to genetic markers and polymorphisms in the bovine somatostatin (SST) locus, as well as haplotypes that include the SST locus, which are associated with certain desirable traits such as marbling.

2. Description of Related Art

The following description includes information that may be useful in understanding the present disclosure. It is not an admission that any of the information provided herein is prior art, or relevant, to the presently claimed inventions, or that any publication specifically or implicitly referenced is prior art.

The field of animal husbandry has enjoyed a long history of slowly breeding desirable phenotypic traits into domestic animal livestock populations. Generally, simple breeding programs have been used to select for desirable traits that are readily measured in live animals, such as increased muscle bulk or live weight at a certain age. These breeding programs, however, select for desirable traits using classical Mendelian genetics, which does not allow for optimal control over specific phenotypic characteristics related to the eating quality of meat, such as marbling, Quality Grade, and tenderness of meat. Thus, this field is strongly interested in gene loci and polymorphisms that are discovered to be specifically associated with desirable traits that relate to the eating quality of meat and growth in feedlot cattle. Once found, animals with these gene loci and polymorphisms can be identified and selected. Additionally, the role of these loci in improving the quality of meat will allow the field to better understand the biological interactions that generate desirable traits.

Quantitative trait loci (QTLs) are of particular interest in the livestock field because QTLs can influence variation in carcass composition (for example, fat deposition sites and lean tissue yield) and quality (for example, intramuscular fat which is known as marbling, muscle tenderness, and palatability) in livestock, which are qualities of great importance to consumer satisfaction and the determination of an animal's value. The inability to identify live animals that possess the desired meat composition and quality characteristics causes inefficiency in the management, processing, and marketing of livestock. For example, cattle are fed to an "average" endpoint in feedlots before they are sold. This form of management exacerbates variations in meat quality and muscle mass, particularly in the fat content of the meat, because cattle of different genetic disposition are randomly grouped in feedlots.

In order to identify the individual carcasses that meet the specification ranges of beef purchasing customers, differences in variation of meat quality must be determined by individually sorting through processed carcasses (often numbering in the thousands each day). Due to the enormous daily volume of processed animals and limited cooler space (which reduces the ability of packers to sort), packers are unable to efficiently market their inventory based upon quality specifications. Further, packers have no ability to discriminate among carcasses that do not grade choice (superior for marbling), but could be marketed as a tender product and consequently as a better grade of meat.

It has been determined that 40 to 50% of the phenotypic variation among individual animals, with respect to quality of carcass composition, is determined by an animal's genetic profile; specifically, genetic variations in the sequences of regulatory elements such as promoters and enhancers, as well as gene coding sequences, can greatly affect the phenotypic characteristics of an animal. The remaining variation in phenotype is thought to be due to environmental effects, such as how the animal is managed and fed. In general, genotype determines an animal's potential phenotype, as well as the potential phenotypes of an animal's progeny.

Classical quantitative genetic approaches for determining quantitative genetic effects often assume that a large number of genes affect the underlying variation in an animal's phenotype, with each gene having a small effect on the phenotype. Results of recent gene mapping in plants and animals, however, demonstrate that this assumption is generally inaccurate. See Andersson et al., *Science* 263:1771-1774, 1994; de Koning et al., *Genetics* 152:1679-1690, 1999; Edward et al., *Genetics* 116:113-125, 1987; Georges et al., *Nature Genet* 4:206-210, 1993; Grobet et al., *Mammalian Genome* 9:210-213, 1998; Grobet et al., *Nature Genetics* 17:71-74, 1997; Kahler et al., *Theor Appl Genet* 72:15-26, 1986; Rothschild et al., *Proc. Natl. Acad. Sci. USA* 93:201-205, 1996; Rothschild et al., *J of Animal Breeding and Genetics* 112:341-348, 1995; Rothschild et al., *Mammalian Genome* 11:75-77, 2000; Sourdioux et al., *Poultry Sci* 75:1018-1026, 1996; Spelman et al., *Genetics* 144:1799-1808, 1996; Stone et al., *J Animal Sci* 77:1379-1384, 1999; Tanksley et al., *Heredity* 49:11-25, 1982; Vallejo et al., *Genetics* 148:349-360, 1998; and van Kaam et al., *Poultry Sci* 78:15-23, 1999).

Genes that impart a characteristic effect that explain a substantial portion of genetic variation found in a species are viewed as "gene loci," and are denoted quantitative trait loci (QTL). The term "QTL" as used herein refers to a gene locus that is associated with the genetic variation in a quantitative characteristic. When the term QTL is used, the identity of the gene locus that underlies the phenotypic effect is often unknown. These loci, when detected, may explain in aggregate from 40% to 80% of the underlying genetic variation in the expressed phenotypes found in a species.

Breeders have made substantial improvements in the expressed phenotypes of livestock populations by using classical quantitative genetic approaches, for example by selecting on growth rate and milk yield in cattle, litter size and meat yield in pigs, and egg number and feed efficiency in poultry. These classical approaches are severely hampered, however, when the characteristic or phenotype to be improved cannot be measured in live animals, or cannot be measured without expensive and time-consuming progeny testing programs to evaluate candidates available for selection. Moreover, these expensive testing programs must be carried out on a continual basis since the desirable phenotype must be expressed in the candidates' progeny before selection may occur.

Some QTLs will influence only one characteristic of an animal's phenotype, while other QTLs will result in a correlated response in other phenotypes among breeding stock. If a QTL is associated with, for example, a pleiotropic gene, i.e., a gene that influences many different characteristics, or genes that are closely linked on a chromosome that influence separate characteristics, selection based on the estimated breeding value for the characteristic associated with the QTL may cause a change in the breeding value, and hence the phenotype, for a second characteristic. This effect is known as a correlated response, and the extent to which a correlated response will occur between two characteristics is measured by the genetic correlation between the characteristics. There are numerous known correlated responses in livestock. For example, selection for increased mature weight in cattle can result in an increase in average birth weight, which may cause difficulty in calving. Selection for intramuscular fat content, or marbling, in beef cattle may also result in increased amounts of fat being deposited in other body locations, such as subcutaneous fat, or kidney, pelvic and heart fat. Nevertheless, there are QTLs that influence only one characteristic in an animal, and selection based on these QTLs will not result in a correlated response in breeding stock.

Given the lack of optimal breeding programs and methods to control the generation of desirable genotypic and phenotypic characteristics in livestock, the identification of QTLs and genetic polymorphisms that underlie genetic variations in economically important traits in livestock species offers powerful new opportunities to manage and breed individuals within various livestock species. The identification of specific polymorphisms and alleles that are linked to desired phenotypic traits will provide for new methods of selection, breeding, management, and marketing of livestock, as well as improve the quality and efficiency of production for consumers.

BRIEF SUMMARY OF THE INVENTION

The present disclosure identifies genetic polymorphisms, markers, and haplotypes that are associated with and predictive of economically important traits in livestock species. These economically important traits are associated with quantitative trait loci (QTLs), which are gene loci that are associated with the genetic variation in a quantitative characteristic or trait. These genetic polymorphisms, markers, and haplotypes can be used to predict the breeding characteristics of livestock progeny, and to optimize the management and marketing of livestock for improving feedlot performance and meat quality. The disclosure specifically relates to genetic markers linked to the bovine somatostatin (SST) locus, single nucleotide polymorphisms (SNPs) in the bovine SST locus, as well as haplotypes that include the SST locus, all of which are predictive of a particular trait of interest, such as marbling, meat quality grade, and yield grade. In a preferred embodiment, the genetic markers, SNPs, and haplotypes are associated with the likelihood that an animal will have increased or decreased marbling in its tissue.

In a preferred embodiment, the present disclosure includes methods of predicting marbling in an organism by identifying a haplotype that is predictive of marbling. Preferably, the organism is livestock, for example, bovine. In a preferred embodiment, the bovine is Angus, Brahman, Hereford, Brangus, Simmental, Longhorn, Jersey, Beefmaster, Holstein, Guernsey, Charolais, or Brown Swiss. In a preferred embodiment, the haplotype is defined by SNPs at nucleotides 244 and 575 of the bovine SST gene. In preferred embodiments, the haplotype further includes a SNP at nucleotide 126 of the SST gene, a SNP at nucleotide 157 of the SST gene, and/or a SNP at nucleotide 981 of the SST gene. In another preferred embodiment, the haplotype will have a T at nucleotide 244 and a C at nucleotide 575, or a C at nucleotide 244 and a C at nucleotide 575. Both of these haplotypes are associated with increased marbling. In an alternative preferred embodiment, the haplotype will have a C at nucleotide 244 and a T at nucleotide 575; this haplotype is associated with decreased marbling.

In another preferred embodiment, the present disclosure includes methods of predicting marbling in bovine by identifying single nucleotide polymorphisms (SNP) in the bovine SST gene that are predictive of marbling. Preferably, the bovine is Angus, Brahman, Hereford, Brangus, Simmental, Longhorn, Jersey, Beefmaster, Holstein, Guernsey, Charolais, or Swiss Brown. In a preferred embodiment, the SNP is located at nucleotide 244, nucleotide 575, nucleotide 126, nucleotide 157, and/or nucleotide 981 of the bovine SST gene.

Another aspect of the present disclosure is a preferred method of predicting a trait of interest in an organism by identifying a haplotype that is predictive of that trait. Preferably, the organism is livestock, for example, bovine. In a preferred embodiment, the bovine is Angus, Brahman, Hereford, Brangus, Simmental, Longhorn, Jersey, Beefmaster, Holstein, Guernsey, Charolais, or Swiss Brown. In a preferred embodiment, the trait that is predicted by identifying a haplotype is yearling weight, actual fat thickness over the 10th and 11th rib, quality grade, connective tissue, flavor, or juiciness. Preferably, the identified haplotype is associated with either an increase or decrease in the trait of interest. In a preferred embodiment, the haplotype is defined by SNPs at nucleotides 244 and 575 of the bovine SST gene. In preferred embodiments, the haplotype further includes a SNP at nucleotide 126 of the SST gene, a SNP at nucleotide 157 of the SST gene, and/or a SNP at nucleotide 981 of the bovine SST gene. In other preferred embodiments, the haplotype will have a T at nucleotide 244 and a C at nucleotide 575, a C at nucleotide 244 and a C at nucleotide 575, or a C at nucleotide 244 and a T at nucleotide 575.

In another preferred embodiment, the present disclosure includes methods for predicting marbling in bovine comprising identifying single nucleotide polymorphisms (SNP) in the bovine somatostatin gene that are predictive of marbling, by (a) obtaining a sample of nucleic acid from a bovine individual; wherein the sample contains at least a portion of a bovine somatostatin gene and (b) determining the identity of one or more single nucleotide polymorphisms (SNPs) located at nucleotides 126, 157, 244, 575, and 981 of the bovine SST gene. In a preferred embodiment, the identity of the SNPs located at nucleotides 244 and 575 of the bovine SST gene are determined. In preferred embodiments, an SNP may be identified in a sample of nucleic acid from an organism, for example DNA or RNA, by a number of methods well known to those of skill in the art, including but not limited to DNA sequencing, DNA amplification, Oligonucleotide Ligation Assay (OLA), Doublecode OLA, Single Base Extension Assay, allele specific primer extension, or mismatch hybridization. Preferably, the identity of one or more SNPs in the bovine SST gene is determined by amplifying at least a portion of the sample of nucleic acid encoding the bovine SST gene, or by sequencing at least a portion of the sample of nucleic acid encoding the bovine SST gene.

In yet another preferred embodiment, the present disclosure includes methods for identifying in a species of interest a haplotype that includes an allele of the SST gene, or a SNP in the SST gene, that is predictive of a trait of interest, wherein the haplotype or SNP is associated with an increase or decrease in the trait of interest. Preferably, the species of interest include human, bovine, porcine, ovine, equine, rodent, avian, fish, and shrimp. In another preferred embodiment, the traits of interest that are associated with the SST gene include marbling, hot carcass weight, ribeye muscle area, meat Quality Grade, Warner-Bratzler shear force, Yield Grade, yearling weight, actual fat thickness over the 10th and 11th rib, connective tissue, flavor, and juiciness. In preferred embodiments, methods are disclosed for identifying a haplotype that predicts marbling in a species of interest, wherein the haplotype includes an allele of the SST gene that is associated with either increased or decreased marbling. In other preferred embodiments, methods are disclosed for identifying a SNP in the SST gene in a species of interest which is predictive of marbling, wherein the SNP is associated with either increased or decreased marbling.

In a preferred embodiment, the present disclosure includes methods for selecting breeding individuals in a species of interest to produce offspring by selecting at least a first parent that has a haplotype predictive of a trait of interest. Preferably, the species of interest is bovine and the haplotype is predictive of increased marbling. In another preferred embodiment, the haplotype includes SNPs at nucleotides 244 and 575 of the bovine SST gene. In preferred embodiments, the haplotype further includes a SNP at nucleotide 126 of the SST gene, a SNP at nucleotide 157 of the SST gene, and/or a SNP at nucleotide 981 of the SST gene. Preferably the first parent bovine with the selected haplotype is mated with a second parent bovine to produce offspring. In a preferred embodiment, the offspring demonstrate an increase in the desired trait of interest, for example increased marbling. In another preferred embodiment, the first and second parent bovines are selected to have a haplotype predictive of the trait of interest, for example marbling.

A preferred embodiment of the present disclosure is an isolated nucleic acid molecule that includes one or more SNP in the bovine SST gene that is associated with a trait of interest. Preferably, the isolated nucleic acid molecule includes contiguous nucleotides of the bovine SST gene, as disclosed in SEQ ID NO:1 or in SEQ ID NO:27. In another preferred embodiment, the isolated DNA molecule includes at least one SNP in SEQ ID NO:1 selected from the group consisting of a T at nucleotide 126 of SEQ ID NO:1; a T at nucleotide 157 of SEQ ID NO:1; a C at nucleotide 244 of SEQ ID NO:1; a T at nucleotide 575 of SEQ ID NO:1; and an A at nucleotide 981 of SEQ ID NO:1.

In preferred embodiments, the isolated nucleic acid molecule with a SNP in the bovine SST gene can be about 12, 13, 14, 15, 16, 17, 18, 19, 20, 21, 22, 23, 24, 24, 26, 27, 28, 29, 30, 40, 50, 100, 200, 300, 400, 500, 600, 700, 800, 900, and 1000 or more contiguous nucleotides in length. In a preferred embodiment, the isolated nucleic acid molecule is at least about 18 contiguous nucleotides (which can also be referred to as a primer or an oligonucleotide) of SEQ ID NO:1, and includes nucleotide 244 wherein the T is replaced by a C. In another preferred embodiment, the nucleotide corresponding to nucleotide 244 of SEQ ID NO:1 is located at the 3' end of the isolated nucleic acid molecule. In yet another preferred embodiment, the nucleotide corresponding to nucleotide 244 of SEQ ID NO:1 is located at the 5' end of the isolated nucleic acid molecule. A preferred embodiment of the present disclosure is an isolated nucleic acid molecule that is the complement of the nucleic acid molecule that includes nucleotide 244 wherein the T is replaced by a C.

In another preferred embodiment, the isolated nucleic acid molecule is at least about 18 contiguous nucleotides of SEQ ID NO:1, and includes nucleotide 575 wherein the C is replaced with a T. In another preferred embodiment, the nucleotide corresponding to nucleotide 575 of SEQ ID NO:1 is located at the 3' end of the isolated nucleic acid molecule. In yet another preferred embodiment, the nucleotide corresponding to nucleotide 575 of SEQ ID NO:1 is located at the 5' end of the isolated nucleic acid molecule. A preferred embodiment of the present disclosure is an isolated nucleic acid molecule that is the complement of the nucleic acid molecule that includes nucleotide 575 wherein the C is replaced by a T.

In yet another preferred embodiment, the isolated nucleic acid molecule is at least about 20 contiguous nucleotides of SEQ ID NO:1, and includes nucleotide 126 wherein the C is replaced with a T. In another preferred embodiment, the nucleotide corresponding to nucleotide 126 of SEQ ID NO:1 is located at the 3' end of the isolated nucleic acid molecule. In yet another preferred embodiment, the nucleotide corresponding to nucleotide 126 of SEQ ID NO:1 is located at the 5' end of the isolated nucleic acid molecule. A preferred embodiment of the present disclosure is an isolated nucleic acid molecule that is the complement of the nucleic acid molecule that includes nucleotide 126 wherein the C is replaced by a T.

In another embodiment, the isolated nucleic acid molecule is at least about 12 contiguous nucleotides of SEQ ID NO:1, and includes nucleotide 157 wherein the C is replaced with a T. In another preferred embodiment, an isolated nucleic acid molecule has at least about 18 contiguous nucleotides of SEQ ID NO:1 from nucleotide position 139 to nucleotide position 175 of SEQ ID NO:1, wherein the nucleotide corresponding to nucleotide 157 of SEQ ID NO:1 is a T. In another preferred embodiment, the nucleotide corresponding to nucleotide 157 of SEQ ID NO:1 is located at the 3' end of the isolated nucleic acid molecule. In yet another preferred embodiment, the nucleotide corresponding to nucleotide 157 of SEQ ID NO:1 is located at the 5' end of the isolated nucleic acid molecule. A preferred embodiment of the present disclosure is an isolated nucleic acid molecule that is the complement of the nucleic acid molecule that includes nucleotide 157 wherein the C is replaced by a T. In yet another preferred embodiment, the isolated nucleic acid molecule that includes nucleotide 157 wherein the C is replaced with a T, further includes nucleotide 126 wherein the C is replaced with a T; nucleotide 244 wherein the T is replaced with a C; nucleotide 575 wherein the C is replaced with a T; and/or nucleotide 981 wherein the G is replaced with an A.

In a preferred embodiment, the isolated nucleic acid molecule is at least about 18 contiguous nucleotides of SEQ ID NO:1, and includes nucleotide 981 wherein the G is replaced with an A. In another preferred embodiment, the nucleotide corresponding to nucleotide 981 of SEQ ID NO:1 is located at the 3' end of the isolated nucleic acid molecule. In yet another preferred embodiment, the nucleotide corresponding to nucleotide 981 of SEQ ID NO:1 is located at the 5' end of the isolated nucleic acid molecule. A preferred embodiment of the present disclosure is an isolated nucleic acid molecule that is the complement of the nucleic acid molecule that includes nucleotide 981 wherein the G is replaced by an A.

A preferred embodiment of the present disclosure is an isolated nucleic acid molecule with at least 19 contiguous nucleotides of SEQ ID NO:1, and includes (a) nucleotide 244 wherein the T is replaced with a C; (b) nucleotide 575 wherein the C is replaced with a T; or both (a) and (b). Yet another preferred embodiment of the present disclosure is an array of nucleic acid molecules attached to a solid support, wherein the array includes an oligonucleotide that will hybridize to a nucleic acid molecule consisting of SEQ ID NO:1, wherein the T at nucleotide 244 is replaced by C; the C at nucleotide 575 is replaced by T; the C at nucleotide 126 is replaced by T; the C at nucleotide 157 is replaced by T; and/or the G at nucleotide 981 is replaced by A. Preferably the oligonucleotide is hybridized under conditions where the oligonucleotide will preferentially hybridize to one allele and no other alleles of the bovine SST locus.

Another preferred embodiment of the present disclosure includes an isolated nucleic acid molecule of SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, or SEQ ID NO:25. Another embodiment includes the isolated nucleic acid molecule that is the complement of SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, or SEQ ID NO:25. A preferred embodiment also includes the isolated nucleic acid molecules of SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, or SEQ ID NO:25 operably attached to a detectable label.

A further embodiment of the present disclosure includes a kit for identifying a SNP in a bovine including at least a first SNP identifying reagent and at least a first SNP detecting reagent. In a preferred embodiment, the first identifying reagent is SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, or SEQ ID NO:25, and is operably attached to a detectable label.

BRIEF DESCRIPTION OF THE SEVERAL VIEWS OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 12. Nucleic acid sequence alignment of the human (Accession No. J00306), rat (Accession No. J00787), and bovine (disclosed sequence) genomic sequence for the SST locus. The bovine sequence from –1588 to –466 has not been previously disclosed in the published bovine sequence (Accession No. U97077). The novel bovine sequence does have some sequence identity with rat and human sequences. The exon sequences and regulatory sequences in the bovine sequence are underlined; the SNPs in the bovine sequence are boxed and bolded nucleotides (wild-type SNP alleles shown). The bovine sequence is SEQ ID NO:1, the human sequence is SEQ ID NO:2, and the rat sequence is SEQ ID NO:3.

FIG. 13. A chart showing five novel single nucleotide polymorphisms (SNPs) located in the SST locus of forty-four individual bovine animals. The bovine animals represented are grandparents and parents in the Angleton Family Pedigree. The nucleotide position and base change is indicated across the top of the chart for the five SNPs. The first listed base is the more common or "wild-type" polymorphism while the second base is the less common or alternate polymorphism. For example, T244C indicates that at position 244 of the SST gene, the common SNP allele is T while the alternate SNP allele is C. The chart further shows the two alleles of the SST locus for each individual at a particular position in the SST gene, which indicates whether the animal is homozygous or heterozygous at that particular location in the SST gene.

FIG. 14. The sequence of the bovine SST locus, also shown in SEQ ID NO:27 (a portion of which is shown in SEQ ID NO:1). The base positions of the five identified SNPs in the SST locus are boxed and bolded (nucleotides 126, 157, 244, 575, 981). Additionally, the two exons of the SST gene, as well as CRE, CAAT, and TATA sequences, are underlined.

DETAILED DESCRIPTION OF THE INVENTION

Figure 1:
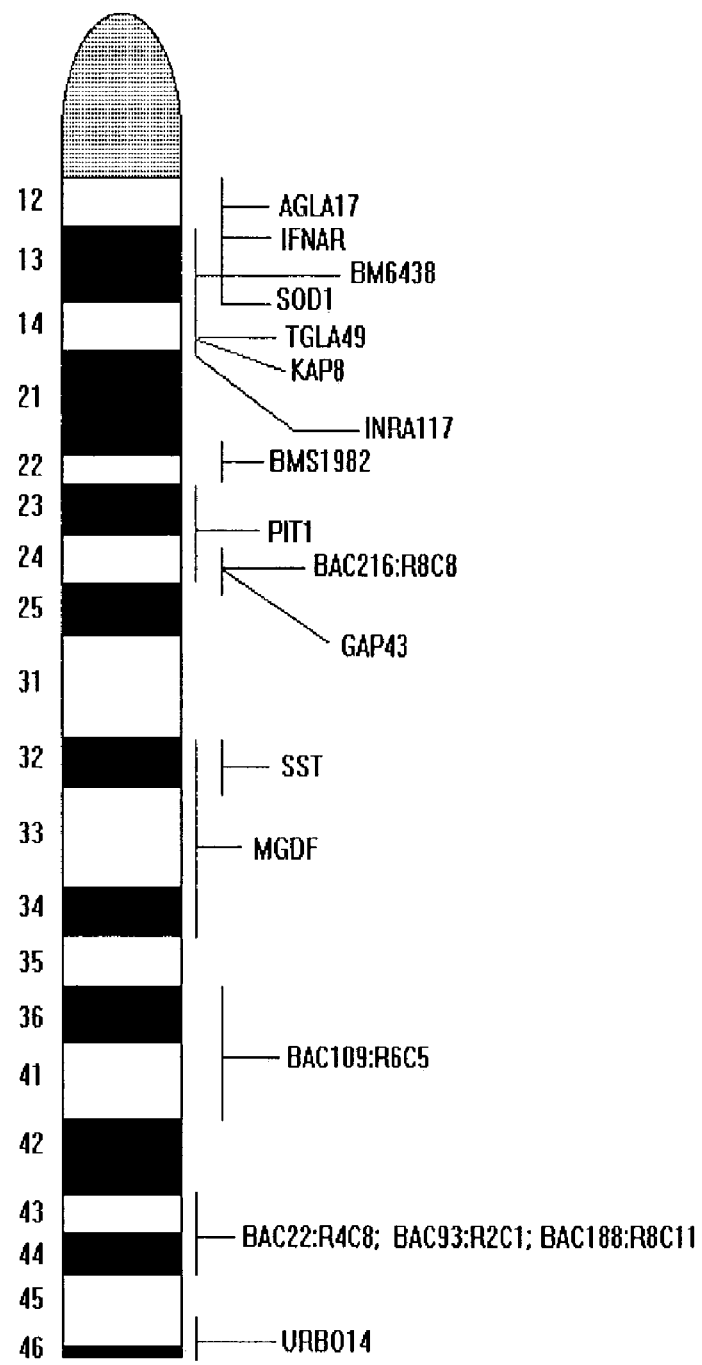
FIG. 1. A chromosome map of bovine chromosome 1. The map shows the position of the Somatostatin (SST) locus near the central region of chromosome 1.
Figure 2:
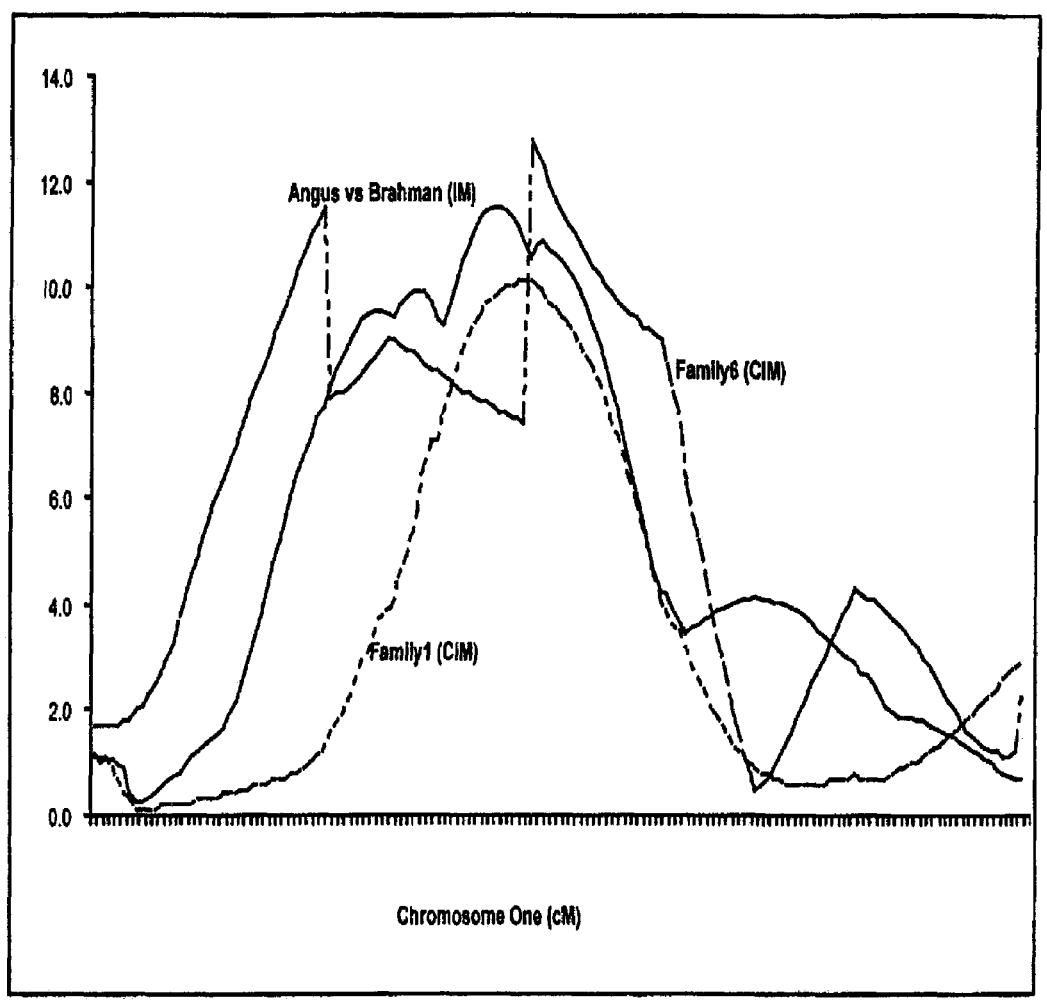
FIG. 2. The graph shows the likelihood ratio profiles for bovine chromosome 1. The curves represent analyses of weaning weight (WWT) showing significant Angus versus Brahman QTL effects in the vicinity of the SST locus using interval mapping (IM). The graph also provides significant Angus versus Brahman allele substitution effects in the progeny of Family 1, fathered by an $F_1$ (which is a cross between Angus and Brahman) bull, and Family 6, mothered by an $F_1$ cow, using composite interval mapping (CIM).

The present disclosure is directed to improving the efficiency and predictability of animal husbandry and management of livestock breeding by identifying genetic characteristics in animals that are associated with quantitative trait loci (QTLs), particularly in bovine animals. The disclosure relates to the use of genetic traits in livestock for determining breeding characteristics of livestock progeny, and for optimizing the management and marketing of livestock for improving feedlot performance and meat quality. The disclosure specifically relates to genetic markers, polymorphisms, and haplotypes that are indicative of QTLs, for example genetic markers and single nucleotide polymorphisms (SNPs) in the somatostatin (SST) locus, as well as haplotypes that include the SST locus. The traits that are associated with the SST locus in bovine include marbling, hot carcass weight, ribeye muscle area, meat Quality Grade, Warner-Bratzler shear force, Yield Grade, yearling weight, actual fat thickness over the 10th and 11th rib, connective tissue, flavor, and juiciness. In a preferred embodiment, identified SNPs and haplotypes associated with the SST locus are genetically linked to increased or decreased marbling in the tissue of a bovine animal.

The embodiments of the present disclosure include methods for managing and breeding livestock, for example by using marker assisted selection and marker assisted introgression of livestock populations. Marker assisted selection provides for genotyping animals and identification of animals having desirable versus undesirable genotypes based on their linkage with QTLs. Animals with the desirable genotypes are preferred for breeding. The term introgression describes the process of moving desirable alleles or polymorphisms from one population to another population that has other phenotypic characteristics that are desirable in a livestock population. For example, a polymorphism found in Angus animals that is associated with a specific trait (e.g. an SST locus polymorphism linked with an increased marbling score in bovine), but is not present in another breed, such as Simmental animals, may be introgressed into the Simmental line through the use of genetic screening and directed breeding programs. Once the polymorphism is introgressed into the line, the Simmental animals will be more likely to have the desired trait found in the Angus animals.

The use of genetic markers to identify the desirable polymorphism in the Angus genome increases the likelihood that only the desirable polymorphism will be transmitted to offspring through natural mating with a different breed while the remainder of the Angus genome, much of which may be undesirable, is left behind. This breeding process requires a series of backcrosses to generate a new line of animals with the desirable polymorphism in a different breed. This analysis, selection, and/or introgression can be performed by screening for genetic markers, polymorphisms, or haplotypes that are associated with the QTL of interest or are in linkage disequilibrium with the QTL. Additionally, polymorphisms or genetic markers may be the causal mutation for the QTL, so that animals with the causal polymorphism(s) or genetic marker(s) will have the phenotype associated with the QTL. Preferably, a polymorphism or genetic marker that is a causal mutation will be screened for directly. Alternatively, one of skill in the art can screen for a haplotype that includes such a polymorphism or genetic marker, because the haplotype is also associated with the desired phenotype. Many different types of polymorphisms may be causal, including but not limited to point mutations, deletions, duplications, and translocations. It is also possible, as shown with double muscling cattle, that more than one mutation may be responsible for variations in a specified trait (Grobet et al., *Mamm Genome* 9:210-213, 1998).

Given the lack of optimal breeding programs and methods to select for the generation of desirable genotypic and phenotypic characteristics in livestock, a family pedigree of bovine animals, the Angleton Family Pedigree, was generated for linkage analysis studies. This linkage mapping study was designed to identify QTLs that underlie the genetic variation in economically important characteristics in livestock species. This method is also called the positional candidate gene approach (Collins, *Nature Genet* 9:347-350, 1995). Positional cloning requires no knowledge of the function of a gene; rather a chromosomal region is identified that is associated with a QTL, and candidate genes that may be responsible for the QTL in the region are identified based on map position. Through the identification of genetic variations, markers, and polymorphisms that are associated with these QTLs, powerful new opportunities are available to appropriately manage and breed the best animals within various livestock species. Particularly, the identification of specific QTLs, genetic markers, and/or polymorphisms present in individual animals offers new methods of selecting, breeding, managing, and marketing livestock.

The positional candidate gene approach utilizes a carefully designed breeding program in which the QTLs are segregating, and genetic marker analysis is used to identify animal genotypes at marker loci. Statistical analysis is then used to test the strength of the linkage of chromosomal regions to QTLs, as well as the magnitude of the gene effect (Liu, *Statistical Genomics: Linkage, Mapping and QTL Analysis*, CRC Press, Boca Raton, Fla., 1998). Several breeding program designs are available that will segregate traits of interest for mapping studies. Backcross or $F_2/F_3$ populations have been commonly used to detect linkage between molecular markers and genes controlling quantitative traits. An $F_2$ population is generally preferred if several QTLs are segregating in the population and if estimates of their additive and dominance effects are desired (Darvasi, *Nature Genet* 18:19-24, 1998). In species where severe inbreeding is economically feasible, recombinant inbred populations have also been used (Austin and Lee, *Genome* 39:957-968, 1996).

The purpose of the controlled crosses used to produce pedigree mapping populations is to maximize linkage disequilibrium within the progeny of the crosses. Linkage disequilibrium is the nonrandom association of alleles at different loci in a population and can be caused by a number of factors, including selection and genetic drift. The underlying assumption when using marker loci to detect QTLs is that linkage disequilibrium exists between alleles at the marker locus and alleles of adjacent, linked loci. Linkage disequilibrium due to physical linkage of loci reaches its highest value in populations derived from controlled matings and, as a consequence, the ability to map and characterize QTLs using marker loci is also maximized (Tanksley, *Ann Rev Genet* 27:205-233, 1993). Thus, genetic markers can greatly facilitate the search for genes that influence QTLs of interest in cattle. Ideally, genetic markers are highly polymorphic, abundant, neutral, and co-dominant, and include but are not limited to RFLPs, VNTRs, minisatellites, and microsatellites. In 1993, Fries et al. (*Mamm Genome* 4:405-428) consolidated all available marker information to produce a bovine genetic map containing 350 informative loci. Since then, thousands of additional genetic markers have been identified. Bovine physical maps also provide a useful resource in the search for candidate genes, and linkage groups have been assigned to bovine chromosomes by fluorescence in situ hybridization (FISH) (see Solinas-Toldo et al., *Genomics* 27:489, 1995; Eggen and Fries, *Anim Genet* 26:215-36, 1995).

There are several statistical methods and models for determining whether a QTL is linked to a genetic marker or polymorphism that are well known to those of skill in the art. All of the statistical procedures share the same basic principle: "to partition the population into different genotypic classes based on genotypes at the marker locus and then to use correlative statistics to determine whether the individuals of one genotype differ significantly compared with individuals of other genotypes with respect to the trait being measured." (Tanksley, *Ann Rev Genet* 27:205-233, 1993). If the phenotypes differ significantly, then it is interpreted that the genotype affecting the trait is linked to the marker locus used to subdivide the population. The procedure is repeated for additional marker loci throughout the genome to detect as many QTLs as possible.

The simplest approach for detecting QTLs is to analyze the data using one marker at a time. This approach is often referred to as single point analysis or point analysis (Soller et al., *Theor Appl Genet* 47:35-39, 1976). The most powerful statistical approach to detect QTLs, however, is interval mapping (IM). See Darvasi et al., *Genetics* 134:943-951, 1993; Haley and Knott, *Heredity* 69:315-324, 1992; Haley et al., *Genetics* 136:1197-1207, 1994; Jansen, *Genetics* 135:205-211, 1993; Jansen and Stam, *Genetics* 136:1447-1455, 1994; Zeng, *Genetics* 136:1457-1468, 1994. By using linked markers for analysis, it is possible to compensate for recombination between the markers and the QTL, thereby increasing the probability of statistically detecting the QTL, and also providing an unbiased estimate of the QTL effect on the characteristic (Paterson et al., *Nature* 335:721-726, 1988; Stuber et al., *Genetics* 132:823-839, 1992).

The interval between pairs of flanking markers is explored in turn for the presence of a QTL at various positions between the markers. IM methods have provided some additional power and are much more accurate estimates of QTL effect and position. IM methods have also proven to be relatively robust to the failure of normality assumptions. IM was originally implemented using maximum likelihood. According to the methods used for parameter estimation, IM can be classified into three approaches:1) likelihood (Lander and Botstein, *Genetics* 121:185-199, 1989); 2) nonlinear and linear regression (Knapp et al., *Theor Appl Genet* 79:583-592, 1990; Knapp et al., *Plant Genomes: Methods for Genetic and Physical Mapping*, pp.209-237, Kluwer Academic Publishers, Dordrecht, The Netherlands, 1992); and 3) likelihood and multiple regression (Zeng, *Genetics* 136:1457-1468, 1994). The weight of evidence supporting the presence of a QTL can be determined by the LOD score, defined as the logarithm base 10 of the ratio of likelihood of the sample assuming no QTL to the likelihood evaluated at the most likely position of a QTL on the chromosome (Liu, *Statistical Genomics: Linkage, Mapping and QTL Analysis*, CRC Press, Boca Raton, Fla., 1998).

With respect to the current disclosure, the SST locus at cytogenetic region 1q32 on bovine chromosome 1 is associated with numerous QTLs. Genetic markers, polymorphisms, and genetic variations that are linked to the SST locus and the QTLs may be used to screen animals. Animals with favorable genotypes can be used to increase the frequency of one or more desired traits in animals through livestock breeding and management programs. In a preferred embodiment, the present disclosure identifies specific genetic markers and polymorphisms in the SST locus or linked with the SST locus that are associated with QTLs that affect the regulation of growth, carcass yield, and quality characteristics in livestock.

Linkage analysis using genetic markers and polymorphisms is a powerful tool for finding the chromosomal region (s) that is associated with a trait of interest. A variety of polymorphisms may be used in linkage analysis, including but not limited to single nucleotide polymorphisms (SNPs), simple tandem repeats (STRs) or microsatellites, restriction fragment length polymorphisms (RFLPs), variable number of tandem repeats (VNTRs), complex tandem repeats (CTRs), deletions, rearrangements, or insertions. These polymorphisms can also be used to identify a particular haplotype or combination of alleles at two or more loci in an individual animal that is correlated with the presence or absence of a desired phenotype or trait in livestock. Thus, a haplotype can be identified and defined by genetic markers and/or polymorphisms.

Although linkage analysis studies can be performed using a general population of animals, specific families are often used to map an unknown gene linked to a phenotype. The genetic linkage or connection between the desired traits and a particular locus is determined by analyzing the Angleton Family Pedigree. Once linkage analysis identifies the chromosomal region associated with the trait of interest, and a candidate gene and/or a polymorphism or genetic marker linked to a desired trait is found, genetic testing and analysis can be used to identify the same gene, genetic marker, or polymorphism linked to the phenotype in any bovine population, as well as in other livestock species. Livestock species that have the SST gene and are contemplated in this disclosure include cattle, pigs, sheep, horses, poultry, fish, and shrimp. Also contemplated are bovine breeds well known to those of skill in the art, including but are not limited to Angus, Brahman, Hereford, Brangus, Simmental, Longhorn, Jersey, Beefmaster, Holstein, Guernsey, Charolais, and Swiss Brown.

The Angleton Family Pedigree generated for mapping QTLs in bovine consisted of three generations of animals. The mapping population was a reciprocal backcross and $F_2$ design that contrasted the *Bos taurus* (Angus) and *Bos indicus* (Brahman) genomes, and included 701 individuals from grandparent, parent, and progeny generations. A total of 43 fullsib families (18 Angus backcross; 22 Brahman backcross; 3 $F_2$) were produced by multiple ovulation and embryo transfer for an average of 14.3 fullsibs per family. There were a total of 614 progeny, and with the exception of a limited number of progeny retained for further breeding, 542 of the 614 progeny were slaughtered and data was gathered on each of these animals.

The pedigree was constructed for the primary purpose of localizing QTLs associated with variation in growth, carcass yield, and meat quality traits. The term "growth" as used herein refers to the change in an animal's live weight between two points in time, such as from birth to weaning times, or from entry to exit times in a feedlot. The term "weaning" as used herein refers to the event whereby a calf is removed from its mother and gains nourishment from the consumption of fodder. It is at this point that the animal develops rumen function. The term "carcass yield" as used herein refers to the yield of lean trimmed retail cuts of meat from a carcass which is estimated by the USDA Yield Grade standards set forth in the Official United States Standards for grades of Carcass Beef promulgated by the Secretary of Agriculture under the Agricultural Marketing Act of 1946 (60 Stat. 1087; 7 U.S.C. 1621-1627) as amended and related authority in the annual appropriation acts for the Department of Agriculture.

Progeny were recorded for horned or polled status, coat color, coat speckling, structural health, weight for age, and growth characteristics. All progeny were carried through feedlot and carcass evaluation stages, and were slaughtered after approximately 150 days on feed. Growth measurements included: birth weight, weaning weight, feedlot entry weight, final feedlot weight, days on feed in the feedlot, and fasted slaughter weight. Additionally, average daily weight gain from birth to weaning, from weaning to feedlot entry, and within the feedlot were calculated for each animal. Carcass data included hot carcass weight; dressing percentage; longissimus dorsi (ribeye muscle) cross-sectional area; kidney, pelvic, and heart fat as a percentage of body weight; actual and adjusted fat depth at the 12-13th thoracic rib junction; marbling; as well as Quality Grade and Yield Grade as determined according to the United States Department of Agriculture specifications. Tissue samples were also analyzed to determine the extractable lipids, moisture, protein, and collagen contents of the 9-10-11th rib dissection, Warner-Bratzler shear force, descriptive sensory panel (taste panel) analysis, fragmentation index, calcium dependent protease analysis, sarcomere length, fatty acid and cholesterol composition, the longissimus dorsi, and stearyl coA desaturase and fatty acid elongase activity in the longissimus dorsi.

The term "hot carcass weight" as used herein refers to the weight of the eviscerated carcass immediately post-slaughter. The term "marbling" as used herein refers to the extent of intramuscular fat, usually determined in the longissimus dorsi (ribeye) muscle at the 12th and 13th rib juncture by a qualified operator at approximately 24 hours postmortem. The term meat "Quality Grade" as used herein refers to the quality of meat from a carcass which is estimated by the USDA Quality Grade and is determined using measures on the carcass including marbling and an estimate of the animal's age known at maturity as set forth in the Official United States Standards for grades of Carcass Beef promulgated by the Secretary of Agriculture under the Agricultural Marketing Act of 1946 (60 Stat. 1087; 7 U.S.C. 1621-1627) as amended and related authority in the annual appropriation acts for the Department of Agriculture. The term "meat quality" as used herein refers to the combination of meat tenderness, marbling, and palatability. The term "meat tenderness" as used herein refers to the tenderness of meat determined either by mechanical testing using the Warner-Bratzler shear force method, or by sensory evaluation using a trained taste panel.

After the progeny were analyzed and data were collected, a whole genome scan for QTLs based on 414 genetic marker loci distributed on all 29 bovine autosomes and the bovine X chromosome was performed using several analytical approaches. First, interval mapping (IM) and composite interval mapping (CIM) was performed using the program MAPMAKER QTL (Lincoln et al., Whitehead Institute for Biomedical Research, Nine Cambridge Center, Cambridge, Mass. 02142-1479). The MAPMAKER QTL program applies the approach of Haley and Knott (*Heredity* 69:315-24, 1992), to contrast the effect of inheriting Angus versus Brahman alleles in 1 cM steps throughout the genome. The use of IM is well known by those of skill in the art, and is described in Lander and Botstein, *Genetics* 121:185-199, 1989. The use of CIM is also well known, and is described in Zeng, *Proc Natl Acad Sci USA* 90:10972-10976, 1993; and Zeng, *Genetics* 136:1457-1468, 1994. These approaches assume that there are either fixed differences or highly skewed differences in QTL allele frequencies between the Angus and Brahman breeds.

Additional approaches were also used to detect the presence of QTL allelic variation within the Brahman and Angus breeds. For example, Restricted Maximum Likelihood (REML) analysis generates evidence of allelism under the infinite alleles model. The mapping data for the Angleton Family Pedigree were analyzed using the program MQREML (Hoeschele, Department of Dairy Science, Virginia Polytechnic Institute and State University, Blacksburg, Va. 24061-0315), which uses complete pedigree information and estimates the variance associated with the segregation of parental alleles throughout the pedigree. The MQREML program also uses REML to estimate a variance component associated with the segregation of parental alleles. The term "Restricted Maximum Likelihood" as used herein refers to a likelihood function that is invariant to the inclusion of fixed effects within a mixed linear model. A likelihood-ratio test is used to test the significance of the QTL variance component. The use of REML is well understood by those of skill in the art, and is described in Grignola et al. (*Mapping quantitative trait loci in outcross populations via residual maximum likelihood*, I. Methodology Theoretical and Applied Genetics 28:479-490, 1996) and Grignola et al. (*Mapping linked quantitative trait loci via residual maximum likelihood*, Theoretical and Applied Genetics 29:529-544, 1997).

Finally, the pedigree data set was partitioned into 12 subsets defined by the largest families of the $F_1$ parents. These families ranged in size from 30 to 87 progeny, and IM and CIM analyses were performed within each family to examine which families might be segregating for important QTL alleles. When the frequency of QTL alleles is similar between the Brahman and Angus animals, the MAPMAKER QTL program would not be expected to detect a QTL because the average Angus allele is contrasted against the average Brahman allele in the across-family analyses. When individual families are analyzed, however, the program should be able to detect the segregation of a QTL in a subset, but not necessarily all, of the families.

The statistical models also include the fixed effects and covariates that are relevant to the respective traits. The term "fixed effects" as used herein refers to a parameter within a linear model which is invariant to the data sampling scheme. Fixed effects are usually thought of as parameters that are used to represent the means for cells within a linear model. The term "covariates" as used herein refers to continuous variables that are used in regression analysis to adjust the data for differences in the level of the covariate. Typical covariates used in regression analysis include, for example, age or weight. For the post-slaughter characteristics, fixed effects include birth-year-season (to define a management cohort for animals from birth to slaughter), gender, breed-type (four levels for reciprocal backcross and one level for the $F_2$), gender x breed-type interaction, family nested within breed-type, as well as regressions on age in days and number of days on feed.

For pre-slaughter characteristics, the regression on number of days on feed was omitted and the regression on age at measurement was used. For birth weight a regression on day of birth within calving season was used, but there was no correction for gestation length. The effect of family was included in these analyses to account for the background genetic effects responsible for within breed genetic variance. The family effect was not fitted in the REML analyses since these analyses all used complete pedigree information (up to seven generations were available), and incorporated the animals' residual breeding values (all genes other than the tested QTL) and the complete Numerator Relationship Matrix (NRM).

Permutation tests as described by Churchill and Doerge (*Genetics* 138:963-971, 1994), with N=10,000 data permutations, were performed for each analyzed characteristic to determine the experiment-wise type I significance level on chromosome-wise and genome-wise bases. The term "experiment-wise" as used herein refers to repeating the experiment and obtaining additional samples of data that correspond to the exact experimental design as represented in the original data. The term "chromosome-wise" as used herein refers to repeating the statistical analysis using data corresponding to a repeated sample of genotypes corresponding to the chromosome of interest. The term "genome-wise" as used herein refers to repeating the statistical analysis using data corresponding to a repeated sample of genotypes corresponding to all chromosomes defining the genome. In bovine, this represents all 29 pairs of autosomes.

Using the above analytical methods, a series of QTL effects were localized to bovine chromosome 1. Table 1 below shows the likelihood ratio test statistic values and detected QTL effects in the vicinity of the SST gene on bovine chromosome 1 from the halfsib analyses using IM and CIM of Angus versus Brahman QTL differences, as well as REML under an infinite alleles model. Table 1 shows the values for all animals analyzed, as well as for specific families within the Angleton Family Pedigree (for example, Family 6 (F6)). Specifically, the data in Table 1 strongly supports the existence of QTLs influencing Weaning weight (WWT), Hot Carcass Weight (HCW), Ribeye Muscle Area (REA), Marbling (MARB), Warner-Bratzler shear force (WBSF), Quality Grade (QG), and Yield Grade (YG) in the same region as the SST locus.

In Table 1, the value of the LRT statistic represent the level of statistical support for a QTL on the chromosome that influences a given trait when the data are analyzed by IM or CIM either under a model which contrasts an average Angus with an average Brahman allele across all families or within specific families. The point on the chromosome where the LRT statistic takes its highest value is the most likely position of the QTL, provided the LRT value is convincing. This threshold level for the LRT statistic is determined by permutation testing and the type I error rates that are established. The number of stars against a LRT statistic in Table I indicates the probability of a type I error.

TABLE 1

| | | | | dist$^a$ (cM) | LRT$^j$ | a$^b$ | SE$^c$ | d$^d$ | SE$^c$ | $|2a|/r_p^e$ | $|d|/r_p^f$ |
|---|---|---|---|---|---|---|---|---|---|---|---|
| WWT | (kg) | IM | All | 64.1 | 11.5** | −1.07 | 1.73 | 8.69 | 2.49 | 0.08 | 0.34 |
| WWT | (kg) | CIM | F1 | 71.6 | 10.1 | −8.01 | | | 5.67 | | |
| WWT | (kg) | CIM | F6 | 71.6 | 12.8 | −6.46 | | | 5.41 | | |
| HCW | (kg) | IM | All | 68.1 | 12.3** | 1.48 | 2.11 | 10.16 | 2.79 | 0.10 | 0.33 |
| REA | (cm$^2$) | CIM | F7 | 71.6 | 15.6 | 0.13 | | | 5.81 | 0.02 | 0.78 |
| MARB | (score) | IM | All | 71.6 | 10.1* | 13.81 | 4.89 | −1.66 | 0.41 | 0.41 | 0.02 |
| MARB | (score) | CIM | All | 71.6 | 15.6* | 20.73 | 5.37 | −0.26 | 5.76 | 0.62 | 0.00 |
| MARB | (score) | CIM | F2 | 71.6 | 15.4 | 29.32 | | −10.20 | | | |
| MARB | (score) | IM | F12 | 66.1 | 10.6 | 37.72 | | −16.76 | | | |
| QG | (score) | IM | All | 71.6 | 11.7** | 7.62 | 2.54 | 4.39 | 3.20 | 0.41 | 0.12 |
| QG | (score) | CIM | All | 71.6 | 28.4***** | 14.22 | 3.30 | 5.35 | 3.33 | 0.77 | 0.14 |
| | | IM | F12 | 74.3 | 11.1 | 24.15 | | −1.26 | | | |
| YG | (score) | IM | F11 | 71.6 | 7.1 | 0.03 | | −0.57 | | 0.1 | 0.95 |

| | | | | dist$^a$ | LRT$^j$ | v$^{2g}$ | h$^{2h}$ | $2v^2/r_p^{2i}$ |
|---|---|---|---|---|---|---|---|---|
| MARB | (score) | REML | All | 77.0 | 7.8** | 0.16 | 0.57 | 0.18 |
| | | REML | F12 | 72.5 | 10.1** | | | |
| QG | (score) | REML | All | 75.0 | 11.2** | 0.13 | 0.67 | 0.17 |
| | | REML | F12 | 72.5 | 12.3*** | | | |
| WBSF | (kg) | REML | All | 75.0 | 5.01 | 0.49 | 0.11 | 0.06 |

$^a$At which the LRT value is maximized.
$^b$QTL genotypic value of Angus homozygotes such that 2a = AA − BB.
$^c$Standard deviations for the estimated QTL effects from 500 bootstrappings at the estimated QTL location.
$^d$AB heterozygote deviation from QTL homozygote midpoint such that d = AB − 0.5(AA + BB).
$^e$Ratio of QTL genotypic value to phenotypic standard deviation.
$^f$Ratio of QTL dominant effect to phenotypic standard deviation.
$^g$Proportion of the additive genetic variance due to the QTL allelic variances.
$^h$Narrow sense heritability.
$^i$Proportion of phenotypic variance due to the QTL genotypic variances.
$^j$*p < 0.05 and p < 0.03 chromosome-wise level for IM and CIM respectively.
**p < 0.03 and p < 0.01 chromosome-wise (suggestive) levels for IM and CIM respectively.
***p < 0.1 genome-wide (highly suggestive) level.
****p < 0.05 genome-wide (significant) level.
*****p < 0.01 genome-wide (highly significant) level.

Table 2 demonstrates the sire allele substitution effects from the halfsib analyses. The family data in Table 2 is for an Angus family (A), a Brahman family (B), and second generation crosses of Angus and Brahman animals (F$_2$). Specifically, these data indicate the average magnitude of difference exhibited in an animal's phenotype when the animal inherits one or the other alternate alleles on the two parental chromosomes from its parent.

TABLE 2

| Trait | | Family | cM | QTL effect | S.E. | t-val | P < ? |
|---|---|---|---|---|---|---|---|
| REA | (cm$^2$) | 2850 (F$_2$) | 71 | 3.99 | 1.56 | 2.55 | 0.01 |
| | | Y6 (A) | 75 | 8.43 | 5.16 | 1.63 | 0.1 |
| | | 740\7 (B) | 75 | 4.51 | 2.92 | 1.54 | 0.1 |
| MARB | (score) | 2850 (F$_2$) | 72 | 38.4 | 18.0 | 2.13 | 0.03 |
| QG | (score) | 2850 (F$_2$) | 62 | 19.1 | 10.1 | 1.74 | 0.05 |

TABLE 2-continued

| Trait | | Family | cM | QTL effect | S.E. | t-val | P < ? |
|---|---|---|---|---|---|---|---|
| WBSF | (kg) | 2850 (F$_2$) | 76 | 0.34 | 0.21 | 1.63 | 0.1 |
| | | P57 (B) | 84 | 1.52 | 0.48 | 3.18 | 0.005 |
| WWT | (kg) | Y6 (A) | 66 | 38.75 | 13 | 2.99 | 0.005 |

Figure 3:
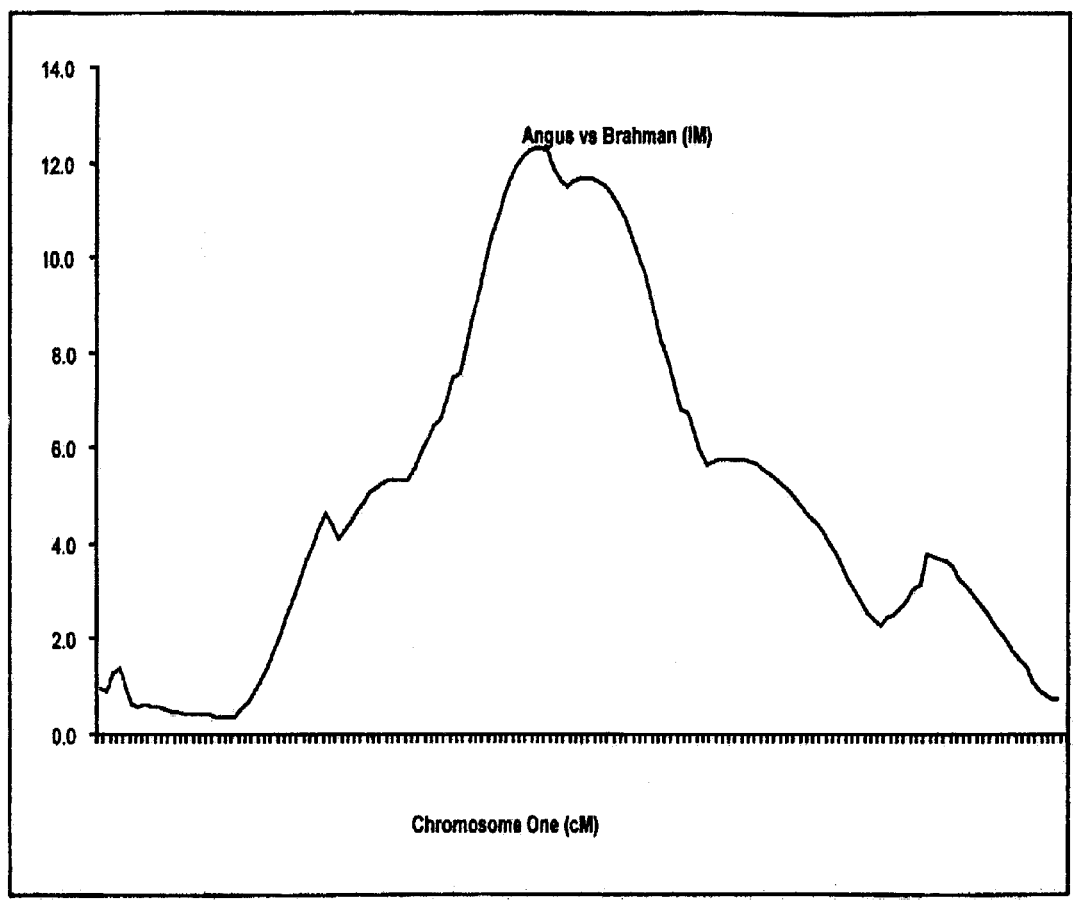
FIG. 3. The graph shows a likelihood ratio profile for bovine chromosome 1 analysis of hot carcass weight (HCW). The curve indicates significant Angus versus Brahman QTL effects in the vicinity of the SST locus using IM.
Figure 4:
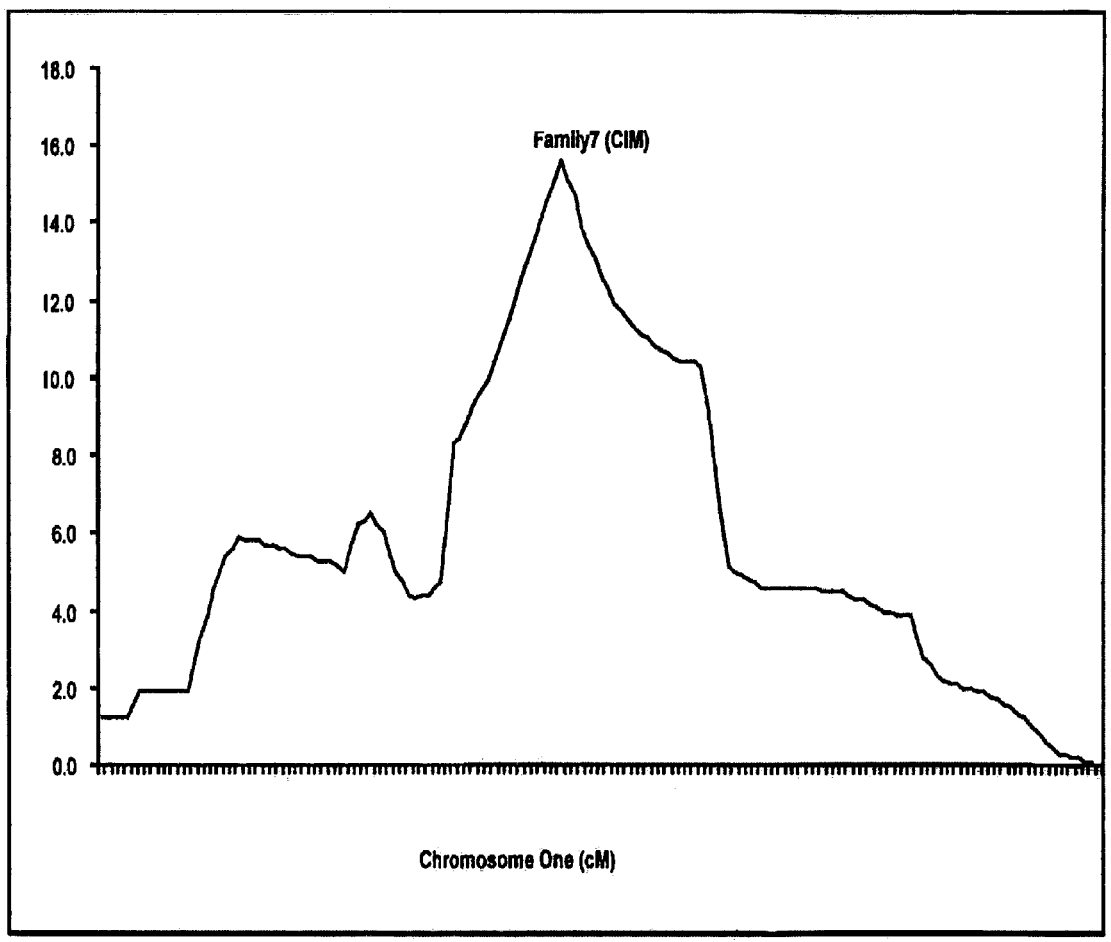
FIG. 4. The graph shows a likelihood ratio profile for bovine chromosome 1 analysis of ribeye muscle area (REA). The curve indicates a significant Angus versus Brahman allele substitution effect in the progeny of Family 7, mothered by an $F_1$ cow. This analysis indicates significant Angus versus Brahman QTL effects in the vicinity of the SST locus using CIM.

Additional data were generated to show the specific relationship of the SST locus with several desirable QTLs in livestock populations. FIGS. 2-10 represent the likelihood ratio profiles on bovine chromosome 1 for various phenotypic characteristics. As demonstrated in each figure, the profiles indicate the localization of significant effects toward the central region of chromosome 1, where the SST locus is located. Specifically, FIG. 2 profiles the correlation for weaning weight (WWT) with the chromosomal region that includes the SST locus. FIG. 3 shows the likelihood ratio profile for hot carcass weight (HCW), while FIG. 4 shows the likelihood ratio profile for the ribeye muscle area (REA), both of which map to the chromosomal region with the SST locus.

Figure 5:
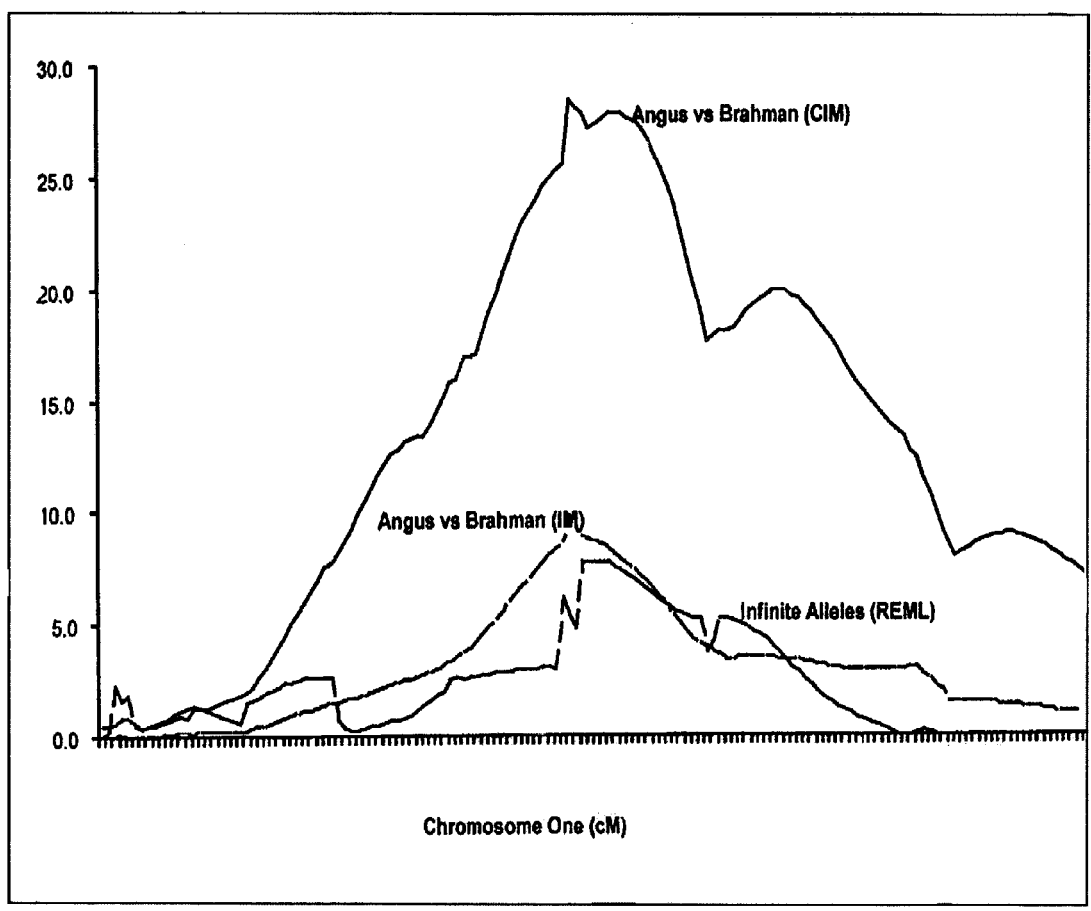
FIG. 5. The graph shows the likelihood ratio profile for bovine chromosome 1 analyses for marbling. The curves indicate significant Angus versus Brahman QTL effects in the vicinity of the SST locus using IM and CIM. The graph provides further evidence of allelism under the infinite alleles model using a Restricted Maximum Likelihood (REML) analysis.
Figure 6:
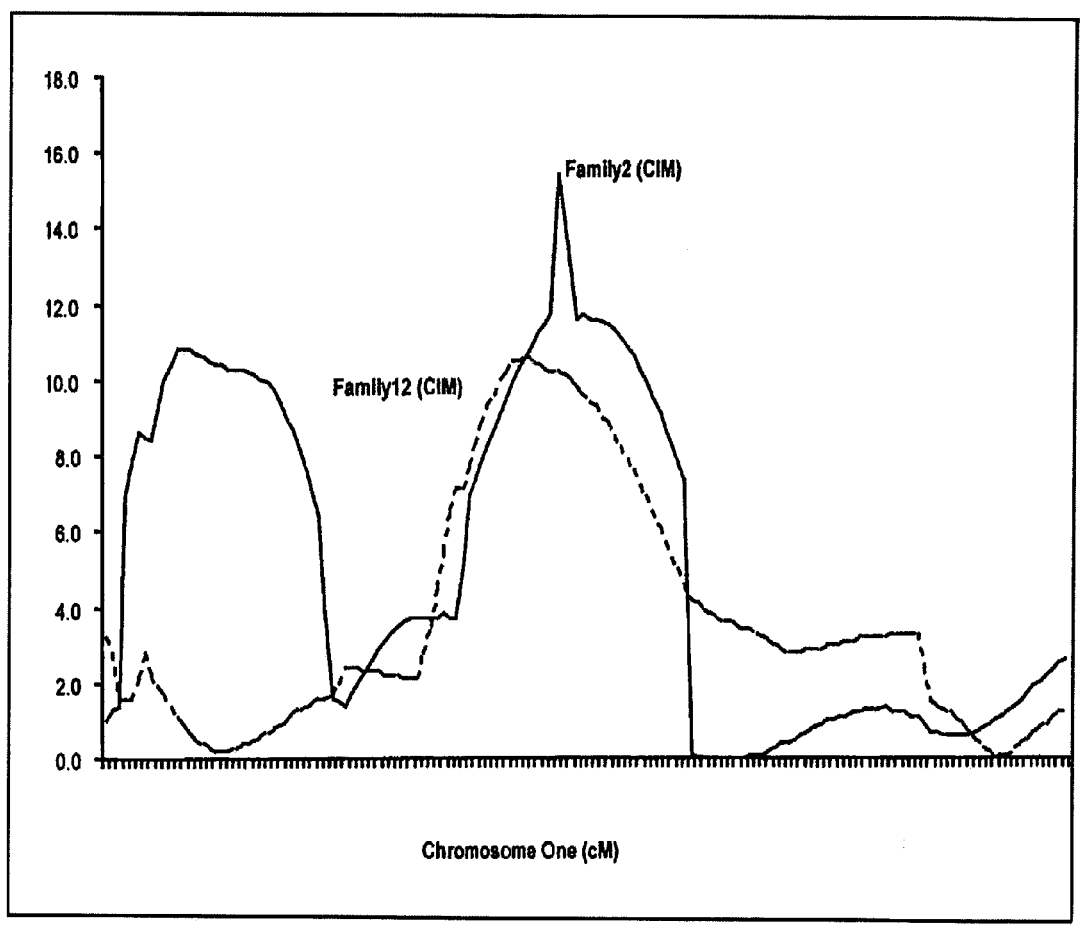
FIG. 6. The graph shows the likelihood ratio profiles for bovine chromosome 1 analyses of marbling. The curves show significant Angus versus Brahman allele substitution effects in the vicinity of the SST locus in the progeny of Family 2, fathered by an $F_1$ bull, and Family 12, mothered by an $F_1$ cow, using CIM.
Figure 7:
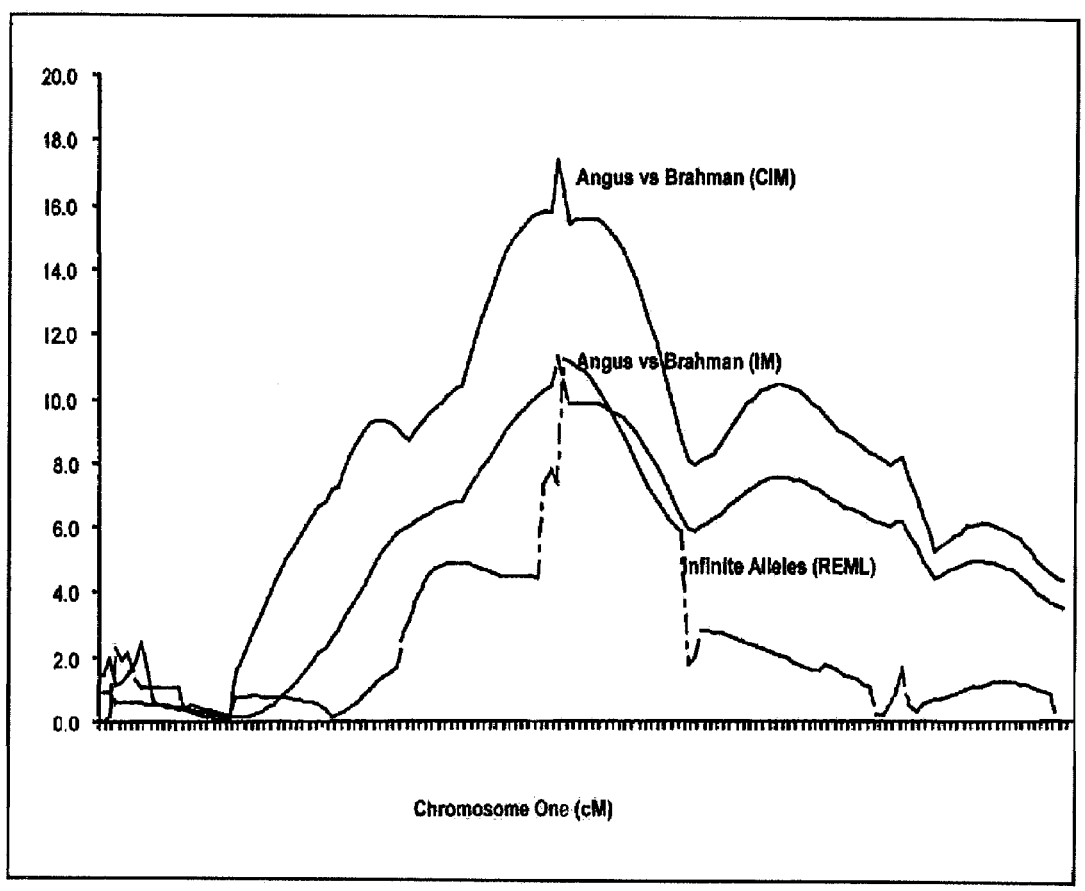
FIG. 7. The graph shows the likelihood ratio profiles for bovine chromosome 1 analyses of meat Quality Grade (QG). The curves indicate significant Angus versus Brahman QTL effects in the vicinity of the SST locus using IM and CIM. The graph also provides strong evidence of allelism under the infinite alleles model (REML).
Figure 8:
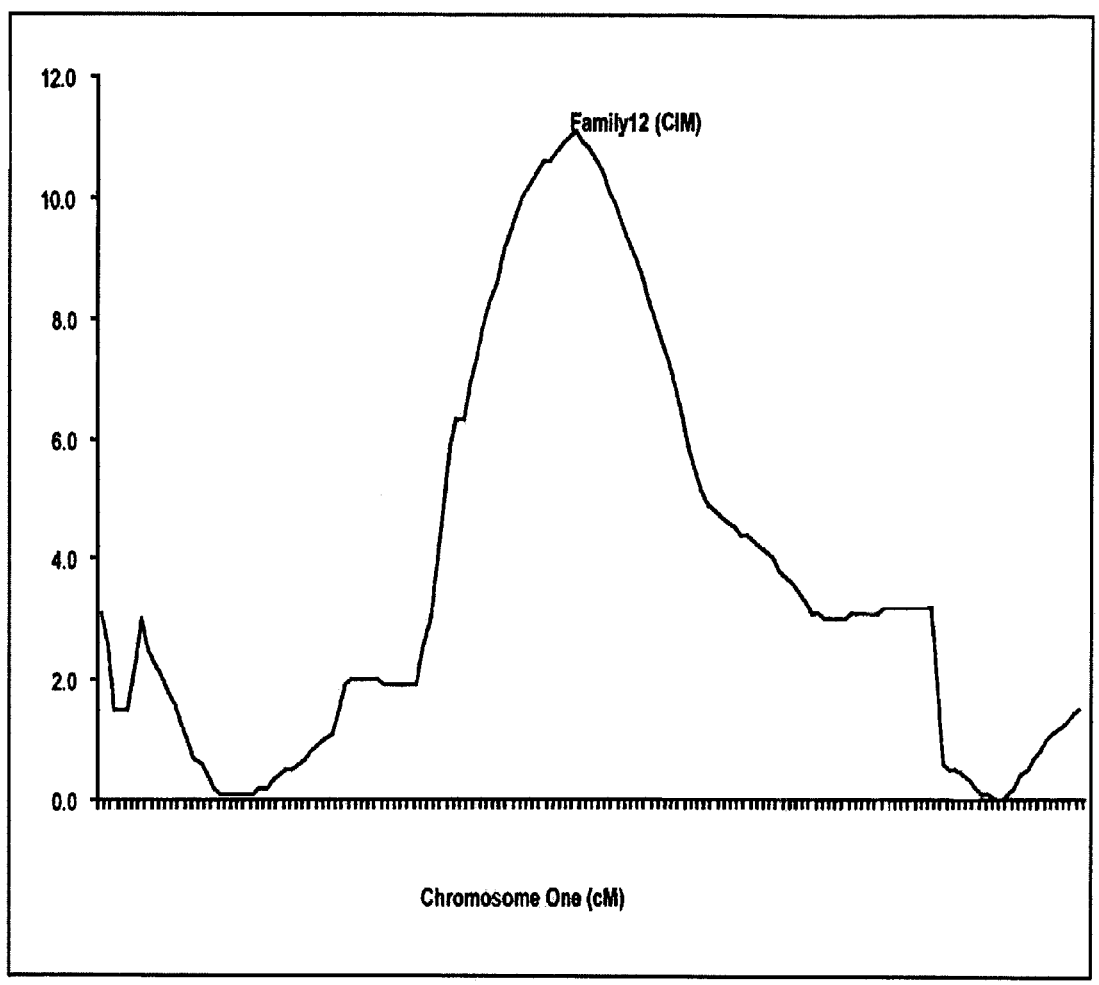
FIG. 8. The graph shows a likelihood ratio profile for bovine chromosome 1 analysis of meat Quality Grade (QG). The curve indicates significant Angus versus Brahman allele substitution effects in the vicinity of the SST locus in the progeny of Family 12, mothered by an $F_1$ cow, using CIM.
Figure 9:
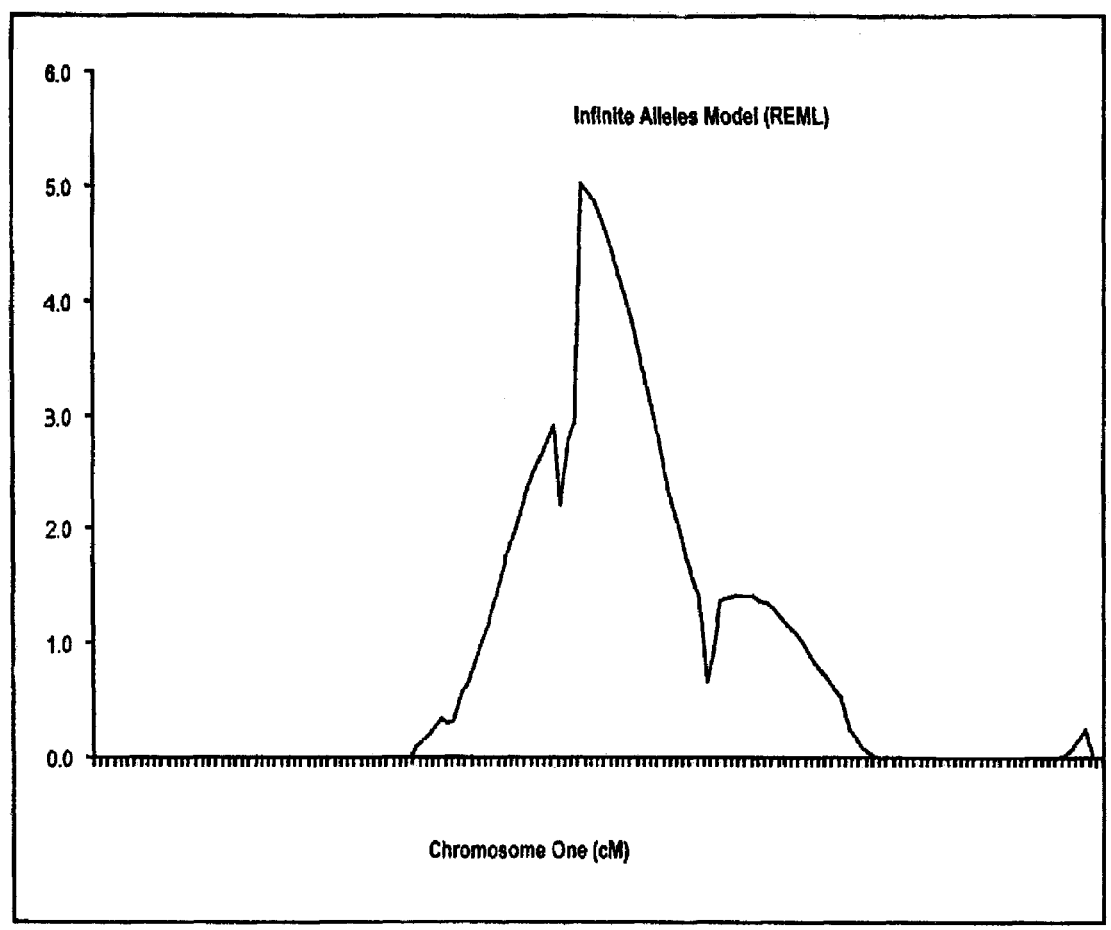
FIG. 9. The graph shows a likelihood ratio profile for bovine chromosome 1 analysis of Warner-Bratzler shear force (WBSF). The curve provides evidence of allelism in the vicinity of the SST locus under the infinite alleles model (REML).
Figure 10:
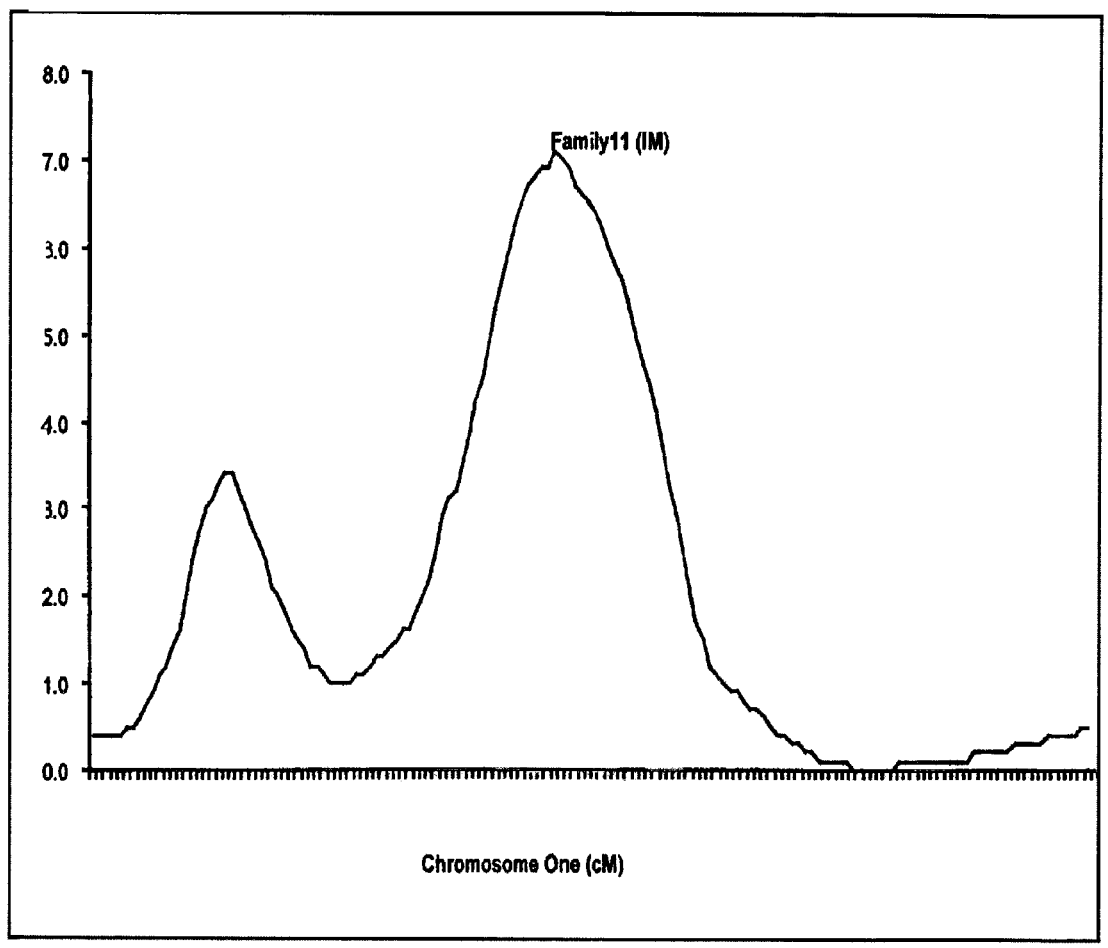
FIG. 10. The graph shows a likelihood ratio profile for bovine chromosome 1 analysis of Yield Grade (YG). The curve indicates significant Angus versus Brahman allele substitution effects in the vicinity of the SST locus in the progeny of Family 11, mothered by an $F_1$ cow, using IM.

FIG. 5 and FIG. 6 show the likelihood ratio profiles for marbling. FIG. 5 shows the correlation of the QTL with the chromosomal region that includes the SST locus, while FIG. 6 shows the positioning for the progeny of two different families. These profiles are strong evidence for the localization of the QTL influencing marbling to the region of chromosome 1 harboring the SST locus. FIG. 7 and FIG. 8 show the likelihood ratio profile for meat Quality Grade (QG). FIG. 7 shows the correlation of the QTL with the chromosomal region that includes the SST locus, while FIG. 8 shows the profile in the progeny of one family. FIG. 9 shows the likelihood ratio profile for Warner-Bratzler shear force (WBSH) under the infinite alleles model, and FIG. 10 shows the likelihood ratio profile for meat Yield Grade (YG) in one family. Thus, as indicated by FIGS. 2-10, QTLs have been localized to a chromosomal interval that harbors the SST locus on bovine chromosome 1.

The data in Tables 1 and 2, as well as FIGS. 2-10, clearly establish the influence of one or more genetic variations or polymorphisms located in the central region of chromosome 1 on a variety of QTLs, including at least weaning weight, hot carcass weight, ribeye muscle area, marbling, Quality Grade, Yield Grade, and Warner-Bratzler shear force. These traits are all associated with the growth of lean tissue and intramuscular fat. Specifically, meat Quality Grade is determined directly from the marbling score of the meat and meat Yield Grade is strongly influenced by hot carcass weight and ribeye muscle area. Because all of these QTLs are linked to the same chromosomal region, there may be a single genetic locus within the 1q32 region of bovine chromosome 1 that is responsible for the detected variation in all of these traits. A strong candidate gene for regulating growth and fat metabolism, the Somatostatin (SST) gene, maps to this region on chromosome 1 (FIG. 1).

To establish a more refined map of bovine chromosome 1, a total of 42 bovine microsatellites were genotyped in the resource families (see Ma et al., *J Heredity* 87:261-71, 1996; Barendse et al., *Mamm Genome* 8:21-28, 1997; and Kappes et al., *Genome Res* 7:235-49, 1997). One of the markers used to generate the more detailed map of chromosome 1 was a novel polymorphic microsatellite designated SSTms, which maps to the QTL region of chromosome 1. SSTms is a di-nucleotide repeat (GT)$_9$ microsatellite. Protocols for scoring genotypes and for the construction of the genetic map of chromosome 1 using CRI-MAP v2.4 (Green et al., *Documentation for CRI-MAP V2.4*, Washington University School of Medicine, St Louis, Mo., 1990) followed established procedures (see Beever et al., *Anim Genet* 27:69-75, 1996). The following genetic Sex-averaged map (recomb. frac., Kosambi cM) for chromosome 1 was constructed:

| 1 | 162M1 | 0.0 |
|---|---|---|
| 2 | AGLA17 | 0.0 |
| 3 | IFNAR | 0.7 |
| 4 | RACK17.2B7 | 1.5 |
| 5 | RACK17.2C6 | 1.5 |
| 6 | BM6438 | 1.5 |
| 7 | BM6438.29 | 1.7 |
| 8 | BM6438.34 | 1.7 |
| 9 | INRA212 | 2.5 |
| 10 | SOD1M2 | 2.6 |
| 11 | TGLA49 | 3.5 |
| 12 | ARO24 | 3.5 |
| 13 | ARO9 | 4.2 |
| 14 | BMS1928 | 6.4 |
| 15 | INRA117 | 7.0 |
| 16 | BM8139 | 8.3 |
| 17 | DIK70 | 14.8 |
| 18 | DV42 | 15.0 |
| 19 | RM95 | 22.5 |
| 20 | BM4307 | 36.7 |
| 21 | Pit17B7 | 38.9 |
| 22 | Pit16B6 | 38.9 |
| 23 | TGLA57 | 49.2 |
| 24 | TEXAN14 | 53.6 |
| 25 | BM1312 | 55.7 |
| 26 | BM6506 | 69.3 |
| 27 | SSTms | 70.7 |
| 28 | C126T | 70.7 |
| 29 | C157T | 70.7 |
| 30 | T244C | 70.7 |
| 31 | C575T | 70.7 |
| 32 | G981A | 70.7 |
| 33 | MGDFms | 73.5 |
| 34 | CSSM32 | 93.6 |
| 35 | TEXAN6 | 96.4 |
| 36 | BM1260 | 115.8 |
| 37 | BL28 | 123.2 |
| 38 | BM1824 | 124.5 |
| 39 | BM3205 | 127.7 |
| 40 | MAF46 | 129.6 |
| 41 | URB14 | 150.6 |
| 42 | URB56 | 150.9 |

The SST locus was a strong candidate gene for describing the observed QTLs that localize to the 1q32 region of bovine chromosome 1 because somatostatin appears to play a role in regulating growth and fat metabolism. Somatostatin is known to inhibit the release of hypophyseal hormones and mediate the action of these hormones via five receptor subtypes that are all present in the anterior pituitary. Somatostatin is also known to inhibit the release of growth hormone and has a key role in the pulsatile secretion of growth hormone from the pituitary (see Baile et al., *The neurophysiological control of growth*, In: P. J. Buttery, N. B. Haynes and D. B. Lindsay (ed.) Control and manipulation of animal growth, p. 105, Butterworths, London, 1986; Martin, *Pediat Adolesc Endocr* 12:1, 1983; Millard, *Central regulation of growth hormone secretion*, In: D. R. Campion, G. J. Hausman and R. J. Martin (ed.) Animal growth regulation, p. 237, Plenum Press, New York, 1989; Argente and Chowen, *Growth Genetics and Hormones* 10:1, 1994).

One study has demonstrated that immunization against somatostatin causes a significant increase in the rate of weight gain and final weight of lambs compared to controls (Spencer and Garssen, *Livest Prod Sci* 10:25, 1983). The immunized animals demonstrated heavier hot carcass weights and longer leg length, but no corresponding increase or decrease in fat or muscling content. These animals did, however, show an increase in feed conversion efficiency. Additional studies have reported increased growth rates in rams and wethers immunized against somatostatin, but found no effect in treated ewes (Mears, *J Anim Sci* 63:59, 1990).

Figure 11:
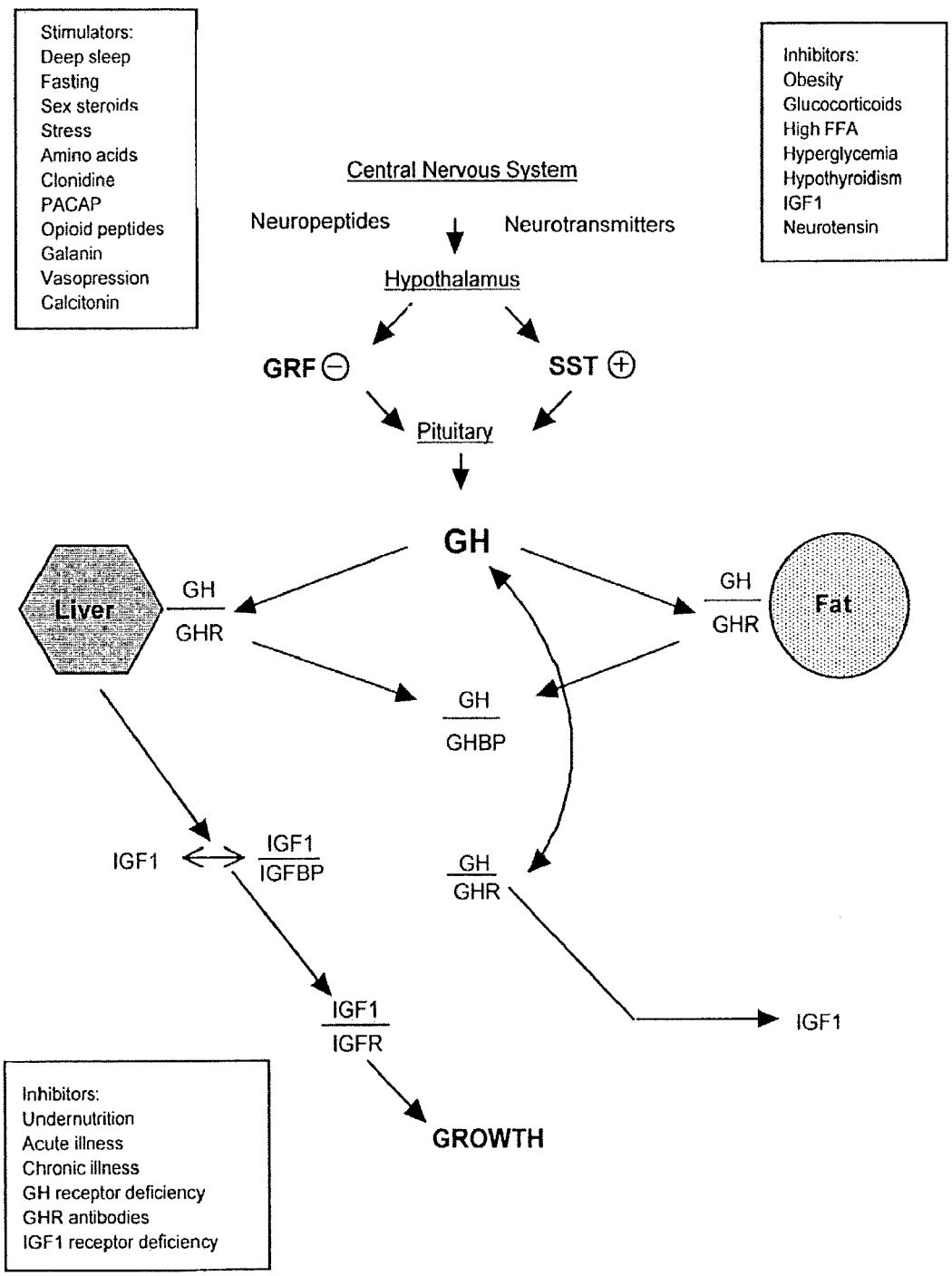
FIG. 11. Diagram of the Growth Hormone Axis, which illustrates the inter-relatedness of Somatostatin and various metabolic pathways to fat deposition and growth.

Somatostatin is a cyclic tetradecapeptide hormone found in the hypothalamus, digestive tract, thyroid, and other parts of the nervous system, including the brain. It is hypothesized that somatostatin affects weight gain and marbling of meat in cattle through its function in the growth hormone axis and its effects on fat metabolism. The term "growth hormone axis" as used herein refers to the genes in the biochemical pathways that involve growth hormone (see FIG. 11). Specifically, somatostatin functions within the growth hormone axis as an inhibitor of growth hormone. The principal actions of growth hormone can be divided into direct and indirect actions. The effects of growth hormone on carbohydrate and lipid metabolism represent the direct actions of the hormone, while the effects related to growth, including muscle and bone growth, as well as lipogenesis, are mediated indirectly through IGF-1.

IGF-1 is secreted by the liver in direct response to elevated levels of growth hormone. IGF-1 also functions to stimulate the release of somatostatin from the hypothalamus and to inhibit release of growth hormone from the pituitary (Baile et al., *The neurophysiological control of growth*, In: P. J. Buttery, N. B. Haynes and D. B. Lindsay (ed.) Control and manipulation of animal growth, p. 105, Butterworths, London, 1986; Kelly P. A., *Growth hormone and prolactin*, pp. 191-218 in Hormones: From molecules to disease, edited by E.-E. Baulieu and P. A. Kelly., Chapman and Hall, New York, 1990; Hadley M. E., *Endocrinology* 4th ed. Prentice Hall, Upper Saddle River, N.J., 1996). It is hypothesized that the effect of somatostatin on marbling is mediated either indirectly through the lipolytic effects of growth hormone or directly through the lipogenic effects of IGF-1.

After QTLs are linked to a particular chromosomal region using microsatellite markers, e.g. the SST locus in bovine, individual polymorphisms and genetic markers within and in genetic linkage with the locus can be analyzed to determine the linkage of a polymorphism or marker to a trait of interest. Comparison through, for example statistical analysis of the genetic markers, polymorphisms, and/or haplotypes in individuals with and without the desired traits will reveal the presence or absence of a particular marker, polymorphism, or haplotype in genetic linkage with the SST locus in the subject. As disclosed, the SST locus has been linked with a number of desirable traits in bovine. Based on this information, it is now within the skill of those in the art to perform linkage analysis studies of the SST locus with traits of interest not only in bovine, but also in a number of species of interest. Preferably, the traits examined in the species of interest are the same traits associated with the SST locus in bovine. The QTLs that have been linked with markers to the SST locus include marbling, hot carcass weight, ribeye muscle area, meat Quality Grade, Warner-Bratzler shear force, and Yield Grade. The species of interest that may be used for linkage analysis to identify genetic markers, polymorphisms, and haplotypes associated with traits of interest within and genetically linked to the SST locus include, but are not limited to, human, bovine, porcine, ovine, equine, rodent, avian, fish, and shrimp. Identifying polymorphisms linked with the SST locus and traits of interest is particularly preferred in livestock animals.

A person skilled in the art can readily identify and map the SST gene in any of the species of interest, for example, by using comparative genome maps. In fact, the SST gene already has been identified in many of these species, including human (Accession No. J00306), rat (Accession No. J00787), mouse (Accession No. X51468), cow (Accession No. U97077), pig (Accession No. U36385), sheep (Accession No. AF031488), chicken (Accession No. X60191), horse (Accession No. AF130783), and fish (Accession No. M25903, channel catfish; Accession No. AF126243, African lungfish). All accession numbers referred to herein are found in GenBank. Mammalian genomes are highly conserved in their chromosomal arrangement as well as in gene order (Andersson et al., *Science* 263:1771-1774, 1994). For example, Womack and Kata (*Curr Opin Genet Dev* 5:725-733, 1995) reported 70 segments of homology between cattle and human chromosomes involving a minimum of 40 rearrangements necessary to account for the observed divergence. Thus, the considerable homology between the physical maps of chromosomes in a number of species, including human, mouse, and bovine, has facilitated and will continue to facilitate the search for candidate genes corresponding to bovine QTLs in other species (see Solinas-Toldo et al., *Genomics* 27:489, 1995; DeBry and Seldin, *Genomics* 33:337-351, 1996; Eggen and Fries, *Anim Genet* 26:215-36, 1995). This homology also simplifies the mapping of a particular locus such as SST in other species for one of skill in the art. Thus, when the phenotypic impact of a gene on a certain trait or traits is known and the gene has been mapped in a number of species as with SST, identifying and mapping the gene in other species is simplified, and within the skill of one in the art.

Several techniques are available to those of skill in the art for building a comparative map. To facilitate the direct comparison of divergent species' gene maps, it is necessary that a group of homologous anchor loci be mapped in each species to serve as landmarks for the alignment of conserved segments. The best markers for such anchor loci are expressed genes, because these DNA sequences can be used to establish homology between divergent species. Large numbers of reference loci suitable for mapping in various species are known to those of skill in the art. Primer pair sequences are also known that can be used to amplify anchor loci by polymerase chain reaction (PCR). Comparative maps continue to provide remarkably reliable linkage predictions. For example, the ZOO-FISH method, which is the comparative painting of chromosomes between species, is a powerful technique for identifying homologous chromosomal segments between human and cattle (Solinas-Toldo et al., *Genomics* 27:489, 1995; Chowdhary et al., *Mamm Genome* 7:297-302, 1996).

Many methods are known to those of skill in the art to identify and map a gene, particularly when the gene has already been identified in a number of species. For example, a cDNA for the SST gene can be isolated by screening a cDNA library with SST locus DNA from another species, SST locus DNA from the same species, or a DNA fragment amplified by PCR using primers in conserved regions of the SST gene. The SST gene can also be isolated using sequence information found in EST databases and GenBank. The cDNA clone or SST DNA fragment can be used to screen a DNA library of the species of interest, including but not limited to genomic DNA libraries, microdissected chromosome DNA libraries, BAC libraries, YAC libraries, PAC libraries, phage libraries, phosmid and cosmid libraries. The SST locus is found in a relatively compact genomic region in human, rat, and bovine, which suggests that isolating and analyzing the genomic DNA clone of the SST locus in other species, will not be difficult for those of skill in the art.

After genomic DNA, cDNA, or a DNA fragment with all or part of the SST locus is isolated, it can be used to map the gene on a chromosome. The DNA sequence of the SST locus can also be analyzed to identify genetic variations and/or polymorphisms using a variety of methods known to those of skill in the art. Many methods for mapping the location of a locus in a species are known to those of skill in the art, including but not limited to FISH, linkage mapping, physical mapping, radiation hybrid (RH) mapping (Cox et al., *Science* 250:245-250, 1990), somatic cell hybrid (SCH) mapping (Weiss and Green, *Proc Natl Acad Sci USA* 58:1104-1111, 1976), inner product mapping (IPM) (Perlin and Chakravarti, *Genomics* 18:283-289, 1993), restriction fragment fingerprint mapping (Bellanne-Chantelot et al., *Cell* 70:1059-1068, 1992; Stallings et al., *Proc Natl Acad Sci USA* 87:6218-6222, 1990; Coulson et al., *Proc Natl Acad Sci USA* 83:7821-7825, 1986), and other methods well known to those of skill in the art, depending on the mapping resolution desired.

Additionally, one of skill in the art can sequence the DNA with the SST locus so that the sequence and organization of the SST locus can be compared with the sequence and organization of the SST locus in other species, as well as in other individuals within the same species. After polymorphisms are identified in the SST locus by sequence analysis, these polymorphisms can be compared in many individuals in the species of interest, and statistical analysis can be used to correlate the presence of certain genetic variations and/or polymorphisms with one or more QTLs of interest. Preferably, genetic linkage of polymorphisms and/or genetic variations in the SST locus to traits such as marbling, hot carcass weight, ribeye muscle area, meat Quality Grade, Warner-Bratzler shear force, flavor, juiciness, and Yield Grade, is analyzed. The statistical analysis can be performed using methods and computer programs disclosed herein, or methods and programs well known to those of skill in the art. Statistical analysis can be performed either on animals in the same family, the same breed, different breeds, or in the general population of the species of interest.

Additionally, genetic markers that are linked to the SST locus can be identified after the chromosomal location of the locus is determined. A variety of methods are known to those of skill in the art for identifying markers linked to a desired locus and/or a desired QTL. For example, one of skill in the art can use standard methods to acquire novel microsatellites from cloned genomic DNA, such as for example BAC clones (see Hillis et al., 1996, Nucleic Acids IV: Sequencing and cloning, pp. 321-84 in *Molecular Systematics*, edited by Hillis, Moritz, and Mable, Sinauer Associates, Inc., Sunderland, Mass.). Once a marker is identified that is linked to the SST locus, statistical analysis can be used to correlate the presence of the marker with one or more QTLs. The following illustration outlines a method for identifying markers, such as microsatellites (for example, di-nucleotide repeats and tri-nucleotide repeats, as well as RFLP markers, linked to the SST locus (see U.S. Pat. No. 5,582,979, incorporated herein by reference).

The usefulness of genetic markers in genetic linkage with the SST locus will be maximized by screening genomic clones for microsatellite repeats, for example $(GT)_n$ repeat sequences. Genetic markers can be analyzed individually or in combination. To analyze these markers, a small segment(s) of DNA can be amplified using PCR which contains the block of repeats and some non-repeated flanking DNA, and sizing the resulting amplified DNA, preferably by electrophoresis on polyacrylamide gels. Additionally, sequence information necessary for primer production can be determined through the isolation of DNA fragments, preferably as clones, for example, that contain the $(GT)_n$ repeats by hybridizing a synthetic, cloned, amplified, or genomic DNA fragment that contains a sequence that is substantially homologous to the tandemly repeated sequence $(GT)_n$. In a preferred embodiment, the probe would be labeled, for example by end labeling, internal labeling, or nick translation.

The development of a polymorphic genetic marker based on length variations involves a series of steps. First, primers are identified that will amplify a region of genomic DNA that has one or more polymorphic markers that are in genetic linkage with the SST locus. To identify useful primers that flank a repeat, genomic clones are made or isolated from the chromosomal region of the SST locus. Genomic clones that map back to the SST region are digested with a restriction endonuclease; subjected to gel electrophoresis; and hybridized to an oligonucleotide with a short nucleotide repeat. Preferably the oligonucleotide will have a di-nucleotide repeat, such as (GT), or a tri-nucleotide repeat. The bands that hybridize with the repeat oligonucleotide are subcloned and sequenced, and primers are generated that correspond to the unique sequences flanking the repeat regions (see Weber, *Genomics* 7:524-530, 1990). Alternatively, one of skill in the art can design primers based on a suitable sequence in the literature or databases such as GenBank. The primers are then used to amplify DNA from individuals to determine whether the repeat polymorphism of interest is present or absent. The repeat polymorphism, or the SST locus the repeat polymorphism is in genetic linkage with, may be able to predict the phenotype of an animal.

Primers designed to amplify DNA will preferably not have any obvious self-homologies, nor runs of the same nucleotide, and are preferably not overly G:C or A:T rich. It is understood that these letter designations represent G for guanine, A for adenine, T for thymine, and C for cytosine nucleotides. A primer that contains self-homologies or sequences in one region that are complementary to sequences in another region of the primer will form internal hairpin duplexes and thus would be unavailable to hybridize with the target DNA. Also, since G:C pairing involves 3 hydrogen bonds and A:T pairing involves 2 hydrogen bonds, a primer with a disproportionately high content of the nucleotides G or C, singly or in combination, will have a higher melting temperature than a primer that was comprised of a higher content of A and T. Simple formulae for determining the melting temperature of a primer based on its G:C content are well known in the art. The optimal annealing temperature of a primer can be calculated by one of skill in the art using a variety of available computer software programs, such as Oligo Analyzer, which is available at the website http://www.idtdna.com. One of skill in the art may also incorporate one or more restriction enzyme sites into primers for subsequent cloning of amplified products into plasmids.

In a preferred embodiment of identifying a $(GT)_n.(CA)_n$ microsatellite marker linked to the SST locus, total genomic DNA from an organism or total DNA from a chromosome large insert phage library of the chromosome containing the SST locus (for example chromosome 1 in bovine), is digested to completion with a restriction enzyme that cuts frequently, for example Sau3A I, Alu I, Taq I, or a combination of Sau3A I and Taq I. DNA fragments ranging in size from about 150 to 400 base pairs are purified by preparative agarose gel electrophoresis, and ligated into a vector. The subcloned DNA fragments are next screened by hybridization to labeled synthetic $poly(CA)_n.poly(GT)_n$. The DNA identified in the positive clones is isolated and sequenced. The sequence information can then be used to design primers that will amplify the polymorphic repeat sequences.

The use of RFLPs is another preferred embodiment of detecting genetic markers and polymorphism. RFLP analysis of DNA polymorphisms relies on variations in the lengths of DNA fragments produced by restriction enzyme digestion.

Most of these RFLPs involve sequence variations in one of the recognition sites for the specific restriction enzyme used. Methods for detecting RFLPs are well known to those of skill in the art. RFLPs can be identified, for example, by restriction enzyme analysis using a particular enzyme or enzymes, or performing a Southern hybridization procedure with the desired probe. The nucleotide probes may be RNA or DNA, preferably DNA, and can be labeled using standard labels, including but not limited to radiolabel, enzyme label, fluorescent label, and biotin-avidin label, which can be detected after hybridization (for example, see Leary et al., *Proc Natl Acad Sci USA* 80:4045, 1983). The use of RFLPs in linkage analysis and genetic testing is well known in the art (see Gusella, U.S. Pat. No. 4,666,828, incorporated herein by reference; and Donis-Keller et al., *Cell* 51:319-337, 1987). Since the use of RFLPs depends on polymorphisms in an individual's DNA, any method capable of detecting the polymorphisms can also be used. Techniques such as amplification of a desired region of the chromosome coupled with direct sequencing, or location of polymorphisms on the chromosome by radiolabeling, fluorescent labeling, or enzyme labeling, can also be utilized.

If the genetic sample to be analyzed is present in limited amounts, the genetic material in the sample may be amplified to increase the amount of genetic material that can be analyzed, as well as increase the available material for subsequent analysis, for example SNP, RFLP, or sequence analysis. There are a number of methods well known to those of skill in the art for amplifying DNA and other genetic material. Genetic material from very small samples, even single cells such as a sperm or ova, may be amplified for genotype analysis. For example, a sperm sample can be isolated from an animal and genotype analysis can be performed on the sperm to determine whether any desirable or undesirable polymorphisms are found in the sperm population.

Methods for generating additional new DNA fragments that are linked to the SST locus are as follows. First, DNA fragments can be isolated by identifying fragments that are in genetic linkage with other markers that have already been mapped to the SST locus region. The polymorphism that is a new genetic marker can then be tested for linkage to the SST locus and desired QTLs. A probe used to detect a particular marker or polymorphism can be of any desired sequence length as long as it is capable of identifying the marker or polymorphism in the involved DNA region or locus. The probe can be DNA or RNA, the fragment by itself or in longer genetic sequences or fragments, or in a plasmid or other appropriate vehicle. Labeling and hybridization conditions can be readily determined by those of skill in the art, and a detailed discussion of nucleic add hybridization technology can be found in Nucleic Acid Hybridization, Hames et al., eds., IRL Press, Washington, D.C., 1985. Probes may also be synthesized chemically or enzymatically, and may be obtained and replicated by insertion into a plasmid using techniques known to those of skill in the art (Molecular Cloning, a Laboratory Manual, 2nd ed., 1989, Sambrook, Fritsch, and Maniatis, Cold Spring Harbor Laboratory Press).

Linkage disequilibrium, or allelic association, refers to the tendency of specific alleles for different marker loci within a tightly linked group to occur together more frequently than would be expected by chance. Ordinarily, alleles at linked loci are expected to be equilibrium; that is, the frequency of any particular set of alleles will be the product of their individual population frequencies. Linkage disequilibrium is important because often the contributing genetic feature of a trait or disease is not known or measured directly. Contributing features are genetic variations such as SNPs and other polymorphisms that have a direct functional, biochemical, or clinical effect, and are more general than causative mutations, which imply that a single variation is responsible for a phenotype. (Judson and Stephens, *Pharmacogenomics* 2:7-10, 2001). The cause of linkage disequilibrium is often unclear, and can be due to selection for certain allele combinations, or to the recent admixture of genetically heterogeneous populations. Additionally, with genetic markers or alleles that are tightly linked to a polymorphism, an association of a genetic marker or allele (or group of linked alleles) with the polymorphism is expected if the polymorphism is due to a mutation that occurred in the recent past, so that sufficient time has not elapsed for equilibrium to be achieved through recombination events in that small chromosomal region.

With linkage disequilibrium, genetic markers or polymorphisms that are distant from a genetic locus or contributing feature in the genome may still be predictive of an animal's likelihood of inheriting a certain trait because large regions of DNA that are in linkage disequilibrium (e.g. a haplotype) are inherited together. A haplotype is defined by alleles, loci, genetic markers, polymorphisms, and/or other genetic variations that are inherited together as a group (i.e. are in linkage disequilibrium), and can be predictive of an animal's likelihood of having a particular trait of interest. Thus, a haplotype can be the DNA sequence for a genomic locus found on one of an individual's chromosomes, as well as a collection of nucleotides at SNP sites within the locus (Judson and Stephens, supra). Haplotypes may be of great length, including up to tens of centimorgans. For example, a microsatellite marker or genetic variation that is newly identified may be used to detect the presence of an already known haplotype defined by SNPs or genetic markers because of linkage disequilibrium. Haplotypes that are defined for example by SNPs or genetic markers are often conserved across a region in a species. Identifying haplotypes is advantageous when the contributing SNP(s) or genetic marker(s) is not known or directly observed, as long as the contributing SNP(s) or genetic marker(s) is within the defined haplotype (Judson and Stephens, supra). Contributing polymorphisms will often reside on one or a few of the individual haplotypes within a locus.

The term "locus" as used herein can refer to a single gene or a portion of a gene such as a SNP, or locus can refer to the chromosomal location of any characterized DNA sequence. The term "gene" as used herein refers to the entire DNA sequence of a unit of heredity, including but not limited to exons, introns, 5' untranslated region, 3' untranslated region, regulatory elements, and non-coding transcription-control regions. The term "allele" as used herein refers to alternative forms of a gene at a particular nucleotide or marker. When a subject has two identical alleles at a particular nucleotide or marker, the subject is said to be homozygous. When a subject has two different alleles, the subject is said to be heterozygous. The coexistence of more than one form of a gene or portion (e.g., allelic variant) of a gene is referred to as a polymorphism. A polymorphism can be a SNP, the identity of which differs in different alleles, or a polymorphism can be several nucleotides in length. Polymorphism also include, but are not limited to STRs, RFLPs, VNTRs, CTRs, microsatellites, deletions, substitutions, and insertions.

In bovine, extensive genome-wide linkage disequilibrium has been found, and can extend over tens of centimorgans (Farnir et al., *Genome Res* 10:220-227, 2000; Vage et al., *Animal Genet* 23:125-132, 1992). The high degree of linkage disequilibrium in bovine between syntenic loci using marker maps also suggests that linkage disequilibrium is extensive in livestock populations. Given the linkage disequilibrium found in bovine, even a genetic marker or polymorphism that is quite distant from the contributing feature for a QTL may nevertheless be linked to the trait of interest, and therefore predictive of the animal's phenotype. Therefore, a haplotype that is linked to a trait(s) of interest in bovine can be used to screen the general population (see Riquet et al., *Proc Natl Acad Sci USA* 96:9252-57, 1999). Indeed, extensive linkage disequilibrium has been found in a number of species, including humans (Moffat et al., *Hum Mol Genet* 7:1011-1019, 2000; Reich et al., *Nature* 411:199-204, 2001; Bonnen et al., *Am J Hum Genet* 67:1437-1451, 2000). For example, linkage disequilibrium over distances of up to 400 kb (which is on average only about 0.4 centimorgans) has been found for microsatellite markers in humans (Koch et al., *Hum Mol Genet*, 9:2993-2999, 2000).

Once polymorphisms and genetic markers are identified that are genetically linked or a contributing feature of certain traits in a species of interest, animals in the general populations may be screened and selected based on their genetic profile with respect to these polymorphisms and markers. The first step in analyzing the genotype of an animal is to isolate nucleic acid samples from the animal for analysis. Nucleic acid samples suitable for genotype analysis include but are not limited to tissue or blood containing genomic DNA suitable for genotype analysis. These samples may be conveniently obtained from, for example, buccal swab, nose swab, hair, mouthwash, cord blood, amniotic fluid, embryonic tissue, endothelial cells, hoof clippings, or fingernail clipping. Genomic DNA in paraffin-embedded tissue may also be analyzed. With more limited samples, DNA amplification methods can be used to generate additional material for analysis, for example from a single cell, including but not limited to a single cell isolated from a pre-implantation embryo, fetal cells in the peripheral blood of pregnant animal, sperm, or oocytes, or a single cell from any tissue. A single cell may be isolated using a variety of methods, including flow cytometry (Herzenberg et al., *Proc Natl Acad Sci USA* 76:1453-55, 1979; Iverson et al., *Prenatal Diagnosis* 1:61-73, 1981; Bianchi et al., *Prenatal Diagnosis* 11:523-28, 1991), which can utilize fluorescent activation cell sorting (FACS), magnetic-activated cell sorting (MACS, Ganshirt-Ahlert et al., *Am J Obstet Gynecol* 166:1350, 1992), or a combination of both procedures. Additionally, a combination of gradient centrifugation and flow cytometry methods can also be used to increase isolation or sorting efficiency.

The present disclosure also contemplates the variety of solid media well known to those of skill in the art for storing samples and nucleic acid material, including tissue and blood samples. Preferably, the solid medium is dry, and has a solid matrix or solid support, such as preferably an absorbent cellulose-based paper (such as filter paper), or a micromesh of synthetic plastic materials. The solid matrix may also be in the form of a tablet or pellet. Preferably the solid medium will protect against the degradation of the DNA sample incorporated or absorbed on the matrix or support. A solid medium allows DNA samples to be stored and transported in a form suitable for the recovery of the DNA in the sample for analysis. Samples can be collected and stored for example on FTA™ paper, Whatmann® paper, Guthrie cards, swabs, and filter paper.

Genotype analysis of samples of nucleic acid material may be performed using a variety of methods and techniques that are well known to those of skill in the art. For example, methods of high-throughput screening can allow large numbers of organisms to be rapidly screened for diagnostic or research purposes. The term "genotype analysis" refers to any type of genetic typing, genotyping, fingerprinting, haplotyping, DNA typing, or any similar phrase. The term includes the use of any methods or protocols known to those of skill in the art for determining an individual's genotype at one or more genetic loci, including identifying haplotypes. Techniques that are nucleic acid based include but are not limited to size fractionation; SNP, RFLP, VNTR, STR, CTR, and microsatellite analysis; allele specific oligonucleotide (ASO) hybridization; sequencing; denaturation temperature analysis; and mass spectrometry analysis. Methodologies available to those of skill in the art are numerous and continually developing, and cannot be detailed herein.

Polymorphisms, for example SNPs, that are identified as being associated with a trait of interest can be screened using a variety of techniques well known to those of skill in the art. SNPs are stable nucleotide sequence variations at a specific location in the genome of different individuals. SNPs are of predictive value in identifying many genetic diseases, as well as phenotypic characteristics that may be desirable, which are often caused by a limited number of different mutations in a population. SNPs are found in both coding and non-coding regions of genomic DNA, and are found in large numbers throughout the human genome (Cooper et al., *Hum Genet* 69:201-205, 1985). Certain SNPs result in disease-causing mutations such as, for example, heritable breast cancer (Cannon-Albright and Skolnick, *Semin Oncol* 23:1-5, 1996). Current methods of screening for polymorphisms are known (see for example U.S. Pat. Nos. 6,221,592 and 5,679,524).

A SNP may be identified in the DNA of an organism by a number of methods well known to those of skill in the art, including but not limited to identifying the SNP by PCR or DNA amplification, Oligonucleotide Ligation Assay (OLA) (Landegren et al., *Science* 241:1077, 1988), Doublecode OLA (described in U.S. App. Ser. No. 09/755,628, incorporated herein by reference), mismatch hybridization, mass spectrometry, Single Base Extension Assay, RFLP detection based on allele-specific restriction-endonuclease cleavage (Kan and Dozy, *Lancet* ii:910-912, 1978), hybridization with allele-specific oligonucleotide probes (Wallace et al., *Nucl Acids Res* 6:3543-3557, 1978), including immobilized oligonucleotides (Saiki et al., *Proc Natl Acad Sci USA* 86:6230-6234, 1989) or oligonucleotide arrays (Maskos and Southern, *Nucl Acids Res* 21:2269-2270, 1993), allele-specific PCR™ (Newton et al., *Nucl Acids Res* 17:2503-16, 1989), mismatch-repair detection (MRD) (Faham and Cox, *Genome Res* 5:474-482, 1995), binding of MutS protein (Wagner et al., *Nucl Acids Res* 23:3944-3948, 1995), single-strand-conformation-polymorphism detection (Orita et al., *Genomics* 5:874-879, 1983), RNAase cleavage at mismatched base-pairs (Myers et al., *Science* 230:1242, 1985), chemical (Cotton et al., *Proc Natl Acad Sci USA* 85:4397-4401, 1988) or enzymatic (Youil et al., *Proc Natl Acad Sci USA* 92:87-91, 1995) cleavage of heteroduplex DNA, methods based on allele specific primer extension (Syvanen et al., *Genomics* 8:684-692, 1990), genetic bit analysis (GBA) (Nikiforov et al., *Nuci Acids Res* 22:4167-4175, 1994), and radioactive and/or fluorescent DNA sequencing using standard procedures well known in the art.

A Single Base Extension Assay is performed by annealing an oligonucleotide primer to a complementary nucleic acid, and extending the 3' end of the annealed primer with a chain terminating nucleotide that is added in a template directed reaction catalyzed by a DNA polymerase. The selectivity and sensitivity of a single base primer extension reaction are affected by the length of the oligonucleotide primer and the reaction conditions (e.g. annealing temperature, salt concentration). The selectivity of a primer extension reaction reflects the amount of exact complementary hybridization between an oligonucleotide primer and a nucleic acid in a sample. A highly selective reaction promotes primer hybridization only to nucleic acids with an exact complementary sequence (i.e. there are no base mismatches between the hybridized primer and nucleic acid). In contrast, in a non selective reaction, the primer also hybridizes to nucleic acids with a partial complementary sequence (i.e. there are base mismatches between the hybridized primer and nucleic acid). In general, parameters which favor selective primer hybridization (for example shorter primers and higher annealing temperatures) result in a lower level of hybridized primer. Therefore, parameters which favor a selective single base primer extension assay result in decreased sensitivity of the assay.

Additionally, cycled Single Base Extension Reactions may be performed by annealing a nucleic acid primer immediately 5' to a region containing a single base to be detected. Two separate reactions are conducted. In the first reaction, a primer is annealed to the complementary nucleic acid, and labeled nucleic acids complementary to non-wild-type variants at the single base to be detected, and unlabeled dideoxy nucleic acids complementary to the wild-type base, are combined. Primer extension is stopped the first time a base is added to the primer. Presence of label in the extended primer is indicative of the presence of a non-wild-type variant. A DNA polymerase, such as Sequenase™ (Amersham), is used for primer extension. In a preferred embodiment, a thermostable polymerase, such as Taq or thermal sequenase is used to allow more efficient cycling. Once an extension reaction is completed, the first and second probes bound to target nucleic acids are dissociated by heating the reaction mixture above the melting temperature of the hybrids. The reaction mixture is then cooled below the melting temperature of the hybrids and additional primer is permitted to associate with target nucleic acids for another round of extension reactions. After completion of all cycles, extension products are isolated and analyzed. Alternatively, chain-terminating methods other than dideoxy nucleotides may be used. For example, chain termination occurs when no additional bases are available for incorporation at the next available nucleotide on the primer.

A particularly powerful means of analyzing genetic information from DNA amplified using the disclosed methods is DNA chip technology. DNA chips and microarrays comprising arrays of oligonucleotide or polynucleotide probes can be used to determine whether a target nucleic acid has a nucleotide sequence identical to or different from a specific reference sequence. The basic chip or microarray encompasses an array of oligonucleotide or polynucleotide probes immobilized on a solid support. Chips for screening and detection are designed to contain probes exhibiting complementarity to one or more selected sequences whose sequence is known. Chips are used to read a target sequence comprising either the reference sequence itself or variants of that sequence. Target sequences may differ from the reference sequence at one or more positions but show a high overall degree of sequence identity with the reference sequence (e.g., at least 75, 90, 95, 99, 99.9, or 99.99%). Hybridization of a target sequence to an immobilized probe results in a detectable signal. Signal can be delivered for example by conformational changes occurring in the probe, quenching or excitation of a label incorporated into the bound probe, or by quenching or excitation of a label incorporated into the target. Signal delivery may be read manually, mechanically, or digitally. A number of patents, herein incorporated by reference, disclose the preparation and use of DNA chips and microarrays including: U.S. Pat. Nos. 5,837,832, 6,156,501, 6,174,683, and 5,985,567. Additionally, allele specific primer extension can be combined with primer arrays for high-throughput genotyping of SNPs (see Pastinen et al., *Genome Res* 10 (7):1031-42, 2000).

In the context of the present disclosure, it is specifically contemplated that nucleic acid samples of animals in a population, preferably bovine animals, may be analyzed using DNA chips or microarrays in order to detect specific genetic sequences, including genetic polymorphisms or genetic variations, such as for example SNPs. In one embodiment, it is envisioned that genomic DNA will be amplified in order to produce a library of DNA sequences theoretically encompassing the entire genomic sequence. The amplified DNA products may then be passed over a DNA chip or microarray encompassing oligonucleotide or polynucleotide probes. The ability or inability of the amplified DNA to hybridize to the microarray or DNA chip will facilitate the characterization of the specific sequences and their polymorphisms present in the DNA sample.

It is also contemplated in the context of the present disclosure that samples of nucleic acid material will be isolated from species or organisms of interest and analyzed to determine the likelihood that an animal has or will have a particular trait of interest. These samples will also allow practitioners of skill in the art to carry out the methods of the present disclosure. In one preferred embodiment, the sample of nucleic acid material is genomic DNA, microdissected chromosome DNA, yeast artificial chromosome (YAC) DNA, PI derived artificial chromosome (PAC) DNA, cosmid DNA, phage DNA, or bacterial artificial chromosome (BAC) DNA. In another preferred embodiment, the sample of nucleic acid material is tissue, blood, or a single cell. Preferably the sample is readily and easily obtained from an organism, and is easy to store. The sample can be obtained from any species or organism, including but not limited to human, mammal, bovine, porcine, ovine, equine, rodent, avian, fish, and shrimp.

The methods and preferred embodiments of the present disclosure have been described above. Many techniques and methods are well known to those of skill in the art and may be used to assist practitioners in carrying out the methods of the present disclosure. The following is a general description of some of these techniques.

Nucleic Acids:

Genes are sequences of DNA in an organism's genome encoding information that is converted into various products making up a whole cell. They are expressed by the process of transcription, which involves copying the sequence of DNA into RNA. Most genes encode information to make proteins, but some encode RNAs involved in other processes. If a gene encodes a protein, its transcription product is called mRNA ("messenger" RNA). After transcription in the nucleus (where DNA is located), the mRNA is transported into the cytoplasm for the process of translation, which converts the code of the mRNA into a sequence of amino acids to form protein. In order to direct transport of mRNA into the cytoplasm, the 3' ends of mRNA molecules are post-transcriptionally modified by the addition of several adenylate residues to form the "polyA" tail. This characteristic modification distinguishes gene expression products destined to make protein from other molecules in the cell, and thereby provides one means for detecting and monitoring the gene expression activities of a cell.

1. Oligonucleotide Probes and Primers:

Nucleic acid sequences that are "complementary" are those that are capable of base-pairing according to the standard Watson-Crick complementary rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing. As used herein, the term "complementary" sequences means nucleic acid sequences that are substantially complementary, as may be assessed by the same nucleotide comparison set forth above, or as defined as being capable of annealing to the nucleic acid segment being described under relatively stringent conditions.

The term "primer" as used herein is meant to encompass any nucleic acid that is capable of priming the synthesis of a nascent nucleic acid in a template-dependent process. Sequence specific primers should be of sufficient length to provide specific annealing to the targeted RNA or DNA sequence. The use of a primer of between about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 75, 80, 85, 90, 95, and 100 or more nucleotides in length allows the formation of a duplex molecule that is both stable and selective, although shorter and longer primers are specifically contemplated in the context of the present disclosure. Complementary sequences over stretches greater than 20 bases in length are generally preferred for amplification in order to increase stability and selectivity of hybridization.

Although shorter primers are easier to make and increase in vivo accessibility, numerous other factors are involved in determining the specificity of hybridization. Both binding affinity and sequence specificity of a primer to its complementary target increases with increasing length. It is contemplated that exemplary primers of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 75, 80, 85, 90, 95, and 100 or more nucleotide base pairs will be used, although others are contemplated as well. Accordingly, nucleotide sequences may be selected for their ability to selectively form duplex molecules with complementary stretches of genes, DNA, or RNA, or more specifically to provide primers for amplification of DNA or RNA preparations including DNA or RNA directly or indirectly derived from cells, cell lysates, and tissues. Probes and primers of the present disclosure are used to amplify DNA, as well as detect genes, changes in gene expression, gene polymorphisms, single nucleotide polymorphisms, and changes in mRNA expression where one could be detecting virtually any gene or genes of interest from any species. The target polynucleotide will be RNA molecules, mRNA, cDNA, DNA, or amplified DNA. By varying the stringency of annealing, and the region of the primer, different targets may be discovered.

Primers may be chemically synthesized by methods well known within the art. Chemical synthesis methods allow for the placement of detectable labels such as fluorescent labels, radioactive labels, etc. to be placed virtually anywhere within the polynucleic acid sequence. Solid phase methods as well as other methods of oligonucleotide or polynucleotide synthesis known to one of ordinary skill may used within the context of the disclosure. It is specifically contemplated that a wide variety of appropriate detection or recognition means are known in the art and may be incorporated into the primers. Such labels may include, but are not limited to: fluorescent labels, radioactive labels, mass labels, affinity labels, chromophores, dyes, electroluminescence, chemiluminescence, enzymatic tags, or other ligands, such as avidin/biotin, or antibodies, which are capable of being detected and are described below.

2. DNA Amplification:

One of the best known amplification methods is PCR™, which is described in detail in U.S. Pat. Nos. 4,683,195, 4,683,202 and 4,800,159. In PCR™, pairs of primers that selectively hybridize to nucleic acids are used under conditions that permit selective hybridization. The term primer, as used herein, encompasses any nucleic acid that is capable of priming the synthesis of a nascent nucleic acid in a template-dependent process. Primers may be provided in double-stranded or single-stranded form, although the single-stranded form is preferred. The primers are used in any one of a number of template dependent processes to amplify the target-gene sequences present in a given template sample.

The nucleic acid target for the disclosed DNA amplification method is generally considered to be any nucleic acid or nucleic acid analog capable of being amplified by techniques well known in the art. By way of example, target nucleic acids specifically contemplated in the context of the disclosure, may include, but are not limited to: genomic DNA, cDNA, RNA, mRNA, cosmid DNA, BAC DNA, PAC DNA, YAC DNA, and synthetic DNA. In a contemplated embodiment, poly-A mRNA is isolated and reverse transcribed (referred to as RT) to obtain cDNA, which is then used as the template for DNA amplification. In other contemplated embodiments, cDNA may be obtained and used as the template DNA to be amplified. In still another embodiment, RNA or mRNA is directly amplified.

The necessary reaction components for DNA amplification are well known to those of skill in the art. It is also understood by those of skill in the art that the temperatures, incubation periods, and ramp times of the DNA amplification steps, such as denaturation, hybridization, and extension, may vary considerably without significantly altering the efficiency of DNA amplification and other results. Alternatively, those of skill in the art may alter these parameters to optimize the DNA amplification reactions. These minor variations in reaction conditions and parameters are included within the scope of the present disclosure.

i. PCR™

In PCR™ two primer sequences are prepared which are complementary to regions on opposite complementary strands of the target sequence. The primers will hybridize to form a DNA:primer hybrid if the target sequence is present in a sample. An excess of deoxyribonucleoside triphosphates are added to a reaction mixture along with a DNA polymerase, e.g., Taq polymerase, that facilitates template-dependent nucleic acid synthesis. If the DNA:primer hybrid is formed, the polymerase will cause the primers to be extended along the target sequence by adding on nucleotides. By raising and lowering the temperature of the reaction mixture, the extended primers will dissociate from the target sequence to form reaction products, excess primers will bind to the target sequence and to the reaction products, and the process is repeated. These multiple rounds of amplification, referred to as "cycles," are conducted until a sufficient amount of amplification product is produced.

Next, the amplification product is detected. In certain applications, the detection may be performed by visual means. Alternatively, the detection may involve indirect identification of the product via fluorescent labels, chemiluminescence, radioactive scintigraphy of incorporated radiolabel or incorporation of labeled nucleotides, mass labels, or even via a system using electrical or thermal impulse signals.

ii. LCR

Another method for amplification is the ligase chain reaction ("LCR"), disclosed in European Patent Application No. 320,308. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750, incorporated herein by reference, describes a method similar to LCR for binding probe pairs to a target sequence.

iii. LAM-PCR

In linker adaptor-mediated PCR (LAM-PCR), which is another method of DNA amplification, the starting DNA is first digested with a restriction enzyme, usually an enzyme with a four-base recognition sequence. After inactivation of the restriction enzyme, a known sequence (either an adaptor or a synthetic linker) is ligated to the ends of the DNA fragments generated by the restriction-enzyme digest, providing primer binding sites for PCR amplification. The DNA can then be amplified by PCR using primers that are complementary to the sequence of the adaptor or linker. LAM-PCR has been applied to microdissected chromosomes (Zhou et al., *Bio Techniques* 28:766-774, 2000; Albani et al., *Plant J* 4(5): 899-903, 1993), yeast artificial chromosome (YAC) DNA (Sutcliffe et al., *Genomics* 13(4):1303-6, 1992), and genomic DNA (Kinzler et al., *Nucleic Acids Res* 25:17(10):3645-53, 1989).

iv. Qbeta Replicase

Qbeta Replicase, described in PCT Patent Application No. PCT/US87/00880, also may be used as another amplification method in the present disclosure. In this method, a replicative sequence of RNA that has a region complementary to that of a target is added to a sample in the presence of an RNA polymerase. The polymerase will copy the replicative sequence which can then be detected.

v. Isothermal Amplification

An isothermal amplification method, in which restriction endonucleases and ligases are used to achieve the amplification of target molecules that contain nucleotide 5'-[α-thio]-triphosphates in one strand of a restriction site also may be useful for DNA amplification. Such an amplification method is described by Walker et al. (*Nucleic Acids Res* 20(7):1691-6, 1992).

vi. Strand Displacement Amplification

Strand Displacement Amplification (SDA) is another method of carrying out isothermal amplification of nucleic acids which involves multiple rounds of strand displacement and synthesis, i.e., nick translation. The SDA technique is described in U.S. Pat. Nos. 5,712,124, 5,648,211 and 5,455,166, incorporated herein by reference. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA.

vii. Cyclic Probe Reaction

Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products are released after digestion. The original template is annealed to another cycling probe and the reaction is repeated.

viii. Transcription-Based Amplification

Other nucleic acid amplification procedures specifically contemplated in the context of the present disclosure include transcription-based amplification systems (rAS), including nucleic acid sequence based amplification (NASBA) and 3SR, Kwoh et al., *Proc Natl Acad Sci USA,* 86:1173-77, 1989; PCT Patent Application WO 88/10315 et al., 1989.

In NASBA, the nucleic acids can be prepared for amplification by standard phenol/chloroform extraction, heat denaturation of a nucleic acid sample, treatment with lysis buffer, and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by a polymerase such as T7 or SP6. In an isothermal cyclic reaction, the RNAs are reverse transcribed into double stranded DNA, and transcribed once again with a polymerase such as T7 or SP6. The resulting products, whether truncated or complete, indicate target specific sequences.

ix. DOP-PCR

A method called degenerated oligonucleotide-primed PCR (DOP-PCR) utilizes partially degenerated sequence (6 out of 21) and repeated thermocycling (Telenius et al., *Genomics* 13(3):718-25, 1992) to amplify DNA. In DOP-PCR, the first rounds of PCR amplification have a low primer annealing temperature of around 30° C. The primer used consists of a random hexamer that is flanked on the 3' side by a defined hexamer and on the 5' side by a defined sequence. The target sequence must match the hexamer on the 3' side in order to amplify, which can limit the number of sequences that can be amplified by this method.

x. PEP

Another method of amplifying DNA is termed primer-extension preamplification (PEP) (Zhang et al., *Proc. Natl. Acad. Sci. USA* 89:5847-5851, 1992). PEP utilizes 15 base pair (bp) random oligonucleotides and repeated thermocycling to randomly prime multiple sites in the DNA for PCR. A method utilizing 6 base pair (bp) random oligonucleotides and PCR has also been reported (Peng et al., *Clin Pathol* 47:605-608, 1994).

xi. Tagged-Random PCR

Another method of genomic DNA amplification, termed tagged-random PCR, was described by Grothues et al. (*Nucleic Acids Res* 21:1321-1322, 1993) and Wong et al. (*Nucleic Acids Res* 24:3778-83, 1996). This method separates random priming and PCR amplification into two steps and amplifies whole genomic DNA with a single PCR primer. In the first amplification step, tagged random primers consisting of a random 6 bp to 15 bp 3' tail and a constant 17 to 22 bp 5' head indiscriminately prime the genomic DNA. Next, unincorporated tagged primers are removed by gel filtration. In the second amplification step, the DNA molecules fitted with the 5' constant head and its reverse complement at both ends are amplified by PCR.

xii. Other Amplification Methods

Other amplification methods, as described in British Patent Application No. GB 2,202,328, and in PCT Patent Application No. PCT/US89/01025, each incorporated herein by reference, may be used in accordance with the present disclosure. In the former application, "modified" primers are used in a PCR™-like template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Davey et al., European Patent Application No. 329,822 (incorporated herein by reference) disclose a nucleic acid amplification process involving cyclically synthesizing single-stranded RNA ("ssRNA"), ssDNA, and double-stranded DNA (dsDNA), which may be used in accordance with the present disclosure. The ssRNA is a first template for a first primer oligonucleotide, which is elongated by reverse transcriptase (RNA-dependent DNA polymerase). The RNA is then removed from the resulting DNA:RNA duplex by the action of ribonuclease H(RNase H, an RNase specific for RNA in duplex with either DNA or RNA). The resultant ssDNA is a second template for a second primer, which also includes the sequences of an RNA polymerase promoter (exemplified by T7 RNA polymerase) 5' of its homology to the template. This primer is then extended by DNA polymerase (exemplified by the large "Klenow" fragment of E. coli DNA polymerase I), resulting in a double-stranded DNA molecule, having a sequence identical to that of the original RNA between the primers and having additionally, at one end, a promoter sequence. This promoter sequence can be used by the appropriate RNA polymerase to make many RNA copies of the DNA. These copies can then reenter the cycle leading to very swift amplification. With proper choice of enzymes, this amplification can be done isothermally without adding enzymes at each cycle. Because of the cyclical nature of this process, the starting nucleic acid sequence can be either DNA or RNA.

Miller et al., PCT Patent Application WO 89/06700 (incorporated herein by reference), disclose a nucleic acid sequence amplification scheme based on the hybridization of a promoter/primer sequence to a target single-stranded DNA followed by transcription of many RNA copies of the sequence. This scheme is not cyclic, i.e., new templates are not produced from the resultant RNA transcripts.

Other suitable amplification methods include "race" and "one-sided PCR™" (Frohman, In: PCR Protocols: A Guide To Methods And Applications, Academic Press, N.Y., 1990). Methods based on ligation of two (or more) oligonucleotides in the presence of nucleic acid having the sequence of the resulting "di-oligonucleotide," thereby amplifying the di-oligonucleotide, also may be used to amplify DNA in accordance with the present disclosure (Wu et al., Genomics 4:560-569, 1989). Another suitable method for rapid DNA amplification for high-throughput screening is disclosed in U.S. Ser. No. 09/881,565, incorporated herein by reference.

3. Restriction Enzymes

Restriction enzymes recognize specific short DNA sequences four to eight nucleotides long, and cleave DNA at a site within this sequence. In the context of the present disclosure, restriction enzymes may be used to cleave DNA molecules at sites corresponding to various restriction-enzyme recognition sites, and for cloning nucleic acids. Additionally, restriction enzymes may be used for genotype analysis, such as identifying markers and RFLP analyses.

Since the sequence of the recognition site for a variety of restriction enzymes is well known in the art, primers can be designed that contain nucleotides corresponding to the recognition sequences. Primer sets can have in addition to the restriction recognition sequence degenerate sequences corresponding to different combinations of nucleotide sequences. A list of restriction endonuclease enzymes and their recognition sequences is available, for example, in the New England Biolabs® Inc. Catalog, available on the company's website.

4. Other Enzymes

A polymerase is an enzyme that catalyses the synthesis of nucleic acids on preexisting nucleic acid templates, assembling RNA from ribonucleotides or DNA from deoxyribonucleotides. Polymerases specifically contemplated in the context of the present disclosure may be naturally isolated, modified, or synthetic. Both thermostable and non-thermostable polymerases may be employed in the context of the present disclosure. Tables 3 and 4 set forth exemplary polymerases and nucleic acid modifying enzymes that may be used in the context of the disclosure.

TABLE 3

Polymerases

Thermostable DNA Polymerases:

OmniBase ™ Sequencing Enzyme
Pfu DNA Polymerase
Taq DNA Polymerase
Taq DNA Polymerase, Sequencing Grade
TaqBead ™ Hot Start Polymerase
AmpliTaq Gold
Vent DNA Polymerase
Tub DNA Polymerase
TaqPlus DNA Polymerase
Tfl DNA Polymerase
Tli DNA Polymerase
Tth DNA Polymerase
DNA Polymerases:

DNA Polymerase I, Klenow Fragment, Exonuclease Minus
DNA Polymerase I
DNA Polymerase I Large (Klenow) Fragment
Terminal Deoxynucleotidyl Transferase
T7 DNA Polymerase
T4 DNA Polymerase
REVERSE TRANSCRIPTASES
AMV Reverse Transcriptase
M-MLV Reverse Transcriptase

TABLE 4

DNA/RNA Modifying Enzymes

Ligases:
T4 DNA Ligase
Kinases:
T4 Polynucleotide Kinase

5. Labels

Recognition moieties incorporated into primers, incorporated into the amplified product during amplification, or attached to probes are useful in identification of the amplified molecules. A number of different labels may be used for this purpose such as, for example: fluorophores, chromophores, radio-isotopes, enzymatic tags, antibodies, chemiluminescence, electroluminescence, affinity labels, etc. One of skill in the art will recognize that these and other fluorophores not mentioned herein can also be used with success in this disclosure.

Examples of affinity labels include but are not limited to the following: an antibody, an antibody fragment, a receptor protein, a hormone, biotin, DNP, or any polypeptide/protein molecule that binds to an affinity label and may be used for separation of the amplified gene.

Examples of enzyme tags include enzymes such as urease, alkaline phosphatase, or peroxidase. Additionally, colorimetric indicator substrates can be employed to provide a detection means visible to the human eye or spectrophotometrically, to identify specific hybridization with complementary nucleic acid-containing samples. All these examples are generally known in the art and the skilled artisan will recognize that the present disclosure is not limited to the examples described above.

The following fluorophores are specifically contemplated to be useful in the present disclosure: Alexa 350, Alexa 430, AMCA, BODIPY 630/650, BODIPY 650/665, BODIPY-FL, BODIPY-R6G, BODIPY-TMR, BODIPY-TRX, Cascade Blue, Cy2, Cy3, Cy5, 6-FAM, Fluorescein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine, and Texas Red.

6. Separation and Quantitation Methods

Following the isolation of nucleic acids, amplification, or restriction enzyme digestion, it may be desirable to separate nucleic acid products of several different lengths from each other, from the template, or from excess primers for analysis.

i Gel Electrophoresis

In one embodiment, amplification products are separated by agarose, agarose-acrylamide, or polyacrylamide gel electrophoresis using standard methods (Sambrook et al., "Molecular Cloning," *A Laboratory Manual*, 2d Ed., Cold Spring Harbor Laboratory Press, New York, 13.7-13.9:1989). Gel electrophoresis techniques are well known in the art.

ii. Chromatographic Techniques

Alternatively, chromatographic techniques may be employed to effect separation. There are many kinds of chromatography which may be used in the present disclosure: adsorption, partition, ion-exchange, and molecular sieve, as well as many specialized techniques for using them including column, paper, thin-layer and gas chromatography (Freifelder, Physical Biochemistry Applications to Biochemistry and Molecular Biology, 2nd ed. Wm. Freeman and Co., New York, N.Y., 1982). Yet another alternative is to capture nucleic acid products labeled with, for example, biotin or antigen with beads bearing avidin or antibody, respectively.

iii. Microfluidic Techniques

Microfluidic techniques include separation on a platform such as microcapillaries, including by way of example those designed by ACLARA BioSciences Inc., or the LabChip™ by Caliper Technologies Inc. These microfluidic platforms require only nanoliter volumes of sample, in contrast to the microliter volumes required by other separation technologies. Miniaturizing some of the processes involved in genetic analysis has been achieved using microfluidic devices. For example, published PCT Application No. WO 94/05414, to Northrup and White, incorporated herein by reference, reports an integrated micro-PCR™ apparatus for collection and amplification of nucleic acids from a specimen. U.S. Pat. Nos. 5,304,487, 5,296,375, and 5,856,174 describe apparatus and methods incorporating the various processing and analytical operations involved in nucleic acid analysis and are incorporated herein by reference.

iv. Capillary Electrophoresis

In some embodiments, it may be desirable to provide an additional, or alternative means for analyzing the amplified DNA. In these embodiments, microcapillary arrays are contemplated to be used for the analysis. Microcapillary array electrophoresis generally involves the use of a thin capillary or channel that may or may not be filled with a particular separation medium. Electrophoresis of a sample through the capillary provides a size based separation profile for the sample. Microcapillary array electrophoresis generally provides a rapid method for size-based sequencing, PCR™ product analysis, and restriction fragment sizing. The high surface to volume ratio of these capillaries allows for the application of higher electric fields across the capillary without substantial thermal variation across the capillary, consequently allowing for more rapid separations. Furthermore, when combined with confocal imaging methods, these methods provide sensitivity in the range of attomoles, which is comparable to the sensitivity of radioactive sequencing methods. Microfabrication of microfluidic devices including microcapillary electrophoretic devices has been discussed in detail in, for example, Jacobson et al., *Anal Chem*, 66:1107-1113, 1994; Effenhauser et al., *Anal Chem*, 66:2949-2953, 1994; Harrison et al., *Science*, 261:895-897, 1993; Effenhauser et al., *Anal Chem*, 65:2637-2642, 1993; Manz et al., *J. Chromatogr* 593:253-258, 1992; and U.S. Pat. No. 5,904,824, incorporated herein by reference. Typically, these methods comprise photolithographic etching of micron scale channels on a silica, silicon, or other crystalline substrate or chip, and can be readily adapted for use in the present disclosure.

Tsuda et al. (*Anal Chem*, 62:2149-2152, 1990) describes rectangular capillaries, an alternative to the cylindrical capillary glass tubes. Some advantages of these systems are their efficient heat dissipation due to the large height-to-width ratio and, hence, their high surface-to-volume ratio and their high detection sensitivity for optical on-column detection modes. These flat separation channels have the ability to perform two-dimensional separations, with one force being applied across the separation channel, and with the sample zones detected by the use of a multi-channel array detector.

In many capillary electrophoresis methods, the capillaries, e.g., fused silica capillaries or channels etched, machined, or molded into planar substrates, are filled with an appropriate separation/sieving matrix. Typically, a variety of sieving matrices known in the art may be used in the microcapillary arrays. Examples of such matrices include, e.g., hydroxyethyl cellulose, polyacrylamide, agarose, and the like. Generally, the specific gel matrix, running buffers, and running conditions are selected to maximize the separation characteristics of the particular application, e.g., the size of the nucleic acid fragments, the required resolution, and the presence of native or undenatured nucleic acid molecules. For example, running buffers may include denaturants, chaotropic agents such as urea to denature nucleic acids in the sample.

v. Mass Spectroscopy

Mass spectrometry provides a means of "weighing" individual molecules by ionizing the molecules in vacuo and making them "fly" by volatilization. Under the influence of combinations of electric and magnetic fields, the ions follow trajectories depending on their individual mass (m) and charge (z). For low molecular weight molecules, mass spectrometry has been part of the routine physical-organic repertoire for analysis and characterization of organic molecules by the determination of the mass of the parent molecular ion. Additionally, by arranging collisions of this parent molecular ion with other particles (e.g., argon atoms), the molecular ion is fragmented forming secondary ions by the so-called collision induced dissociation (CID). The fragmentation pattern/ pathway very often allows the derivation of detailed structural information. Other applications of mass spectrometric methods in the art are summarized in Methods in Enzymology, Vol. 193: "Mass Spectrometry" (J. A. McCloskey, editor), 1990, Academic Press, New York.

Due to the apparent analytical advantages of mass spectrometry in providing high detection sensitivity, accuracy of mass measurements, detailed structural information by CID in conjunction with an MS/MS configuration and speed, as well as on-line data transfer to a computer, there has been considerable interest in the use of mass spectrometry for the structural analysis of nucleic acids. Reviews summarizing this field include (Schram, *Methods Biochem Anal*, 34:203-287, 1990) and (Crain, *Mass Spectrometry Reviews*, 9:505-554, 1990). The biggest hurdle to applying mass spectrometry to nucleic acids is the difficulty of volatilizing these very polar biopolymers. Therefore, "sequencing" had been limited to low molecular weight synthetic oligonucleotides by determining the mass of the parent molecular ion and through this, confirming the already known sequence, or alternatively, confirming the known sequence through the generation of secondary ions (fragment ions) via CID in an MS/MS configuration utilizing, in particular, for the ionization and volatilization, the method of fast atomic bombardment (FAB mass spectrometry) or plasma desorption (PD mass spectrometry). As an example, the application of FAB to the analysis of protected dimeric blocks for chemical synthesis of oligodeoxynucleotides has been described (Koster et al., *Biomedical Environmental Mass Spectrometry* 14:111-116, 1987).

Two ionization/desorption techniques are electrospray/ionspray (ES) and matrix-assisted laser desorption/ionization (MALDI). ES mass spectrometry was introduced by Fenn et al., *J. Phys. Chem.* 88;4451-59, 1984; PCT Application No. WO 90/14148 and its applications are summarized in review articles, for example, Smith et al., *Anal Chem* 62:882-89, 1990, and Ardrey, *Electrospray Mass Spectrometry, Spectroscopy Europe*, 4:10-18, 1992. As a mass analyzer, a quadrupole is most frequently used. The determination of molecular weights in femtomole amounts of sample is very accurate due to the presence of multiple ion peaks that can be used for the mass calculation.

MALDI mass spectrometry, in contrast, can be particularly attractive when a time-of-flight (TOF) configuration is used as a mass analyzer. The MALDI-TOF mass spectrometry was introduced by (Hillenkamp et al., Biological Mass Spectrometry eds. Burlingame and McCloskey, Elsevier Science Publishers, Amsterdam, pp. 49-60, 1990). Since, in most cases, no multiple molecular ion peaks are produced with this technique, the mass spectra, in principle, look simpler compared to ES mass spectrometry. DNA molecules up to a molecular weight of 410,000 Daltons could be desorbed and volatilized (Williams et al., *Science*, 246:1585-87, 1989). More recently, the use of infrared lasers (IR) in this technique (as opposed to UV-lasers) has been shown to provide mass spectra of larger nucleic acids such as synthetic DNA, restriction enzyme fragments of plasmid DNA, and RNA transcripts up to a size of 2180 nucleotides (Berkenkamp et al., *Science*, 281:260-2, 1998). Berkenkamp also describes how DNA and RNA samples can be analyzed by limited sample purification using MALDI-TOF IR.

Japanese Patent No. 59-131909 describes an instrument that detects nucleic acid fragments separated either by electrophoresis, liquid chromatography, or high speed gel filtration. Mass spectrometric detection is achieved by incorporating into the nucleic acids atoms that normally do not occur in DNA such as S, Br, I or Ag, Au, Pt, Os, Hg.

vii. Energy Transfer

Labeling hybridization oligonucleotide probes with fluorescent labels is a well known technique in the art and is a sensitive, nonradioactive method for facilitating detection of probe hybridization. More recently developed detection methods employ the process of fluorescence energy transfer (FET) rather than direct detection of fluorescence intensity for detection of probe hybridization. FET occurs between a donor fluorophore and an acceptor dye (which may or may not be a fluorophore) when the absorption spectrum of one (the acceptor) overlaps the emission spectrum of the other (the donor) and the two dyes are in close proximity. Dyes with these properties are referred to as donor/acceptor dye pairs or energy transfer dye pairs. The excited-state energy of the donor fluorophore is transferred by a resonance dipole-induced dipole interaction to the neighboring acceptor. This results in quenching of donor fluorescence. In some cases, if the acceptor is also a fluorophore, the intensity of its fluorescence may be enhanced. The efficiency of energy transfer is highly dependent on the distance between the donor and acceptor, and equations predicting these relationships have been developed by Forster, *Ann Phys* 2:55-75, 1948. The distance between donor and acceptor dyes at which energy transfer efficiency is 50% is referred to as the Forster distance ($R_o$). Other mechanisms of fluorescence quenching are also known in the art including, for example, charge transfer and collisional quenching.

Energy transfer and other mechanisms that rely on the interaction of two dyes in close proximity to produce quenching are an attractive means for detecting or identifying nucleotide sequences, as such assays may be conducted in homogeneous formats. Homogeneous assay formats differ from conventional probe hybridization assays that rely on the detection of the fluorescence of a single fluorophore label because heterogeneous assays generally require additional steps to separate hybridized label from free label. Several formats for FET hybridization assays are reviewed in Nonisotopic DNA Probe Techniques (Academic Press, Inc., pgs. 311-352, 1992).

Homogeneous methods employing energy transfer or other mechanisms of fluorescence quenching for detection of nucleic acid amplification have also been described. Higuchi et al. (*Biotechnology* 10:413-417, 1992), discloses methods for detecting DNA amplification in real-time by monitoring increased fluorescence of ethidium bromide as it binds to double-stranded DNA. The sensitivity of this method is limited because binding of the ethidium bromide is not target specific and background amplification products are also detected. Lee et al. (*Nucleic Acids Res* 21:3761-3766, 1993), discloses a real-time detection method in which a doubly-labeled detector probe is cleaved in a target amplification-specific manner during PCR™. The detector probe is hybridized downstream of the amplification primer so that the 5'-3' exonuclease activity of Taq polymerase digests the detector probe, separating two fluorescent dyes, which then form an energy transfer pair. Fluorescence intensity increases as the probe is cleaved. Published PCT application WO 96/21144 discloses continuous fluorometric assays in which enzyme-mediated cleavage of nucleic acids results in increased fluorescence. Fluorescence energy transfer is suggested for use, but only in the context of a method employing a single fluorescent label that is quenched by hybridization to the target.

Signal primers or detector probes that hybridize to the target sequence downstream of the hybridization site of the amplification primers have been described for use in detection of nucleic acid amplification (U.S. Pat. No. 5,547,861, incorporated herein by reference). The signal primer is extended by the polymerase in a manner similar to extension of the amplification primers. Extension of the amplification primer displaces the extension product of the signal primer in a target amplification-dependent manner, producing a double-stranded secondary amplification product that may be detected as an indication of target amplification. The secondary amplification products generated from signal primers may be detected by means of a variety of labels and reporter groups, restriction sites in the signal primer that are cleaved to produce fragments of a characteristic size, capture groups, and structural features such as triple helices and recognition sites for double-stranded DNA binding proteins.

Many donor/acceptor dye pairs are known in the art and may be used in the present disclosure. These include but are not limited to: fluorescein isothiocyanate (FITC)/tetramethylrhodamine isothiocyanate (TALIC), FITC/Texas Red™ Molecular Probes, FITC/N-hydroxysuccmimidyl 1-pyrenebutyrate (PYB), FITC/eosin isothiocyanate (EITC), N-hydroxysuccinimidyl 1-pyrenesulfonate (PYS)/FITC, FITC/Rhodamine X, FITC/tetramethylrhodamine (TAMRA), and others. The selection of a particular donor/acceptor fluorophore pair is not critical. For energy transfer quenching mechanisms it is only necessary that the emission wavelengths of the donor fluorophore overlap the excitation wavelengths of the acceptor, i.e., there must be sufficient spectral overlap between the two dyes to allow efficient energy transfer, charge transfer, or fluorescence quenching. P-(dimethyl aminophenylazo) benzoic acid (DABCYL) is a non-fluorescent acceptor dye which effectively quenches fluorescence from an adjacent fluorophore, e.g., fluorescein or 5-(2'-aminoethyl) aminonaphthalene (EDANS). Any dye pairs that produce fluorescence quenching in the detector nucleic acids are suitable for use in the methods of the disclosure, regardless of the mechanism by which quenching occurs. Terminal and internal labeling methods are both known in the art and may be routinely used to link the donor and acceptor dyes at their respective sites in the detector nucleic acid.

viii. Microarrays and Chip Technologies

Specifically contemplated in the present disclosure is the use or analysis of amplified products by microarrays and/or chip-based DNA technologies such as those described by (Hacia et al., *Nature Genet*, 14:441-449, 1996) and (Shoemaker et al., *Nature Genetics*, 14:450-456, 1996). These techniques involve quantitative methods for analyzing large numbers of genes rapidly and accurately. By tagging genes with oligonucleotides or using fixed probe arrays, chip technology can be employed to segregate target molecules as high density arrays and screen these molecules on the basis of hybridization (Pease et al., *Proc Natl Acad Sci USA*, 91:5022-5026, 1994; Fodor et al, *Nature*, 364:555-556, 1993).

ix. OIA.

Also contemplated is the use of BioStar's OIA technology to quantitate amplified products. OIA uses the mirror-like surface of a silicon wafer as a substrate. A thin film optical coating and capture antibody is attached to the silicon wafer. White light reflected through the coating appears as a golden background color. This color does not change until the thickness of the optical molecular thin film is changed. When a positive sample is applied to the wafer, binding occurs between the ligand and the antibody. When substrate is added to complete the mass enhancement, a corresponding change in color from gold to purple/blue results from the increased thickness in the molecular thin film. The technique is described in U.S. Pat. No. 5,541,057, incorporated herein by reference.

x. Real Time PCR

Amplified RNA or DNA may be quantitated using the Real-Time PCR technique (Higuchi et al., *Biotechnology* 10:413-417, 1992). By determining the concentration of the amplified products that have completed the same number of cycles and are in their linear ranges, it is possible to determine the relative concentrations of the specific target sequence in the original DNA mixture. For example, if the DNA mixtures are cDNAs synthesized from RNAs isolated from different tissues or cells, the relative abundance of the specific mRNA from which the target sequence was derived can be determined for the respective tissues or cells. This direct proportionality between the concentration of the amplification products and the relative mRNA abundance is only true in the linear range of the amplification reaction.

The final concentration of the target DNA in the plateau portion of the curve is determined by the availability of reagents in the reaction mixture and is independent of the original concentration of target DNA. Therefore, the first condition that must be met before the relative abundance of a RNA or DNA species can be determined by Real-Time PCR for a collection of RNA or DNA populations is that the concentrations of the amplified products must be sampled when the reaction products are in the linear portion of their curves. The second condition that must be met for an RT-PCR experiment to successfully determine the relative abundance of a particular mRNA species is that relative concentrations of the amplifiable cDNAs must be normalized to some independent standard. The goal of a Real-Time PCR experiment is to determine the abundance of a particular RNA or DNA species relative to the average abundance of all RNA or DNA species in the sample.

xi. Luminex

The Luminex technology allows the quantitation of nucleic acid products immobilized on color coded microspheres. The magnitude of the biomolecular reaction is measured using a second molecule called a reporter. The reporter molecule signals the extent of the reaction by attaching to the molecules on the microspheres. As both the microspheres and the reporter molecules are color coded, digital signal processing allows the translation of signals into real-time, quantitative data for each reaction. The standard technique is described in U.S. Pat. Nos. 5,736,303 and 6,057,107, incorporated herein by reference.

8. Identification Methods

Amplification products must be visualized in order to confirm amplification of the target-gene(s) sequences. One typical visualization method involves staining of a gel with a fluorescent dye, such as ethidium bromide or Vistra Green, and visualization under UV light. Alternatively, if the amplification products are integrally labeled with radio- or fluorometrically-labeled nucleotides, the amplification products can be exposed to x-ray film or visualized under the appropriate stimulating spectra following separation.

In one embodiment, visualization is achieved indirectly, using a nucleic acid probe. Following separation of amplification products, a labeled, nucleic acid probe is brought into contact with the amplified products. The probe preferably is conjugated to a chromophore but may be radiolabeled. In another embodiment, the probe is conjugated to a binding partner, such as an antibody or biotin, where the other member of the binding pair carries a detectable moiety. In other embodiments, the probe incorporates a fluorescent dye or label. In yet other embodiments, the probe has a mass label that can be used to detect the molecule amplified. Other embodiments also contemplate the use of Taqman™ and Molecular Beacon™ probes. In still other embodiments, solid-phase capture methods combined with a standard probe may be used.

The type of label incorporated in DNA amplification products is dictated by the method used for analysis. When using capillary electrophoresis, microfluidic electrophoresis, HPLC, or LC separations, either incorporated or intercalated fluorescent dyes are used to label and detect the amplification products. Samples are detected dynamically, in that fluorescence is quantitated as a labeled species moves past the detector. If any electrophoretic method, HPLC, or LC is used for separation, products can be detected by absorption of UV light, a property inherent to DNA and therefore not requiring addition of a label. If polyacrylamide gel or slab gel electrophoresis is used, primers for the amplification reactions can be labeled with a fluorophore, a chromophore, or a radioisotope, or by associated enzymatic reaction. Enzymatic detection involves binding an enzyme to a primer, e.g., via a biotin: avidin interaction, following separation of the amplification products on a gel, then detection by chemical reaction, such as chemiluminescence generated with luminol. A fluorescent signal can be monitored dynamically. Detection with a radioisotope or enzymatic reaction requires an initial separation by gel electrophoresis, followed by transfer of DNA molecules to a solid support (blot) prior to analysis. If blots are made, they can be analyzed more than once by probing, stripping the blot, and then reprobing. If amplification products are separated using a mass spectrometer no label is required because nucleic acids are detected directly.

A number of the above separation platforms can be coupled to achieve separations based on two different properties. For example, some of the PCR™ primers can be coupled with a moiety that allows affinity capture, while some primers remain unmodified. Modifications can include a sugar (for binding to a lectin column), a hydrophobic group (for binding to a reverse-phase column), biotin (for binding to a streptavidin column), or an antigen (for binding to an antibody column). Samples are run through an affinity chromatography column. The flow-through fraction is collected, and the bound fraction eluted (by chemical cleavage, salt elution, etc.). Each sample is then further fractionated based on a property, such as mass, to identify individual components.

10. Kits

The materials and reagents required for genotyping the presently disclosed genetic markers and/or SNPs linked to or in the SST locus in animals, preferably bovine, may be assembled together in a kit. The kits of the present disclosure generally will include at least the enzymes and primers necessary to identify the disclosed markers and/or SNPs. In a preferred embodiment, the kit will also contain directions for gathering nucleic acid samples and diagnostic evaluation of those samples.

The kits of the present disclosure also will generally include one or more preselected primer sets and/or probes that will be specific for the genetic markers, SNPs, and/or haplotypes to be identified. Preferably, the kits will include, in a suitable container means, one or more nucleic acid probes and/or primer sets and means for detecting nucleic acids. In certain embodiments, such as in kits for use in amplification reactions, the means for detecting the nucleic acids may be a label, such as a fluorophore, a radiolabel, an enzyme tag, etc., that is operably attached or linked to the nucleic acid primer or the nucleotides themselves. It is envisioned that kits may contain pairs of primer sets for each genetic marker and/or SNP of the present disclosure.

In each case, the kits will preferably have distinct containers for each individual reagent and enzyme, as well as for each probe or primer pair. Each biological agent will generally be suitably aliquoted in their respective containers. The container means of the kits will generally include at least one vial or test tube. Flasks, bottles, and other container means into which the reagents are placed and aliquoted are also possible. The individual containers of the kit will preferably be maintained in close confinement for commercial sale. Suitable larger containers may include injection or blow-molded plastic containers into which the desired vials are retained. Instructions are preferably provided with the kit.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

A more precise chromosomal location for the SST locus was mapped using a genomic SST clone that was isolated by screening a bovine Bacterial Artificial Chromosome (BAC) library. The BAC library was screened and a genomic SST clone was isolated by using a 297 bp fragment that included exon 2 of the SST gene. Two primers, 5'-ACTTCTTGGCA-GAGCTGCTGTC-3' (SEQ ID NO:4) and 5'-AC-GAGGGTCTTATTGAGGATTGG-3' (SEQ ID NO:5), were used to amplify the SST fragment by PCR, using an annealing temperature 57° C. for 1 min (see Cai et al., *Genomics* 29:413-425 1995). The primers were designed based on the published nuclear DNA sequence of the SST gene (Accession No. U97077). Clone 36H7 was isolated from the BAC library, and DNA sequencing with an ABI 377 automated sequencer confirmed that the clone contained the 297 bp SST DNA fragment.

FISH analysis with the 36H7 clone demonstrated a strong, consistent signal on bovine chromosome 1 at region 1q32, thus localizing the SST gene to this region. The chromosomal FISH analysis with the 36H7 clone followed the standard protocol as outlined in Pinkel et al. (*Proc Natl Acad Sci USA* 83:2934-2938, 1986, incorporated herein by reference), with only slight modifications as described in Yeh et al. (*Genomics* 32:245-252, 1996, incorporated herein by reference). The 36H7 probe hybridization signal was assigned to chromosome band location 1q32 by examining a minimum of ten mitotic cells and plotting the probe signal relative to the standard ideogram. This assignment of SST to 1q32 is different from the published assignment of SST to 1q23-24 by Thue and Schmutz. (*Mamm Genome* 6:688-9, 1995). As used herein, bovine chromosomes are identified according to the standard nomenclature of those skilled in the art (ISCNDA 1990 International system for cytogenetic nomenclature of domestic animals, *Cytogenet Cell Genet* 53:65-79, 1989; Popescu et al., *Cytogenetics and Cell Genetics* 74:259-261, 1996).

A novel polymorphic microsatellite (SSTms) from the 36H7 BAC clone maps to the QTL region of chromosome 1 at region 1q32 in the *Bos indicus* (Brahman) x *Bos taurus* (Angus) mapping population. Methods to acquire novel microsatellites from BAC clones are well known to those of skill in the art. A standard protocol was followed to identify SSTms (see Cai et al., *Genomics* 29:413-25, 1995; Marquess et al., *Anim Genet* 28:70, 1997; and Taylor et al., *Anim Genet* 29:194-201, 1998, incorporated herein by reference), which is a di-nucleotide repeat $(GT)_9$ microsatellite. A set of primers, 5'-CTTATTCATATCTTGCCAGTT-3' (SEQ ID NO:6) and 5'-GGGAGCTTTGTGGTGA-3' (SEQ ID NO:7), were designed to amplify a 152 bp product that contains the SSTms. SSTms has 3 alleles, and generated 732 informative meioses (438 phase known), when scored in the resource families.

EXAMPLE 2

After the chromosomal location of the SST locus was mapped, a set of primers were designed to amplify and clone the genomic locus of the SST gene, including the bovine sequence for preprosomatostatin. The primers were designed to amplify different regions of the 2927 bp segment encompassing the 5' untranslated region (5'UTR), two exons, and the intron sequence of the SST locus (SEQ ID NO:1). The primer sets used to amplify different portions of the 2927 bp segment were:

Primer set 1: 5'-GCCTGGCTGGAGACAGGGTTAGT-CATG-3' (SEQ ID NO:8), nucleotides −1457 to −1431 of SEQ ID NO:1; and 5'-CAGAAACCATCTAC-TAAACCCCA-3' (SEQ ID NO:9), the reverse complement of nucleotides −910 to −888 of SEQ ID NO:1.

Primer set 2: 5'-TAGGAGAGGCAAGGTTC-3' (SEQ ID NO:10), nucleotides −96 to −80 of SEQ ID NO:1; and 5'-CCAATAGATTAGCTCAATGTCCA-3' (SEQ ID NO:11), the reverse complement of nucleotides 647 to 669 of SEQ ID NO:1.

Primer set 3: 5'-GATCCCCGGCTCCGTCAGTTTCT-3' (SEQ ID NO:12), nucleotides 82 to 104 of SEQ ID NO:1; and 5'-CCTGGGACAAATCTTCAGGCTC-3' (SEQ ID NO:13), the reverse complement of nucleotides 1047 to 1068 of SEQ ID NO:1.

Primer set 4: 5'-TGGACATTGAGCTAATCTATTGG-3' (SEQ ID NO:14), nucleotides 647 to 669 of SEQ ID NO:1; and 5'-GGAGGGATTAGGGAGGTGAG-3' (SEQ ID NO:15), the reverse complement of nucleotides 1251 to 1270 of SEQ ID NO:1.

DNA was amplified by each of the above primer sets using genomic DNA from both Angus and Brahman animals and sequenced to identify polymorphisms within the SST locus. Genomic DNA sequences were analyzed and compared from all progeny in the Angleton Family Pedigree. The analyzed genomic DNA sequence, which includes the more common polymorphisms for each SNP identified in the SST locus (in bold and underlined), is shown in FIGS. 14A-B (also shown in SEQ ID NO:27), and shown in SEQ ID NO:1 (SST gene).

The 2927 bp amplified DNA product includes the two exons (exon 1 is 138 bp and exon 2 is 213 bp), and the intron (842 bp in length) of the SST locus. The intron separates the coding region of the SST gene between the codons that encode for glutamine (Gln) at amino acid 46 and glutamic acid (Glu) at amino acid 47 of the SST protein. The exons of the SST gene code for a preprohormone that is processed into somatostatin-28 and somatostatin-14. Somatostatin-28 is the precursor of somatostatin-14, and has greater biological activity on a molar basis for inhibition of growth hormone (Sonntag, An overview of the biological actions and neuroendocrine regulation of growth hormone, pp. 171-202 in Handbook of Endocrinology 2nd ed., edited by G. H. Gass and H. M. Kaplan, CRC Press, Boca Raton, Fla., 1996). A variant of the TATA box, TTTAAA, is found between nucleotides −136 and −129 of the 2927 bp SST gene fragment and GGCTAAT, a variant of the CAAT box, is found between nucleotides −203 and −197. The consensus sequence AATAAA is found 17 bp upstream of the poly (A) addition site at the 3' end of the gene. As used herein, all nucleotide locations in the SST locus are based on the start site of translation of the SST gene being designated +1.

The regulatory region of the SST gene contains a short palindromic DNA region, 5'-TGACGTCA-3', located at nucleotide −153, called a cAMP response element (CRE). There is a second CRE site at position 154, within the intron of the SST gene. The CRE sequence is recognized by a regulatory protein called CRE-binding protein (CREB). When CREB is phosphorylated by A-kinase on a single serine residue, it will activate transcription of the SST gene (Alberts et al., Molecular biology of the cell, 3rd Edition Garland Publishing, Inc., New York, 1994). Additionally, the "GT-AG" rule of the intron junction, in which the di-nucleotides GT and AG are invariably present at splice donor and acceptor sites, is followed in the bovine SST genomic DNA sequence (Breathnach and Chambron, *Ann Rev Biochem* 50:349-83, 1981). The splice acceptor sites in the SST gene are also consistent with a study that found that in vertebrate introns, the splice acceptor site (AG) was followed by a G or an A in 49% and 26% of the cases, respectively (Hawkins J. D., *Gene structure and expression,* 3rd ed. Cambridge University Press, Cambridge, 1996).

Alignment of SST genomic DNA sequences from human (Accession No. J00306), rat (Accession No. J00787), and bovine demonstrates that the CRE regulatory regions in the 5' untranslated region of these sequences are completely conserved (see FIG. 12). There are also important differences between the sequences. For example, the human TATA box contains a C that is not present in the rat and bovine sequences, and only the bovine sequence has a second CRE site within the first SST intron. Additionally, the amino acid sequence encoded by exon 1 of the bovine SST gene differs from the published rat protein sequence by two amino acids, a Ser-Cys at amino acid 14 and Ala-Thr at amino acid 43, respectively. The amino acid sequence of the bovine SST gene also differs from the human protein sequence by one amino acid, Gly-Cys at amino acid 21, respectively. In exon 2, the published bovine sequence (Accession No. U97077) differs from both the rat and human sequences at one amino acid (Ile-Asn at amino acid 65, respectively) and the human and bovine sequence differs from the rat sequence at a single amino acid (Ser-Pro at amino acid 74, respectively). This high degree of sequence conservation suggests that the biological function of the SST gene is highly conserved in these three species, which also suggests that QTLs associated with the SST locus in one species will be associated with the SST locus in other species of interest.

Analysis of 44 DNA sequences amplified from the Angus and Brahman grandparent and parent animals in the Angleton Family Pedigree also revealed five interesting single nucleotide polymorphisms (SNPs) (see FIG. 13). Subsequent linkage disequilibrium analysis using these SNPs demonstrated that the SNPs are linked to a variety of traits in bovine, including the commercially valuable trait marbling. The numbering assigned to each SNP is based on the start site of translation of the SST gene being designated +1. The five SNPs of interest were identified in at least one allele, and are as follows:

1. At position 126, seventeen Brahman had a C-T transitional change in the first exon of the SST gene. The animals were both homozygous and heterozygous for this change.
2. At position 157, a C-T transitional change was identified in the second CRE site located in the first intron of the SST gene in the bovine sequence. Five Brahman and one Angus were heterozygous for this polymorphism.
3. At position 244, twenty Brahman had a T-C transitional base change. The animals were both homozygous and heterozygous for this change.

4. At position 575, twenty Brahman had a C-T transitional base change. The animals were both homozygous and heterozygous for this change.

5. At position 981, two Angus were found to be heterozygous for a G-A transitional base change. This polymorphism alters the first codon of exon 2, which results in an amino acid change from glutamic acid (GAA) to lysine (AAA) in the protein encoded by the SST gene.

An examination of the data in FIG. 13 demonstrates that the three SNPs found in the non-coding intronic region of the SST gene at position 157, 244, and 575 are each associated with more than one allele in the coding region of the SST gene at positions 126 and 981. For example, the genotype CC at position 244 is associated with both the TT and CC alleles at position 126.

SNPs of interest found in the SST locus in bovine animals can be identified using novel primer sequences encompassing an individual SNP. In a preferred embodiment of the present disclosure, nucleic acid molecule probe sequences can be designed based on the genomic DNA sequence of the SST gene. Examples of probes that may be designed by one of skill in the art using SEQ ID NO:1, which is the genomic sequence of the SST gene, are shown in Table 5 for the five identified SNPs of interest:

TABLE 5

| SNP position | sequence | |
|---|---|---|
| 126 | CCTGGCTGCTGCCGCTGGCAAG | SEQ ID NO:16 |
| 126 | CCTGGCTGCTGCTGCTGGCAAG | SEQ ID NO:17 |
| 157 | CTCCCTTGACGTCTTCTTTCCC | SEQ ID NO:18 |
| 157 | CTCCCTTGATGTCTTCTTTCCC | SEQ ID NO:19 |
| 244 | CCCACAGTGCTGGTGCCTTTC | SEQ ID NO:20 |
| 244 | CCCACAGTGCCGGTGCCTTTC | SEQ ID NO:21 |
| 575 | GTTTACGGTTGCGAAAGGTCTC | SEQ ID NO:22 |
| 575 | GTTTACGGTTGTGAAAGGTCTC | SEQ ID NO:23 |
| 981 | CCCCATGCAGGAACTGGCCAAG | SEQ ID NO:24 |
| 981 | CCCCATGCAGAAACTGGCCAAG | SEQ ID NO:25 |

In the above list of sequences, the more frequent or "wild-type" SNP is indicated in bold, while the less frequent or alternate SNP is indicated in bold and underlined. As is well understood in the art of nucleic acid hybridization, the above sequence primers, their complements, as well as variations of these sequences in terms of their respective lengths, may be used to analyze and genotype the DNA of bovine animals. The nucleic acid sequence probes and their complements may be extended both 5" and 3' in terms of their length according to the more complete DNA sequence of the SST locus in SEQ ID NO:1. For example, an 18 bp nucleic acid molecule with the alternate SNP corresponding to nucleotide 244 of SEQ ID NO:1 located at its 3' end, having the sequence 5'-AGGTGCTCCCACAGTGCC-3' (SEQ ID NO:26), may be generated by those of skill in the art using the sequence information in SEQ ID NO:1 or SEQ ID NO:27. Hybridization techniques and methods for detection of hybridization events are well known to those of skill in the art. Methods to detect SNPs in the DNA of an animal are also well known to those of skill in the art.

Using the bovine sequences listed in Table 5 and the full SST sequence found in SEQ ID NO:27 (or a portion of this sequence as shown in SEQ ID NO:1), nucleic acid probes may be generated to detect each of the SNPs listed in Table 5. In a preferred embodiment, a first nucleic acid molecule having a length sufficient under appropriate hybridization conditions to hybridize to a target bovine nucleic acid sequence is designed to have either a 5' or a 3' base that anneals to the nucleotide adjacent to the SNP nucleotide, either 3' or 5' to the SNP, respectively. A second nucleic acid molecule is designed to have a label and either a 5' or a 3' nucleotide that is, or is complementary to, the SNP nucleotide to be detected. Hybridization of the first and second probes to the target bovine sequence will occur under selective stringency hybridization conditions such that the first and second probe will only hybridize if they perfectly match the target sequence and the SNP. Thus, if a first probe containing a 3' base annealing adjacent to the SNP and a second probe having a nucleotide that is the complement of the SNP nucleotide to be detected at its 5' end are hybridized to a target sequence, then the presence of the specific SNP will be detected. A number of other methods are also available and well known to those of skill in the art for identifying SNPs, and nucleic acid probes can be designed according to the particular protocol utilized.

EXAMPLE 3

A series of statistical analyses were performed on the polymorphisms identified in the progeny of the Angleton Family Pedigree to determine the SST locations that are associated with desired traits in bovine. The data structure for each of the single loci in the complete data set are shown below:

| Genotype | SSTms | C126T | C157T | T244C | C575T | G981A |
|---|---|---|---|---|---|---|
| 11 | 136 | 271 | 550 | 99 | 231 | 6 |
| 12 | 333 | 295 | 58 | 325 | 313 | 52 |
| 22 | 145 | 48 | 6 | 190 | 70 | 556 |
| Total | 614 | 614 | 614 | 614 | 614 | 614 |

The Genotype designation of 11, 12, and 22 reflects the particular alleles of the SST locus present at the microsatellite or SNP location in an animal. For each of the above Genotype designations, the SNPs were designated as follows: genotype 11 is CC and genotype 22 is TT for C126T; genotype 11 is CC and genotype 22 is TT for C157T; genotype 11 is CC and genotype 22 is TT for T244C; genotype 11 is CC and genotype 22 is TT for C575T; and genotype 11 is AA and genotype 22 is GG for G981A. Animals with genotypes 11 and 22 are homozygous, and animals with genotype 12 are heterozygous at a particular SNP location. For example, with SNP C575T, 231 animals had a C nucleotide at position 575 in both of their SST genes (genotype 11), and 313 animals had a T or a C nucleotide at position 575 in one copy each of their SST genes (heterozygous genotype 12).

The statistical analyses subsequently performed took into account as much "background noise" as possible. The following models for slaughter traits; birth weight (BWT), gestation length (GEST), and ear length at birth (EAR); weaning weight (WWT); and yearling weight (YRWT), were applied in the analyses:

| | |
|---|---|
| Slaughter traits = | $BYS^a + FAMILY^b + b1^{c*}DOF^d + b2^{c*}OOAGE^e$ |
| BWT, GEST, EAR = | $BYS^a + FAMILY^b + RECIP^f + BDBYS^g$ |
| WWT = | $BYS^a + FAMILY^b + RECIP^f + WAGE^h$ |
| YRWT = | $BYS^a + FAMILY^b + b1^{c*}OOAGE^e$ |

[a] birth year season
[b] family number
[c] regression coefficient
[d] days on feed
[e] age into feedlot
[f] recipient cow
[g] birthday within season (d)
[h] age at weaning To begin, the SSTms marker and four of the five SNPs were analyzed individually to determine whether one single polymorphism accounts for the observed trait variations. The effects of the five identified polymorphisms (SNPs and SSTms) in the SST locus on the traits linked to the same chromosomal region were evaluated statistically by testing if the genotypes at a single SST location explain a significant part of the variance of the trait under investigation. Models incorporated the fixed effects as previously described.

The statistically significant results (p-value<0.05) of the genotypic effect of the individual SNPs in the bovine SST gene and the SSTms marker on the following traits are shown below: ear (EAR); yearling weight (YRWT); average daily weight gain on feed (ADGF); final weight (FWT); hot carcass weight (HCW); rib eye area (REA); kidney, pelvic and heart fat percentage (KPH); actual fat thickness over the 10th and 11th rib (ACFT); adjusted fat thickness based on the size of the animal (ADFT); intramuscular fat or marbling (MARB); quality grade (QG); fat percentage in muscle (FATP); flavor (FLV); and juiciness (JC).

|  | SSTms | C126T | T244C | C575T | G981A |
|---|---|---|---|---|---|
| EAR | | | | | |
| No. of observations | | 600 | | 600 | |
| p-value | | 0.0047 | | 0.0265 | |
| 11 | | −0.40 ± 0.15 | | −0.328 ± 0.145 | |
| 12 | | 0 | | 0 | |
| 22 | | −0.61 ± 0.27 | | −0.41 ± 0.22 | |
| YRWT | | | | | |
| No. of observations | 559 | 559 | 559 | | 559 |
| p-value | 0.0009 | 0.00726 | 0.0065 | | 0.0021 |
| 11 | −14.32 ± 3.9 | −10.79 ± 3.53 | −3.54 ± 4.58 | | −11.72 ± 3.41 |
| 12 | 0 | 0 | 0 | | 0 |
| 22 | −4.30 ± 4.01 | −7.36 ± 6.58 | −11.54 ± 3.64 | | −7.47 ± 5.33 |
| ADGF | | | | | |
| No. of observations | 540 | 540 | | | |
| p-value | 0.0138 | 0.011 | | | |
| 11 | 0.037 ± 0.025 | 0.067 ± 0.023 | | | |
| 12 | 0 | 0 | | | |
| 22 | −0.064 ± 0.026 | 0.029 ± 0.042 | | | |
| FWT | | | | | |
| No. of observations | 528 | | | | |
| p-value | 0.0276 | | | | |
| 11 | −6.47 ± 5.76 | | | | |
| 12 | 0 | | | | |
| 22 | −14.39 ± 5.77 | | | | |
| HCT | | | | | |
| No. of observations | 539 | | | | |
| p-value | 0.0169 | | | | |
| 11 | −5.53 ± 3.94 | | | | |
| 12 | 0 | | | | |
| 22 | −10.37 ± 4.04 | | | | |
| REA | | | | | |
| No. of observations | 539 | | | | |
| p-value | 0.018 | | | | |
| 11 | −1.19 ± 0.95 | | | | |
| 12 | 0 | | | | |
| 22 | −2.54 ± 0.97 | | | | |
| KPH | | | | | |
| No. of observations | | | | | 539 |
| p-value | | | | | 0.019 |
| 11 | | | | | −0.094 ± 0.29 |
| 12 | | | | | 0 |
| 22 | | | | | 0.328 ± 0.12 |
| ACFT | | | | | |
| No. of observations | 539 | | 539 | | |
| p-value | 0.0136 | | 0.0019 | | |
| 11 | 0.435 ± 0.518 | | −2.092 ± 0.604 | | |

-continued

|  | SSTms | C126T | T244C | C575T | G981A |
|---|---|---|---|---|---|
| 12 | 0 | | 0 | | |
| 22 | −1.477 ± 0.53 | | 0.189 ± 0.479 | | |
| ADFT | | | | | |
| No. of observations | | | 534 | | |
| p-value | | | 0.046 | | |
| 11 | | | −1.52 ± 0.62 | | |
| 12 | | | 0 | | |
| 22 | | | 0.0059 ± 0.49 | | |
| MARB | | | | | |
| No. of observations | 539 | 539 | 539 | 539 | |
| p-value | 0.00085 | 0.00155 | 0.00051 | 0.00005 | |
| 11 | 24.06 ± 8.31 | 23.34 ± 7.497 | −18.13 ± 9.71 | 25.96 ± 7.19 | |
| 12 | 0 | 0 | 0 | 0 | |
| 22 | −19.66 ± 8.52 | −20.51 ± 13.85 | 24.61 ± 7.7 | −22.46 ± 11.33 | |
| QG | | | | | |
| No. of observations | 539 | 539 | 539 | 539 | |
| p-value | 0.000106 | 0.000301 | 4.6e−005 | 5e−006 | |
| 11 | 10.045 ± 4.53 | 12.16 ± 4.09 | −16.55 ± 5.29 | 13.23 ± 3.91 | |
| 12 | 0 | 0 | 0 | 0 | |
| 22 | −16.71 ± 4.64 | −18.18 ± 7.55 | 11.94 ± 4.19 | −18.79 ± 6.17 | |
| FATP | | | | | |
| No. of observations | | 275 | 275 | 275 | |
| p-value | | 0.031 | 0.042 | 0.024 | |
| 11 | | 0.436 ± 0.20 | −0.43 ± 0.25 | 0.40 ± 0.19 | |
| 12 | | 0 | 0 | 0 | |
| 22 | | −0.51 ± 0.38 | 0.36 ± 0.22 | −0.44 ± 0.31 | |
| FLV | | | | | |
| No. of observations | | | 533 | | |
| p-value | | | 0.038 | | |
| 11 | | | −0.14 ± 0.055 | | |
| 12 | | | 0 | | |
| 22 | | | −0.021 ± 0.044 | | |
| JC | | | | | |
| No. of observations | 533 | | 533 | | |
| p-value | 0.0035 | | 0.0183 | | |
| 11 | −0.114 ± 0.076 | | −0.22 ± 0.089 | | |
| 12 | 0 | | 0 | | |
| 22 | −0.24 ± 0.078 | | −0.117 ± 0.071 | | |

The above results indicate that the SST microsatellite and the T244C SNP are clearly associated with QTLs for the majority of the traits of interest. Statistically significant results were also obtained for 3 of the 4 SNPs analyzed for the marbling trait and the quality grade trait.

Next, haplotype analyses were performed to investigate if a certain haplotype is associated with the traits of interest. The analyses outlined below focus on the marbling trait (N=523). Haplotype construction revealed five haplotypes (denoted by H), which are present in the Angleton Family Pedigree: H11211, H11212, H11122, H12112, H21122. The nucleotide at each location in the 5-SNP-haplotype is indicated by the number 1 or 2, according to the Genotype designations for each SNP in the SST locus disclosed above. For example, an animal with the haplotype H11211 has nucleotide C at position 126, nucleotide C at position 157, nucleotide T at position 244, nucleotide C at position 575, and nucleotide A at position 981 in the SST locus.

A partial regression model on the number of observed haplotypes revealed that haplotype H11212 is associated with a significant effect ($p \leq 0.0002$) on marbling:

| Marbling | Df | Sum of Sq | Mean Sq | F Value | Pr(F) |
|---|---|---|---|---|---|
| BYS | 10 | 120720.8 | 12072.08 | 2.56 | 0.0051 |
| FAMILY | 34 | 1963028.16 | 57736.12 | 12.24 | 0 |
| DOF | 1 | 11216.21 | 11216.21 | 2.38 | 0.124 |
| OOAGE | 1 | 32644.425 | 32644.425 | 6.92 | 0.0088 |
| H11211 | 1 | 8630.995 | 8630.995 | 1.83 | 0.177 |
| H11212 | 1 | 67256.15 | 67256.15 | 14.26 | 0.00018 |
| H11122 | 1 | 5065.53 | 5065.53 | 1.074 | 0.3 |
| H12112 | 1 | 13230.49 | 13230.49 | 2.805 | 0.095 |
| Residuals | 472 | 2226252.5 | 4716.64 | | |

Next, a two-locus genotype was analyzed using two SNPs, T244C and C575T (T244C.C575T), representing all haplotypes present in the Angleton families. The chart below shows the genotypes that were analyzed; for example, in the T244C.C575T genotype 2211, 22 represents the genotype at T244C (TT), and 11 represents the genotype at C575T (CC). The relationship between the T244C.C575T genotypes and haplotypes are shown below:

| T244C.C575T Genotype | Haplotype |
|---|---|
| 2211 | 2 1 / 2 1 |
| 1122 | 1 2 / 1 2 |
| 1212 | 2 1 / 1 2 |
| 1211 | 2 1 / 1 1 |
| 1112 | 1 2 / 1 1 |
| 1111 | 1 1 / 1 1 |

In the following model, only T244C.C575T haplotypes (G: (G21=H11211, H11212)+(G12=H11122, H21122)+(G11=HB12112); T244C.C575T alleles in bold) were included.

| Marbling | Df | Sum of Sq | Mean Sq | F Value | Pr(F) |
|---|---|---|---|---|---|
| BYS | 10 | 120720.83 | 12072.08 | 2.57 | 0.0049 |
| FAMILY | 34 | 1963028.16 | 57736.126 | 12.29 | 0.00 |
| DOF | 1 | 11216.21 | 11216.21 | 2.39 | 0.123 |
| OOAGE | 1 | 32644.42 | 32644.42 | 6.95 | 0.00867 |
| G21 | 1 | 75027.05 | 75027.045 | 15.97 | 0.000075 |
| G12 | 1 | 18290.60 | 18290.60 | 3.89 | 0.049 |
| Residuals | 474 | 2227118.04 | 4698.56 | | |

Compared to the previous model that includes haplotypes of all 5 SNPs, the results are not significantly different. Thus, although the SNPs C126T, C157T, and G981A may be used to further define a haplotype associated with a trait of interest, such as the marbling trait, it is unlikely that these SNPs provide additional predictive power for the trait. The estimated effects of the two-locus haplotypes on the marbling score were:

| G21 | G12 | G11 |
|---|---|---|
| 1.13 | −24.8 | 0 |

The partial regression model on the six two-locus genotypes for T244C.C575T (X) explained significantly more variation in marbling than the model including the 5 SNPs haplotypes or the T244.C575T haplotypes.

| | Df | Sum of Sq | Mean Sq | F Value | Pr(F) |
|---|---|---|---|---|---|
| BYS | 10 | 116313.04 | 11631.30 | 2.61 | 0.0043 |
| FAMILY | 34 | 1999077.0 | 58796.38 | 13.19 | 0.00 |

-continued

| | Df | Sum of Sq | Mean Sq | F Value | Pr(F) |
|---|---|---|---|---|---|
| DOF | 1 | 4785.84 | 4785.84 | 1.07 | 0.30 |
| OOAGE | 1 | 35169.99 | 35169.99 | 7.89 | 0.0052 |
| X2211 | 1 | 54440.21 | 54440.21 | 12.21 | 0.00052 |
| X1122 | 1 | 20193.46 | 20193.46 | 4.53 | 0.034 |
| X1212 | 1 | 13881.055 | 13881.055 | 3.11 | 0.078 |
| X1211 | 1 | 4630.26 | 4630.26 | 1.038 | 0.31 |
| X1112 | 1 | 566.11 | 566.11 | 0.127 | 0.72 |
| Residuals | 471 | 2100238.63 | 4459.105 | | |

The estimated effects on the marbling score for each T244C.C575T genotype are:

| X2211 | X1122 | X1212 | X1211 | X1112 | X1111 |
|---|---|---|---|---|---|
| 24.2 | −23.47 | −3.35 | 29.76 | 12.44 | 0 |

Including the T244C.C575T genotypes in the model rather than the T244C.C575T haplotypes accounts for significantly more variation (F-value=9.484, p<0.0000043). This large difference suggests that the combination of haplotypes rather than a single haplotype is important in predicting marbling, i.e. genotype effect≠Σ allele effects. There are several alternatives that could explain this observation. First, while the dominance of a particular SNP could explain the observed results, estimates for the genotypes 2211, 1122, and 1212 suggest an additive gene action. Second, inter-locus interaction, with more than one single polymorphic site in the genomic DNA being responsible for the effect, could explain the observed result. Finally, the results suggest that the haplotype T244C.C575T may not itself contain the causative mutation(s) or contributing feature of the trait. Nevertheless, the two-locus haplotype is predictive of an animal's marbling phenotype.

The estimated effect for the various statistical models described herein is based on the USDA scale for grading meat. The USDA categorizes meat on a 1000 point scale. The USDA grade of meat depends on the score it receives from a qualified operator, which determines the retail price of the meat. The USDA scale is as follows: standard (0-299 points); select (300-399 points); low choice (400-499 points); choice (500-599 points); high choice (600-699); and prime (700-1000). The above statistical information indicates that animals with the favorable genotype of 2211 versus animals with the unfavorable genotype of 1122 will score approximately 50 points higher on the 1000 point scale. Thus, animals that are for example in the upper half of USDA select and high choice will be able to generate through directed breeding programs progeny that produce USDA choice and prime Quality Grades, respectively. Thus, progeny with the favorable marbling genotype, i.e. 2211 and 1211, will be more valuable to both retailers and consumers.

Another important aspect of using the two-locus genotypes is that the genotypes now can be treated as a fixed effect in the analysis. Fitting the genotype T244C.C575T as a fixed effect in the model gave the following estimates of genotype effects:

| T791C.C1121T | Code | Haplotype | Genotype Effect | Observation |
|---|---|---|---|---|
| 2211 | A<br>A | 2 1<br>2 1 | 24.20 | 161 |
| 1122 | a<br>a | 1 2<br>1 2 | −23.47 | 59 |
| 1212 | A<br>a | 2 1<br>1 2 | −3.35 | 244 |
| 1211 | A<br>B | 2 1<br>1 1 | 29.76 | 34 |
| 1112 | a<br>B | 1 2<br>1 1 | 12.44 | 19 |
| 1111 | B<br>B | 1 1<br>1 1 | 0 | 6 |

There are three haplotypes present in the population, which have been designated A, a, and B. Haplotype 22 (=b) is not present in any of the animals studied in the Angleton Family Pedigree. Estimates of effects of genotypes containing haplotype B are not consistent with the effects that include the A and a haplotypes. Because genotype 1111 (BB) is only present in a single family and confounds the family effect, the model was refitted to exclude animals with genotype 1111 and genotype 1112 (only 19 observations). The results of the model are below:

|  | Df | Sum of Sq | Mean Sq | F Value | Pr(F) |
|---|---|---|---|---|---|
| BYS | 10 | 108202.57 | 10820.26 | 2.497 | 0.0063 |
| FAMILY | 34 | 1983571.19 | 58340.33 | 13.46 | 0.00 |
| DOF | 1 | 4553.44 | 4553.44 | 1.05 | 0.306 |
| OOAGE | 1 | 32734.64 | 32734.64 | 7.55 | 0.00623 |
| T791C.C1121T | 3 | 85037.21 | 28345.74 | 6.54 | 0.000245 |
| Residuals | 448 | 1941274.45 | 4333.20 |  |  |

The estimated effects in the above comparison are:

| 1122 (aa) | 1211 (BA) | 1212 (Aa) | 2211 (AA) |
|---|---|---|---|
| 0 | 50.27 | 17.73 | 44.93 |

Haplotypes A and B are associated with a positive effect on marbling while haplotype a is associated with a negative effect. The above estimated effects indicate that animals with the favorable genotype 2211 or 1211 will have increased marbling while animals with the unfavorable genotype of 1122 will have decreased marbling in comparison to the 2211 and 1211 animals.

An analysis was also performed using the two-locus genotype (T244C.C575T) for all QTL traits analyzed in the pedigree (Estimates±standard error (SD)). Statistically significant results (p-value<0.05) were obtained for the following traits: yearling weight (YRWT), actual fat thickness over the 10th and 11th rib (ACFT), marbling (MARB), quality grade (QG), connective tissue (CTIS), flavor (FLV), and juiciness (JC). These results are summarized below:

| TRAIT | No. of observations | p-value | Estimates ± SD ||||||
|---|---|---|---|---|---|---|---|---|
|  |  |  | X1111 | X1112 | X1122 | X1211 | X1212 | X2211 |
| YRWT | 559 | 0.0267 | 0 | 3.695<br>16.844 | −3.676<br>16.85 | −5.75<br>16.48 | 3.75<br>16.25 | −8.68<br>16.459 |
| ACFT | 539 | 0.00705 | 0 | −2.39<br>2.164 | −0.412<br>2.165 | 1.66<br>2.115 | 1.13<br>2.08 | 1.388<br>2.11 |
| MARB | 539 | 0.000823 | 0 | 10.68<br>34.71 | −24.547<br>34.733 | 30.091<br>33.93 | −3.48<br>33.40 | 23.34<br>33.867 |
| QG | 539 | 0.000094 | 0 | 6.28<br>18.90 | −13.608<br>18.91 | 22.89<br>18.475 | 4.757<br>18.19 | 17.88<br>18.44 |
| CTIS | 532 | 0.0423 | 0 | −0.60<br>0.29 | −0.26<br>0.29 | 10.166<br>0.28 | −0.13<br>0.28 | −0.16<br>0.286 |
| FLV | 533 | 0.00601 | 0 | −0.036<br>0.195 | 0.325<br>0.197 | 0.33<br>0.19 | 0.368<br>0.19 | 0.349<br>0.19 |
| JC | 533 | 0.02124 | 0 | −0.527<br>0.317 | −0.166<br>0.32 | 0.016<br>0.31 | −0.03<br>0.308 | −0.138<br>0.312 |

Positive values for each of the six two-locus genotypes for T244C.C575T(X) indicate that the genotypes are desirable for the following traits:

YRWT, MARB, QG, FLV, and JC. Negative values for the same genotypes are desirable for the following traits: ACFT (reduced external fat) and CTIS (reduced connective tissue for more tender meat).

All of the compositions and methods disclosed and claimed herein can be made and executed without undue experimentation in light of the present disclosure. All patents and publications mentioned in the specification are indicative of the levels of skill of those skilled in the art to which the disclosure pertains. While the compositions and methods of this invention have been described in terms of preferred embodiments, it will be apparent to those of skill in the art that variations may be applied to the compositions and/or methods and in the steps or in the sequence of steps of the methods

What is claimed is:

1. An isolated nucleic acid molecule consisting of SEQ ID NO:1 or SEQ ID NO:27.

2. An isolated nucleic acid molecule comprising SEQ ID NO:1, wherein position 244 of SEQ ID NO:1 is a C and position 575 of SEQ ID NO:1 is a T.

3. An isolated nucleic acid molecule consisting of SEQ ID NO:21, or the complement thereof.

4. A kit for identifying a single nucleotide polymorphism (SNP) in the bovine somatostatin (SST) gene, the kit comprising at least a first SNP identifying reagent and at least a first SNP detecting reagent, wherein said first SNP identifying reagent comprises nucleic acid wherein said nucleic acid consists of SEQ ID NO:21, or the complement thereof.

5. The kit of claim 4, further comprising a detectable label, wherein the first SNP identifying reagent is operably attached to the detectable label.

* * * * *